United States Patent
Funamizu et al.

(10) Patent No.: US 6,864,250 B1
(45) Date of Patent: Mar. 8, 2005

(54) N-ACYLATED LIPOPHILIC AMINO ACID DERIVATIVES

(75) Inventors: Hidenori Funamizu, Kyoto (JP); Nobuo Ishiyama, Kyoto (JP); Satoru Ikegami, Kyoto (JP); Tadashi Okuno, Kyoto (JP); Kiyoshi Inoguchi, Kyoto (JP); Ping Huang, Mountain View, CA (US); Gilda Loew, Mountain View, CA (US)

(73) Assignees: Kaken Pharmaceutical Co., Ltd., Tokyo (JP); Molecular Research Institute, Mountain View, CA (US)

( * ) Notice: Subject to any disclaimer, the term of this patent is extended or adjusted under 35 U.S.C. 154(b) by 0 days.

(21) Appl. No.: 09/485,845

(22) PCT Filed: Aug. 20, 1998

(86) PCT No.: PCT/US98/17232

§ 371 (c)(1),
(2), (4) Date: Apr. 26, 2000

(87) PCT Pub. No.: WO99/09991

PCT Pub. Date: Mar. 4, 1999

Related U.S. Application Data

(63) Continuation-in-part of application No. 08/916,575, filed on Aug. 22, 1997, now abandoned.

(51) Int. Cl.[7] .................. A61K 31/55; A61P 19/00; C07D 267/02; C07D 281/02
(52) U.S. Cl. .............. 514/211.04; 514/211.07; 540/488; 540/491
(58) Field of Search ............... 514/211.04, 211.07; 540/488, 491

(56) References Cited

U.S. PATENT DOCUMENTS

| | | | |
|---|---|---|---|
| 5,441,950 A | 8/1995 | Collins et al. | 514/211 |
| 5,449,675 A | 9/1995 | Chandrakumar et al. | 514/211 |

FOREIGN PATENT DOCUMENTS

| | | |
|---|---|---|
| EP | 0 411 751 A1 | 2/1991 |
| WO | WO92/16524 | 10/1992 |
| WO | WO96/15148 | 5/1996 |
| WO | WO96/35713 | 11/1996 |
| WO | WO97/00894 | 1/1997 |
| WO | WO97/06803 | 2/1997 |
| WO | WO97/22367 | 6/1997 |

Primary Examiner—Brenda Coleman
(74) Attorney, Agent, or Firm—Nixon & Vanderhye P.C.

(57) ABSTRACT

Compounds of structural Formula (I) where A is a lipophilic group including an aliphatic bridging group, B is a lipophilic group, D is a group having at least one amino or substituted amino group and R is hydrogen, alkyl or cycloalkyl, and pharmaceutically acceptable salts and individual isomers thereof, which have growth hormone releasing activity in humans or animals

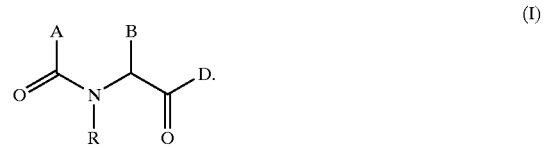

11 Claims, No Drawings

N-ACYLATED LIPOPHILIC AMINO ACID DERIVATIVES

This application is a national stage entry under 35 U.S.C. § 371 of PCT/US98/17232, filed Aug. 20, 1998 which is a continuation-in-part of application Ser. No. 08/916,575, filed Aug. 22, 1997, now abandoned.

FIELD OF THE INVENTION

The present invention related to synthetic peptidomimetics having growth hormone releasing activity in humans or animals, and their use in humans for treating medical disorders resulting from a deficiency in growth hormone, or use in animals for increasing the rate and extent of growth, or for increasing the milk or wool production, or for treatment of ailments.

BACKGROUND OF THE INVENTION

Growth hormone, which is secreted from the pituitary, stimulate growth of all tissues of the body that are capable of growing. In addition, growth hormone is known to have following basic effects on the metabolic process of the body: 1) Increase the rate of protein synthesis in the cells of the body, 2) Decrease rate of carbohydrate utilization in the cell of the body; 3) Increase mobilization of the fatty acids and use of the fatty acids for the energy.

Artificial manipulation of growth hormone levels has been demonstrated to have significant therapeutic utility. Human growth hormone supplementation has been shown to be an effective treatment for growth hormone deficiency and their related diseases states in humans, such as short statue (Robinson and Clark., Growth Hormone: Basic and Clinical Aspect, Isaksspn, Binder. Hall and Hokifelt eds., Amsterdam, p109–27 (1987).

Apart from this application, studies have uncovered new and significant properties of growth hormone which lead further importance to the ability to control growth hormone levels. For example, recent clinical studies indicate that growth hormone supplementation may be useful in combating the milaladies of aging in humans. Elevated growth hormone levels in animals also have been shown to result in increase lean mass muscle. One application of this latter observation could results in higher production of leaner meat products or larger and/or stronger animals. However, their clinical and/or animal application, as with recombinant growth hormone, has been limited due to their high cost and lack of oral efficiency (Low,L.C.K., Neuroendoclinology, 1991, 53 (Supp. 1), 37–40: Thomer, M. O., Acta Pediatr 1993, 388 (Supp. 1), 2–7).

The release of growth hormone from pituitary organs is under tight control of a second protein, growth hormone releasing factor (GRF), which is also commonly known in the art as somatomedin growth hormone releasing hormone (GHRH), growth releasing hormone (GRH) and neurotransmitters either directly or indirectly. Growth hormone release can be stimulated by growth hormone releasing hormone and inhibited by somatostatin. In both cases the hormones are released from the hypothalamus but their action is mediated primarily via specific receptors located in the pituitary. As a result, the development of synthetic growth hormone releasing agents and the use of drugs acting through established neurotransmitter systems in the brain to stimulate growth hormone releasing are being considered as alternative to highly expensive and lack of oral efficiency growth hormone replacement therapy for the restoration on normal serum growth hormone levels (Pharm. Rev., 46, 1–33(1994)).

Even before the discovery of the endogenous releasing factor GHRH in 1982 (Guillemin, R. et al., Science, 1982, 218:585–587), Bowers and co-workers had reported on a series of peptides derived from Leu and Met enkephalins which specifically release growth hormone from pituitary (Bowers, C. Y. et al., Molecular Endoclinology. Maclntyne I (Ed) Elsevier/North Holland Biomedical Press, Amsterdam 1977, 287–292). It was later discovered that these growth hormone releasing peptides (GHRPs) act directly on the pituitary through a different signal transduction pathway from that of GHRH. In combination with GHRH, GHRPs act synergistically at the pituitary to release growth hormone. A hypothalamic binding site for GHRPs, which may be partially responsible for their growth hormone releasing in vivo by releasing endogenous GHRH, has been identified (Codd, E. E. et al., Neuropharmacology, 1989, 28, 1139–1144; Howard, D. H. et al., Science, 1996, 273, 974–976). Momany and Bowers employed molecular modeling techniques to discovered the growth hormone releasing hexapeptide GHRP-6, which is extremely potent and specific growth hormone secretagogue in human. More potent analogs of GHRP-6 have recently discovered and presently under clinical evaluation (Laron, A. Drugs, 1995, 50, 595–601). While GHRP-6 is a much more smaller peptide than either recombinant growth hormone or growth hormone releasing hormone, it still has low oral bioavailability in human (0.3%). However, GHRP-6 has demonstrated that relatively small molecule, with its possible advantage of lower cost and oral bioavailability, may be a viable alternative to subcutaneous treatment with recombinant growth hormone (DeVita, R. J. et al., Drugs of the Future, 1996, 21(3), 273–281).

| | |
|---|---|
| His-D-Trp-Ala-Trp-D-Phe-Lys-NH$_2$ | GHRP-6 |
| Ala-His-D-β-Nal-Ala-Trp-D-Phe-Lys-NH$_2$ | GHRP-1 |
| D-Ala-D-β-Nal-Ala-Trp-D-Phe-Lys-NH$_2$ | GHRP-2 (KP-102) |
| His-D-2-MeTrp-Ala-Trp-D-Phe-Lys-NH$_2$ | Hexarelin |

In recent years significant efforts have been taken to develop non-peptidyl analogs of this series of compounds. Such compounds, termed growth hormone secretagogues, should be orally bioavailable, induce production or release of growth hormone, and act as synergistically with growth hormone releasing hormone. Representative growth hormone secretagogues are disclosed in U.S. Pat. Nos. 3,239,345; 4,036,979; 4,411,890; 5,206,235; 5,248,841; 5,310,017; 5,310,737; 5,434,261; 5,552,385; 5,559,128; EP 144,230; EP 513,974; WO 94/07486; WO 94/08583; WO 94/11012; WO 94/13696; WO 95/03290; WO 95/09633; WO 95/12598; WO 95/13069; WO 95/14666; WO 95/16692; WO 95/16675; WO 95/17422; WO 95/17423; WO 95/34311; WO 96/02530; WO 96/05195; WO 96/13265; WO 96/15148; WO 96/22997; WO 96/24587; WO 96/35713; WO 96/38471; WO 97/00894; WO 96/24580; WO 97/06803; WO 97/07117; WO 97/11697; WO 97/15191; WO 97/22620; WO 97/23508; WO 97/24369 and Science, 260,1640–1643(1993).

U.S. Pat. No. 5,206,235 issued Apr. 27, 1993, describes a series of benzolactam compounds typified by the following structure. These compounds have demonstrated

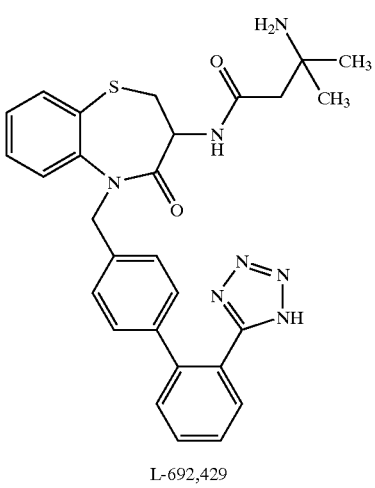

L-692,429 clinical activity in humans in raising the growth hormone secretory levels (B. J. Gertz., Journal of Clinical Endocrinology and Metabolism, 77, 1393–1397(1993)).

Second generation of growth hormone secretagogues is described in WO 94/13696, WO 96/15148. These compounds are typified by the following structure.

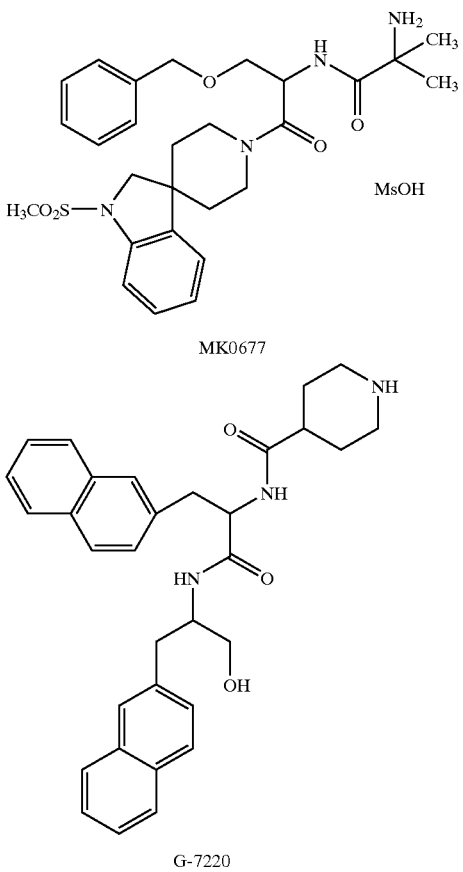

MK0677

G-7220

A number of these compounds are reported to be safe and effective in promoting endogenous growth hormone release in humans, however, there remain problems with oral availability and specificity.

SUMMARY OF THE INVENTION

The instant invention is directed to certain novel amide compounds which have the ability to stimulate the release of natural or endogenous growth hormone. It is a still further object of this invention to provide more potent growth hormone secretagogues than those of the prior, especially "GHRP-6", "GHRP-1", "GHRP2(KP-102)", "L-692,429", "L-692,585", "MK-0677" and "G07220". It is a further object to provide growth hormone secretagogues that are specific for growth hormone release and do not cause significant release of other hormones, especially; LH, FSH, TSH, ACTH, prolactin, vasopressin, oxytacin, insulin, and cortisol. The compounds thus have the ability to be used to treat conditions which require the stimulation of growth hormone production or in animals used for food, wool, and milk production where the stimulation of growth hormone will result in a large, more productive animals. Thus, it is an object of the present invention to described the compounds. It is a further object of this invention to described procedures for the preparation of such compounds and intermediates. A still further object is to describe the use of such compounds to increase the secretion of growth hormone in humans and animals. It is a still further object to provide compositions containing the compounds for the use of treating humans and animals so as to increase the levels of growth hormone secretions. These and other objects of the invention will be apparent from the following specification.

The Strategy of Lead Finding and Lead Optimization

It is the object of this invention to provide a novel class of non-peptidyl growth hormone secretagogues using an approach of computer-aided rational drug design and discovery. The computational strategy described below has produced 3D pharmacophores for 3D database search in the lead finding, and provided site-dependent quantitative structure activity relationship (QSAR) for fragment property refinement in the lead optimization, leading to the development of novel potent growth hormone secretagogues. The computational strategy has been implemented through three stages in the invention:

(1) conceptual stage—generation and validation of 3D-pharmacophores (2) discovery stage—database search and compound modification (3) optimization stage—development of QSAR for refinement (1) Conceptual Stage—Pharmacophore Development The structural components of the growth hormone releasing peptides(GHRPs) and non-peptidyl derivatives are important for their growth hormone releasing potency. It is thus the crucial step in rational design to develop 3D pharmacophores, which represent the three dimensional arrangement of functional groups essential for activity, from a number of compounds with known activities, similar mechanism of action, and similar in vivo properties. The seven potent peptides selected for pharmacophore generation in the present invention include "GHRP-6", "[D-Lys$^6$] GHRP-6", "KP102(GHRP-2)", and its four peptidyl analogs. Non-peptidyl analogs chosen for pharmacophore development include "L-692,429". "L-692,585", "MK-0677", and "L-164,080". In addition, one inactive peptide "[Val$^3$]GHRP-6", and one inactive non-peptide "L-692,428" were used as control. Conformations of each of these compounds were generated using a strategy of repeated cycles of high (900° K) and low (300° K) temperature molecule dynamics combined with energy minimization of molecule structures. Details of this strategy are described by Chew, C. et al. (Mol. Pharm., 1991, 39, 502). The calculations were performed using Quanta/CHARMm 4.0 (Molecular Simulation, Inc. USA). The search for the form in which flexible molecules such as peptides bind to receptors is a challenging task because many low-energy conformations are accessible and they coexist in equilibrium. The complexity increases enormously when several diverse families of fairly flexible molecules are included and the goal is to identify the common geometric arrangements of moieties that are determinants of receptor recognition or activation because all low-energy conformations of each molecule should be included in analysis. A novel computer program, DistComp, was thus developed to perform systematic and automated comparisons of molecular conformations in different compounds for the determination of 3D pharmacophores (Huang, P. et al., J. Computer-Aided Molecular Design., 1997, 11, 21–28). DistComp provides a procedure for identifying common spatial arrangements of selected moieties in a given set of molecules. No prior assumption of an active conformation is necessary. There is also need for a rigid template. However, central to this procedure is the selection of sets of common functional moieties assumed to be important for recognition or activation. The validity of these candidate recognition or activation sites is then assessed by the program: for each hypothetical set of recognition or activation moieties selected, the program systematically determines whether any common 3D relationships among them exists in active analogs but are absent in inactive ones. Each set of proposed chemical moieties that satisfies this requirement, together with the common spatial arrangements identified, comprises candidate 3D pharmacophores.

Using the program DistComp, a convergent model termed "Pharmacophore I" which is common to all seven peptides and two non-peptides ("L-692,429", "692-585") was successfully developed. "Pharmacophore I" was subsequently validated using two new potent growth hormone secretagogues, "G-7220", "G-7134", developed at Genentech by that time with the results indicating that the two compounds fit well to the pharmacophore. Another convergent model, termed "Pharmacophore II", was developed when "MK-0677" and "L-164,080" were reported by Merck to be potent growth hormone secretagogues. "Pharmacophore II" is common to all seven peptides and two non-peptides, "MK-0677" and "L164,080". Pharmacophore I and II have some common features, but differ in two components.

(2) Discovery Stage-Database Search and Compound Modification

The successful development of the 3D pharmacophores provides a logical framework for the design and discovery of novel growth hormone secretagogues in the present invention. Using these 3D pharmacophores, 3D database search was performed of a number of databases including MDDR, Chapman & Hall Database of Organic Compounds, Maybridge, CAS30K, and NCI Database. Both 3D rigid and flexible search methods were used. While a rigid search does static comparison of the 3D structure stored in database of a compound with the pharmacophore, a flexible search takes into account molecular flexibility. Compounds obtained from database search were then screened and modified using structural and chemical intuition, with emphasis on scaffold novelty, conformational rigidity, minimum extra components, and chemical aspects such as excluding compounds that are polymeric, clatbrate, molecular complex, metal complex, toxic, or peptides. Modification of compounds was performed mainly on compounds that have novel scaffolds. Subsequent computer modeling studies were then performed on compounds from the database search which had been either modified or obtained from a flexible search, in order to determine the extent to which they conformed either Pharmacophore I or II. Candidates which were found to be consistent with the pharmacophores and easy to synthesize were then selected for synthesis and pharmacological testing. Using these strategies, initial lead compounds in the present prevention have been successfully designed and discovered.

(3) Optimization Stage—Development of QSAR for Refinement

The goal in this stage was to enhance the activity of initial lead compounds from, typically, micromolar into the nanomolar range. While experimentalists focused on making various analogs of the leads for SAR studies, computational efforts focused on the development of site-dependent QSAR (Quantitative Structure Activity Relationship) procedure embodied in a suite program, for refinement of the lead compounds. The innovative approach is in addition to improving compounds by making them more consistent with the pharmacophores in terms of the three-dimeasional arrangement/location of the functional groups.

Preliminary investigation were performed that demonstrated no significant correlation between the overall molecular properties of growth hormone releasing peptides and their activity. Clearly, growth hormone secretion activity cannot be described simply by these molecular descriptors. A possible explanation for this is that the overall molecular descriptors can be significantly modulated by the molecular regions which are not important to the drug-receptor interaction. As we have already experienced in many cases, complex drug interactions cannot be simply described by overall descriptors of a molecule.

A novel site-depended QSAR method was, therefore, developed to specifically identify the function of each pharmacophoric site that comprise the 3D pharmacophores. These supplementary requirements of site-dependent properties were used as additional criteria for optimizing and refining novel compounds on the basis of 3D pharmacophore. The most challenging aspect of this task was to identify and calculate relevant properties of each pharmacophoric site (i.e. site-dependent properties) rather than the properties of the entire molecule. These properties can be used in a regression analysis to identify the ones that modulate activity. Among the library of properties that can be calculated for each site are: 1) regional net atomic charges; 2) polarizability; 3) free energy of solvation; 4) Van der Waals volume; 5) hydrophobicity; 6) proton donating ability; 7) proton accepting ability; 8) molecular flexibility. A prerequisite to use of this site-dependent QSAR procedure is the definition of the pharmacophoric sites or fragments that comprise an already identified 3D pharmacophore. A pharmacophoric site in a molecule is defined as a fragment consisting of a Pharmacophore atom (core), which is a component in 3D Pharmacophore, together with its immediate neighbors in the molecule and capping atoms. The site-dependent QSAR studies have been performed on eight peptides including "GHRP-6,", "[D-Lys$^6$]GHRP-6", "G-7134", "KP-102" and its four peptidyl analogs. The results demonstrated clearly the correlation of some fragment properties, particularly bydrophobicity, in some specific regions in these molecules with their growth hormone secretion activity. These results provided a useful guide for modification of the specific pharmacophoric sites leading to enhanced activity.

(4) Summary

The computational strategies used here: extensive conformational studies and Distcomp analysis for a small number of known peptide and non-peptide analogs have led to the successful development of 3D pharmacophores for activation of growth hormone secretagogues agonists. These 3D activation pharmacophores have provided the essential enabling basis for the design and discovery of the novel non-peptidyl growth hormone secretagogues in this invention. Database search using the 3D pharmacophores together with strategies for compound screening and modification have led to the discovery of initial lead compounds. A site-dependent QSAR developed for fragment property refinement has provided guidelines for lead optimization.

These three steps-pharmacophore development, lead discovery and optimization together have led to the development of the novel potent growth hormone secretagogues described in this invention.

DETAILED DESCRIPTION OF THE INVENTION

Present invention provides the novel compounds presented by the structural Formula I:

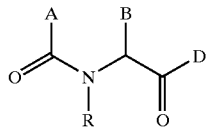

wherein
A is a lipophilic group comprising an aliphatic bridging group, and
B is a lipophilic group, and
D is a group having at least one amino or substituted amino group, and
R is hydrogen, alkyl, or cycloalkyl, and pharmaceutically acceptable salts and individual isomers thereof.
In Formula I, A is preferably

wherein
$A^1$ is an aliphatic or aromatic rig which may have at least one hetero atom, and
$M^1$ is substituted or unsubstituted alkylene.
$A^1$ is preferably

wherein
$A^2$ is single or fused ring, each ring constituting $A^2$ is on aliphatic or aromatic ring which may have at least one hetero atom, each ring constituting $A^2$ may be substituted by at least one group selected from halogen, hydroxy, alkyl, substituted alkyl, cycloalkyl, substituted cycloalkyl, alkoxy substituted alkoxy, perfluoroalkyl, perfluoroalkoxy, cyano, nitro, substituted sulfonyl, substituted sulfenyl, substituted sulfinyl, mercapto, substituted carbonyl, amino, substituted amino, aryl, and substituted aryl, and
$M^1$ is alkylene which may be substituted by halogen, hydroxy, $(C_1-C_5)$alkyl, and/or $(C_{1-C5})$alkoxy.
$A^1$ is more preferably

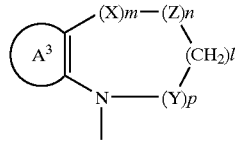

wherein
$A^3$ is a 5, 6, or 7 membered aromatic ring which may be comprised of at least one hetero atom, and may be substituted by a group selected from halogen, hydroxy, $C_1-C_5$)alkyl, $(C_1-C_5)$alkoxy, $(C_1-C_5)$perfluoroalkyl, $(C_1-C_5)$perfluoroalkoxy, nitro, cyano, substituted sufonyl, substituted sulfenyl, substituted sulfinyl, mercapto, amino, substituted amino, substituted carbonyl, phenyl and/or substituted phenyl, and
$A^3$ can be fused with at least 5 to 8 membered aliphatic or aromatic ring which may be consisted of at least one hetero atom, and 1 is 0, 1, or 2, and
X is —$CH_2$—, —O—, —S(O)r—, —C(O)—, —C(S)—, —CH=CH—, —CH(OH)—, or $NR^4$—, and
$R^4$ is hydrogen, $(C_1-C_5)$alkyl, $(C_3-C_8)$cycloalkyl, acyl, or alkoxycarbonyl, and
m is 0. 1, or 2, and
Y is —C(O)—, —C(S)—, or $(C_1-C_5)$alkylene which may be substituted by $(C_1-C_5)$alkyl,
p is 0, 1, or 2, and
Z is substituted or unsubstituted$(C_1-C_5)$alkylene, —$NR^4$—, or

wherein
$A^4$ is a 5 or 6 membered aromatic ring which may be comprised of at least one hetero atom, and
$A^4$ may be substituted by a group selected from halogen, hydroxy, $(C_1\sim C_5)$ alkyl, $(C_1-C_5)$alkoxy, $(C_1-C_5)$ perfluoroalkyl, $(C_1-C_5)$perfluoroalkoxy, nitro, cyano, amino, substituted amino, phenyl and/or substituted phenyl, or

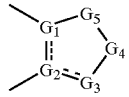

wherein
$G_1$ and $G_2$ are independently carbon or nitrogen, and one of --- may represent double bond when either $G_1$ and $G_2$or $G_2$ and $G_3$ are carbon, and
$G_3$, $G_4$, and $G_5$ are independently —O—, —S(O)r—, —C(O)—, —C(S)—, —CH=CH—, —CH(OH)—, —$NR^4$—, or $(C_1-C_5)$alkylene,
r is 0, 1, or 2, and
n is 0 or 1.
Examples of preferred $A^1$ is include 10,11-Dihydrodibenzo[b,f][1,4]oxazepin-11-one,
3,4-Dihydro-2H-quinoline,
2Oxo-3,4,5,6-tetrabydro-2H-benzo[b]azocine,
2,3-Dioxo-2,3-dihydro-indole,
2Oxo-3,4-dihydro-2H-quinoline,
3Oxo-2,3-dihydro-pyrido[3,2-b][1,4]oxazine,
4-Methyl-2,5-dioxo-2,3,4,5-tetrahydro-benzo[e][1,4]diazepine,
2,3-Dihydro-1H-pyrrolo[2,1-c][1,4]benzodiazepin-5,11(10H, 11aH)-dione,
3Oxo-2,3-dihydro-benzo[1,4]thiazine,
6Oxo-11,12-dihydro-6H-dibenzo[b,f]azocine,
2Oxo-2,3,4,5-tetrahydrobenzo[b]azepine,
1,1,4-Trioxo-2,3-dihydro-benzo[1,5]thiazepine, 4Oxo-2,3-dihydro-1,5-benzothiazepine,
5,11-Dihydro-dibenzo[b,e]azepine,
5H-Dibenzo[b,e]azepin-6,11-dione,
5H-Dibenzo[b,f]azocin-6-one,
10H-Dibenzo[b,f][1,4]thiazepin-11-one,
5Oxo-5,10H-dibenzo[b,f][1,4]thiazepin-11-one,
5,5-Dioxo-5,10H-dibenzo-[b,f][1,4]thiazepin-11-one,
4Oxo-2,3-dihydro-[1,5]benzoxazepine,
6,2-Dioxo-6,6a,7,8,9,10-hexahydro-12H-benzo[e]pyrido[1,2-a][1,4]diazepine,
2-Oxo-2H-cyclohepta-4,6,8-trieno[b]pyrrole,
Phenothiazine, which may have substituted, In Formula I, B is preferably B is alkyl, substituted alkyl, cycloalkyl, substituted cycloalkyl, or aryl, arylalkyl or arylalkoxyalkyl which may be substituted on their aromatic ring.

B is more preferably

B is substituted or unsubstituted($C_5$–$C_{20}$)alkyl, phenylalkyl, naphtbylalkyl, 5,6,7,8-tetrahydro-naphthylalkyl, indolylalkyl, quinolylalkyl, or phenylalkoxyalkyl, which may be substituted by a group selected from halogen, hydroxy, ($C_1$–$C_5$)alkyl, ($C_1$–$C_5$)alkoxy, nitro, cyano, amino, substituted amino, phenyl, or substituted phenyl.

In Formula I, D is preferably

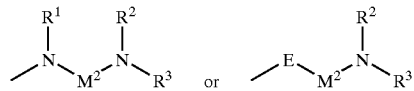

wherein $R^1$ is hydrogen, alkyl, substituted alkyl, cycloalkyl, or substituted cycloalkyl, and $R^2$ and $R^3$ are independently hydrogen, alkyl, substituted alkyl, acyl, amidino, alkoxycarbonyl, or either $R^2$ or $R^3$ can be taken together with $R^1$ to form alkylene, and $R^2$ and $R^3$ can be taken together to form alkylene, or heterocycle, and $M^2$ is:

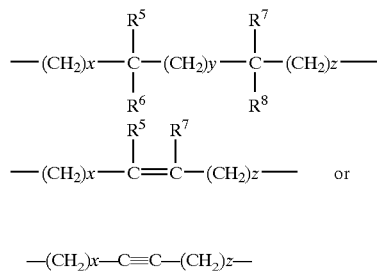

wherein x, y and z are independently an integer of 0 to 4, and $R^5$, $R^6$ $R^7$ and $R^8$ are independently hydrogen, halogen, alkyl, substituted alkyl, —$OR^9$, —$SR^9$, —$NR^9R^{10}$, —NHC(O)$R^9$, —OCO$R^9$, —C(O)O$R^9$, —OC(O)O$R^9$, —CONR$^9R^{10}$ or can be taken together with $R^1$ or $R^2$ to form alkylene or heterocycle, $R^9$ and $R^{10}$ are independently hydrogen, alkyl, substituted alkyl, and $R^9$ can be taken together with $R^1$ or $R^2$ to form alkylene, $R^5$ and $R^7$ or $R^6$ and $R^8$ can be taken together to form alkylene or heterocycle, or $R^5$ and $R^6$ or $R^7$ and $R^8$ can be taken together with the carbon atom to which $R^5$ and $R^6$, or $R^7$ and $R^8$ are bonded, respectively, to form carbonyl or thiocarbonyl or amino, and E is oxygen atom or sulfur atom.

Preferably combination is that $R^1$ is hydrogen, ($C_1$–$C_5$)alkyl, ($C_3$-$C_8$)cycloalkyl, ($C_1$–$C_5$)hydroxyalkyl, or ($C_1$–$C_5$)aminoalkyl, and $R^2$ and $R^3$ are independently hydrogen, ($C_1$–$C_5$)alkyl, substituted ($C_1$–$C_5$)alkyl, ($C_1$–$C_6$)acyl, or ($C_1$–$C_6$)alkoxycarbonyl, and $R^1$ and $R^2$ or $R^2$ and $R^3$ are can be taken together to form alkylene, $R^5$, $R^6$, $R^7$, and $R^8$ are independently hydrogen, halogen, ($C_1$–$C_5$)alkyl, substituted ($C_1$–$C_5$)alkyl, —$OR^9$, —$SR^9$—$NR^9R^{10}$, —OC(O)$OR^9$, —NHC(O)$R_9$, —C(O) $OR^9$, and $R^5$ can be taken together with $R^1$ or $R^2$ to form alkylene, $R^9$ and $R^{10}$ are independently hydrogen, ($C_1$–$C_{C5}$)alkyl, and $R^9$ can be taken together with $R^1$ or $R^2$ to form alkylene.

Examples of referred D include

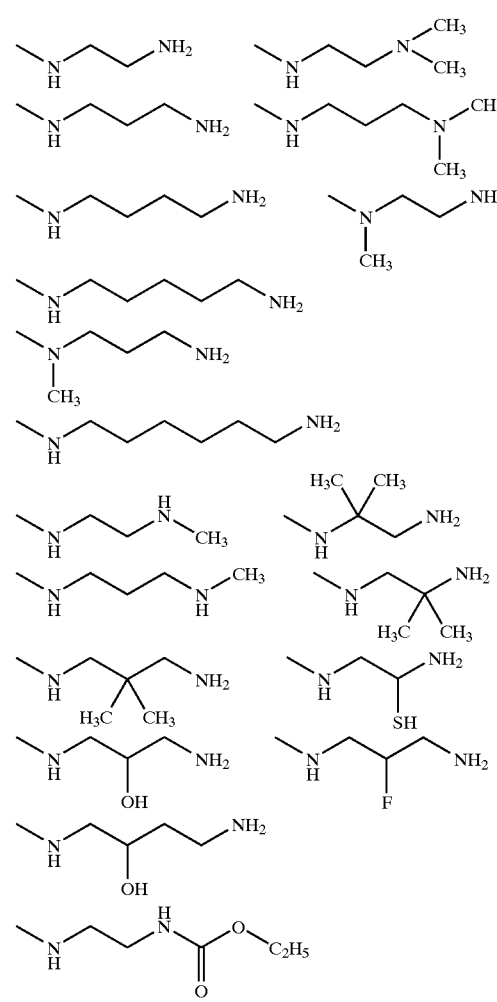

-continued

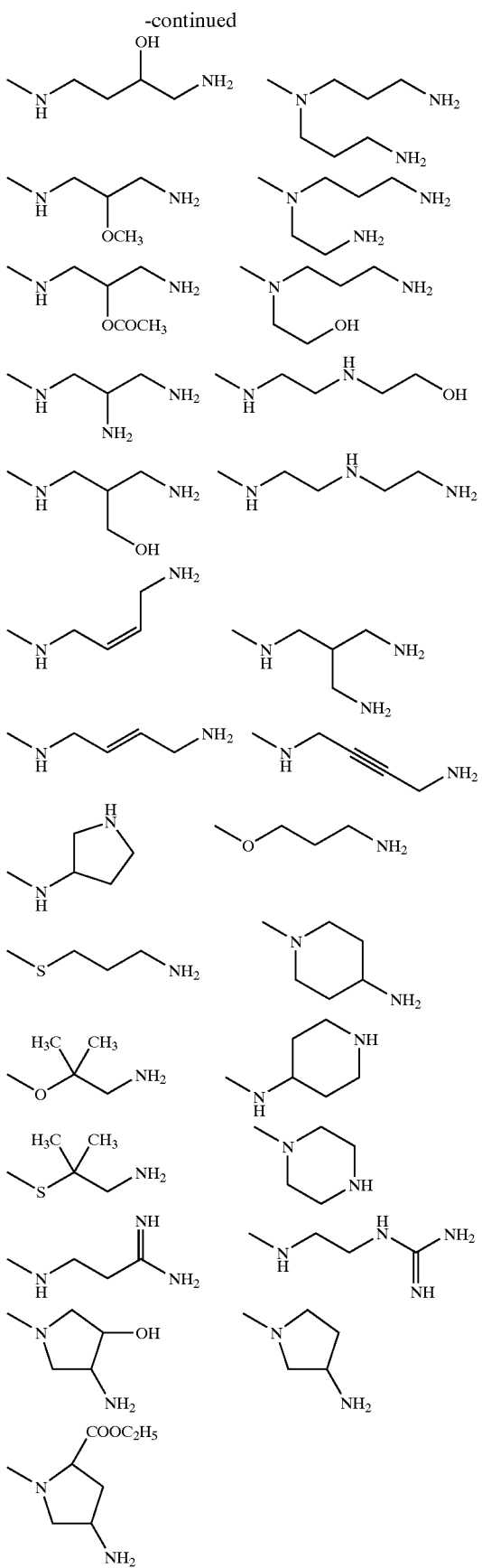

Examples of preferred comounds of Formula I include

N-(2-Aminoethyl)-3-phenyl-2(R)-[2-(1,1,4-trioxo-2,3-dihydro-[1,5]benzothiazepin-5-yl)acetylamino]propionamide;

N-[1(R)-(3-Aminopropylcarbamoyl)-2-(naphthalen-2-yl)ethyl]-3-(2-oxo-2,3,4,5-tetrahydro-benzo[b]azepin-1-yl)propionamide;

3-(3-Acetylamino-2-oxo-2,3,4,5-tetrahydro-benzo[b]azepin-1-yl)-N-[1(R)-(2-aminoethylcarbamoyl)-2-(naphthalen-2-yl)ethyl]propionamide;

N-[1(R)-(2-Aminoethylcarbamoyl)-2-(naphthalen-2-yl)ethyl]-3-(6oxo-11,12-dihydro-6H-dibenzo[b,f]azocin-5-yl)propionamide;

N-[1(R)-(3-Aminopropylcarbamoyl)-2-(naphthalen-2-yl)ethyl]-3-(6-oxo-11,12-dihydro-6H-dibenzo[b,f]azocin-5-yl)propionamide;

N-[1(R)-(3-Aminopropylcarbamoyl)-2-(naphthalen-2-yl)ethyl]-3-(4-oxo-2,3-dihydro[1,5]benzothiazepin-5-yl)propionamide;

N-1(R)-(4-Aminobutylcarbamoyl)-2-(naphthalen-2-yl)ethyl]-3-(4-oxo-2,3-dihydro-[1,5]benzothiazepin-5-yl)propionamide;

N-(4-Amino-butyl)-3-(naphthalen-2-yl)-2(R)-[2-(4-oxo-2,3-dihydro-[1,5]benzothiazopin-5-yl)acetylamino]propionamide;

N-[1(R)-(3-Aminopropylcarbamoyl)-2-(naphthalen-2-yl)ethyl]-3-(11-oxo-11H-dibenzo[b,f][1,4]oxazepin-10-yl)propionamide;

N-[1(R)-(3-Aminopropylcarbamoyl)-2-(naphthalen-2-yl)ethyl]-3-(5,11-dioxo-2,3-dihydro-1H,(11aS[-pyrrolo(2,1-c][1,4]benzodiazepin-10-yl)propionamide;

N-[1(R)-(3-Aminopropylcarbamoyl)-2-(naphthalen-2-yl)ethyl]-3-(6-methoxy-2-oxo-2,3,4,5-tetrahydro-benzo[b]azepin-1-yl)propionamide;

N-[1(R)-(3-Aminopropylcarbamoyl)-2-(naphthalen-2-yl)ethyl]-4-(4-oxo-2,3-dihydro-[1,5]benzothiazepin-5-yl)butyramide;

N-[1(R)-(4-Aminobutylcarbamoyl)-2-(naphthalen-2-yl)ethyl]-3-(4-methyl-2,5-dioxo-2,3,4,5-tetrahydro-benzo[e][1,4]diazepin-1-yl)propionamide N-[1(R)-(2-Aminoethylcarbamoyl)-2-(naphthalen-2-yl)ethyl]-3-(3-oxo-2,3-dihydro-benzo[3,2-b][1,4oxazin-4-yl)propionamide;

N-[1(R)-(3-Aminopropylcarbamoyl)-2-(naphthalen-2-yl)ethyl]-3-(3-oxo-2,3-dihydro-benzo[1,4oxazin-4-yl)propionamide;

N-1(R)-(3-Aminopropylcarbamoyl)-2-(naphthalen-2-yl)ethyl]-3-(2-oxo-3,4,5,6-tetrahydro-2H-benzo[b]lazocin-1-yl)propionamide;

N-(2-Amino-2-methylpropyl)-3-(naphthalen-2-yl)-2(R)-[3-(4-oxo-2,3-dihydro-[1,5]benzothiazepin-5-yl)propionylamino]propionamide N-[1(R)-(3-Aminopropylcarbamoyl)-2-(naphthalen-2-yl)ethyl]-3-(2-methyl-4-oxo-2,3-dihydro[1,5]benzothiazepin-5-yl)-propionamide;

N-[1(R)-(3-Aminopropylcarbamoyl)-2-(naphthalen-2-yl)ethyl]-4-(6oxo-11,12-dihydro-6H-dibenzo[b,f]azocin-5-yl)butyramide;

N-[1(R)-(3-Aminopropylcarbamoyl)-2-(naphthalen-2-yl)ethyl]-4-(3-oxo-2,3-dihydro-benzo[1,4]thiazine-4-yl)butyramide;

N-[1(R)-(3-Methylaminopropylcarbamoyl)-2-(naphthalen-2-yl)ethyl]-3-(4-oxo-2,3-dihydro-[1,5]benzothiazepin-5-yl)propionamide;

N-[1(R)-(3-Methylaminopropylcarbamoyl)-2-(naphthalen-2yl)ethyl]-4-(4-oxo-2,3-dihydro-[1,5]benzothiazepin-5-yl)butyramide;

N-(1(R)-[(3-Aminopropyl)-methylcarbamoyl]-2-(naphthalen-2-yl)ethyl]-4-(4-oxo-2,3-dihydro-[1,5]benzothiazepin-5-yl)butyramide N-(3-Amino-2-hydroxypropyl)-3-(naphthalen-2-yl)-2(R)-[3-(4-oxo-2,3-dihydro-[1,5]benzothiazepin-5-yl)propionylamino]propionamide;

N-[1(R)-(3-Amino-2-hydroxypropylcarbamoyl)-2-(naphthalen-2-yl)ethyl]-4-(4-oxo-2,3-dihydro-[1,5]benzothiazepin-5-yl)butyramide;

N-[1(R)-(2-Aminoethylcarbamoyl)-2-(naphthalen-2-yl)ethyl]-4-(4-oxo-2,3-dihydro-[1,5]benzotbiazepin-5-yl)butyramide;

N-1(R)-[Bis-(3-aminopropyl)-carbamoyl]-2-(naphthalen-2-yl)ethyl]-4-(4-oxo-2,3-dihydro-[1,5]benzothiazepin-5-yl)butyramide;

N-[1(R)-(3-Aminopropylcarbamoyl)-2-(naphthalen-2-yl)ethyl]-4-(1,1,4-trioxo-2,3-dihydro-[1,5]benzothiazepin-5-yl)butyramide;

N-[1(R)-(3-Aminopropylcarbamoyl)-2-(naphthalen-2-yl)ethyl]-4-(11-oxo-11H-dibenzo[b,f][1,4]oxazepin-10-yl)butyramide;

N-[1(R)-(3-Aminopropylcarbamoyl)-2-(naphthalen-2-yl)ethyl]-3-(phenothiazin-10-yl)propionamide;

N-[1(R)-(3-Amino-2-hydroxypropylcarbamoyl)-2-(naphthalen-2-yl)ethyl]-3-(6-oxo-11,12-dihydro-6H-dibenzo[b,f]azocin-5-yl)propionamide;

N-(3-Amino-2-hydroxypropyl)-2(R)-[3-(6-methoxy-2-oxo-2,3,4,5-tetrahydro-benzo[b]azepin-1-yl)-propionylamino]-3-(naphthalen-2-yl)propionamide;

N-(3-Amino-2-hydroxypropyl)-3-(naphthalen-2-yl)-2(R)-[3-(2-oxo-2,3,4,5-tetrahydro-benzo[b]azepin-1-yl)propionylamino]propionamide;

N-(3-Amino-2-hydroxypropyl)-3-(naphthalen-2-yl)-2(R)-[3-(2-oxo-3,4,5,6-tetrahydro-2H-benzo[b]azocin-1-yl)propionylamino]propionamide;

N-[1(R)-(3-Aminopropylcarbamoyl)-2-(naphthalen-2-yl)ethyl]-5-(4-oxo-2,3-dihydro-[1,5]benzothiazepin-5-yl)pentanamide;

N-[1(R)-(2-aminoethylcarbamoyl)-2-(naphthalen-2-yl)ethyl]-5-(4-oxo-2,3-dihydro-[1,5]benzothiazepin-5-yl)pentanamide;

N-[1(R)-(3-Aminopropylcarbamoyl)-2-((1H-indol-3-yl)ethyl]-4-(4-oxo-2,3-dihydro-[1,5]-benzothiazepin-5-yl)butyramide;

N-[1(R)-(3-Aminopropylcarbamoyl)-2-(5,6,7,8-tetrahydro-naphthalen-2-yl)ethyl]-4-(4-oxo-2,3-dihydro-[1,5]-benzothiazepin-5-yl)butyramide;

N-[1(R)-(3-Amino-2-hydroxypropylcarbamoyl)-2-(naphthalen-2-yl)ethyl]-3-(11-oxo-11H-dibenzo[b,f][1,4]oxazepin-10-yl)propionamide;

N-[1(R)-(3-Aminopropylcarbamoyl)-2-(naphthalen-2-yl)ethyl]-4-(1,4-dioxo-2,3-dihydro-[1,5]benzothiazepin-5-yl)butyramide;

N-[1(R)-(3-Aminopropylcarbamoyl)-2-(naphthalen-2-yl)ethyl]-4-(4-oxo-2,3-dihydro-[1,5]-benzoxazepin-5-yl)butyranmide;

N-[1(R)-(3-Amino-2-hydroxypropylcarbamoyl)-2-(naphthalen-2-yl)ethyl]-3-(2-methyl-4-oxo-2,3-dihydro-[1,5]benzothiazepin-5-yl)-propionamide;

N-[1(R)-(3-Aminopropylcarbamoyl)-2-(naphthalen-2-yl)ethyl]-3-(7-fluoro-4-oxo-[1,5]benzothiazepin-5-yl)propionamide;

N-[1(R)-(3-Amino-2-hydroxypropylcarbamoyl)-2-(naphthalen-2-yl)ethyl]-3-(5,11-dioxo-2,3-dihydro-1H,(11aS)-pyrrolo[2,1-c][1,4]diazepin-10-yl)propionamide;

N-[1(R)-(3-Amino-2-hydroxypropylcarbamoyl-2-(naphthalen-2-yl)ethyl]-3-(phenothiazin-10-yl)propionamide;

N-[1(R)-(3-Amino-2-hydroxypropylcarbamoyl)-2-(naphthalen-2-yl)ethyl]-4-(6-methoxy-2-oxo-2,3,4,5-tetrahydro-benzo[b]azepin-1-yl)butyramide;

N-[1(R)-(2-Aminoethylcarbamoyl)-2-(naphthalene-2-yl)ethyl]-3-(8-fluoro-4-oxo-2,3-dihydro-[1,5]benzothiazepin-5-yl)propionamide;

N-(3-Amino-2-hydroxypropyl)-3-(naphthalene-2-yl)-2(R)-[3-(4-oxo-7-trifluoromethyl-2,3-dihydro-[1,5]benzothiazepin-5-yl)propionylamino]propionamide;

N-[1(R)-(3-Amino-2-hydroxypropylcarbamoyl)-2-(naphthalen-2-yl)ethyl]-4-(4-oxo-2,3-dihydro-[1,5]-benzoxazepin-5-yl)butyramide;

N-(3-Amino-2-hydroxypropyl)-3-(naphthalen-2-yl)-2(R)-[3-(4-oxo-2,3-dihydro-[1,5]-benzoxazepin-5-y)propionylamino]propionamide;

N-[1(R)-(3-Amino-2-hydroxypropylcarbamoyl)-2-(naphthalen-2-yl)ethyl]-4-(8-fluoro-4-oxo-2,3-dihydro-[1,5]benzothiazepin-5-yl)butyramide;

N-(3-Amino-2-hydroxypropyl)-2(R)-[3-(8-fluoro-4-oxo-2,3-dihydro-[1,5]benzothiazepin-5-yl)propionylamino]-3-(naphthalen-2yl)propionamide;

N-[1(R)-(3-Aminopropylcarbamoyl)-2-(naphthalen-2-yl)ethyl]-4-(8-fluoro-4-oxo-[1,5]-benzothiazepin-5-yl)butyramide, N-[1(R)-(3-Aminopropylcarbamoyl)-2-(naphthalen-2-yl)ethyl]-3-(6-oxo-6,11-dihydro-dibenzo[b,e]azepin-5yl)propionamide;

N-[1(R)-(3-Amino-2-hydroxypropylcarbamoyl)-2-(naphthalen-2-yl)ethyl]-3-(6-oxo-6,11-dihydro-dibenzo[b,e]-azepin-5-yl)propionamide;

N-[1(R)-(2-Aminoethylcarbamoyl)-2-(naphthalen-2-yl)ethyl]-3-(6,11-dioxo-6,11-dihydro-dibenzo[b,e]azepin-5-yl)propionamide;

N-[1(R)-(3-Aminopropylcarbamoyl)-2-(naphthalen-2-yl)ethyl]-3-(6,11-dioxo-6,11-dihydro-dibenzo[b,e]azepin-5-yl)propionamide;

N-[1(R)-(3-Amino-2-hydroxypropylcarbamoyl)-2(naphthalen-2-yl)ethyl]-3-(6,11-dioxo-6,11-dihydro-dibenzo-[b,e]-azepin-5-yl)propionamide;

N-[1(R)-(3-Aminopropylcarbamoyl)-2-(naphthalen-2-yl)ethyl]-5-(6-oxo-6H-dibenzo [b,f]azocin-5-yl)pentanamide;

N-[1(R)-(3-Amino-2-hydroxypropylcarbamoyl)-2-(naphthalen-2-yl)ethyl]-5-(6-oxo-6H-dibenzo[b,f]azocin-5-yl)pentanamide;

N-[1(R)-(3-Amino-2-hydroxypropylcarbamoyl)-2-(naphthalen-2-yl)ethyl]-3-(11-oxo-11H-dibenzo[b,f][1,4]thiazepin-10-yl)propionamide;

N-[1(R)-(3-Amino-2-hydroxypropylcarbamoyl)-2-(naphthalen-2-yl)ethyl]-3-(11-oxo-11H-dibenzo[b,f][1,4]-thiazepin-10-yl)propionamide;

N-[1(R)-(3-Amino-2-hydroxypropylcarbamoyl)-2-(naphthalen-2-yl)ethyl]-5-(5,11-dioxo-5,11-dihydrodibenzo-[b,f][1,4]thiazepin-10-yl)pentanamide;

N-[1(R)-(3-Amino-2-hydroxypropylcarbamoyl)-2-(naphtbalen-2-yl)ethyl]-5-(5,5,11-trioxo-5,11-dihydro-dibenzo[b,f][1,4]thiazepin-10-yl)pentanamide;

N-[1(R)-(3-Amino-2-hydroxypropylcarbamoyl)-2-(naphthalen-2-yl)ethyl]-3-(2,2-dimethyl-4-oxo-3,4-dihydro-2H-benzo[1,5]thiazepin-5-yl)propionamide;

N-[1(R)-(3-Amino-2-hydroxypropylcarbamoyl)-2-(naphthalen-2-yl)ethyl]-3-(7-chloro-5,11-dioxo-2,3,11,11a-tetrahydro-1H,5H-benzo[e]pyrrolo[1,2a][1,4]diazepine-10-yl) propionamide;

N-1(R)-(3-Amino-2-hydroxypropylcarbamoyl)-2-(naphthalen-2-yl)ethyl]-3-(6,12-dioxo-6,6a,7,8,9,10-hexahydro-12H-benzo[e]pyrido[1,2-a][1,4]diazepine-5-yl)propionamide;

N-[1(R)-(3-Amino-2-hydroxypropylcarbamoyl)-2-(naphthalen-2-yl)ethyl]-3-(9-fluoro-2-oxo-3,4,5,6-tetrahydro-2H-benzo[b]azocin-1-yl)propionamide;

N-[1(R)-(3-Aminopropylcarbamoyl)-2-(naphthalen-2-yl)ethyl]-2-methyl-3-(4-oxo-3,4-dihydro-2H-benzo[1,5]-thiazepin-5-yl)propionamide;

N-1(R)-(3-Amino-2-hydroxypropylcarbamoyl)-2-(naphthalen-2-yl)ethyl]-2-methyl-3-(4-oxo-3,4-dihydro-2H-benzo[1,5]thiazepin-5-yl)propionamide;

N-[1(R)-(3-amino-2(S)-hydroxypropylcarbamoyl)-2-(naphthalen-2-yl)ethyl]-4-(4-oxo-3,4-dihydro-[1,5]-benzothiazepin-5-yl)butyramide;

N-[1(R)-(3-Amino-2-hydroxy-propylcarbamoyl)-2-(naphthalen-2-yl)ethyl]-2-methyl-3-(5,11-dioxo-2,3,11,11a-tetrahydro-1H,5H-benzo[e]pyrrolo[1,2a][1,4]diazepine-10-yl)propionamide;

N-[1(R)-(3-amino-2(R)-hydroxypropylcarbamoyl)-2-(naphthalen-2-yl)ethyl]-4-(4-oxo-3,4-dihydro-[1,5]-benzothiazepin-5-yl)buthanameide N-[1(R)-(3-Amino-2-hydroxy-propylcarbamoyl)-2-(naphthalen-2-yl)ethyl]-2,2-dimethyl-3-(5,11-dioxo-2,3,11,11a-tetrahydro-1H,5H-benzo[e]pyrrolo[1,2-a][1,4]diazepine-10-yl)propionamide;

N-[1(R)-(3-Amino-2-hydroxypropylcarbamoyl)-2-(naphthalen-2-yl)ethyl]-2,2-dimethyl-3-(1,1,4-trioxo-benzo-[1,5]thiazepin-5-yl)propionamide;

N-1(R)-(3-Aminomethylcarbamoyl)-2-(naphthalen-2-yl)ethyl]-2-methyl-3-(4-oxo-3,4-dihydro-[1,5]benzothiazepin-5-yl)propionamide;

N-[1(R)-(3-Amino -2-hydroxycarbamoyl)-2-(naphthalen-2-yl)ethyl]-3-(4-oxo-3,4-dihydro[1,5]benzothiazepin-5-yl)butyramide;

N-[1(R)-(3-Amino-2-hydroxycarbamoyl)-2-(naphthalen-2-yl)ethyl]-3-(3-cyano-5-isopropyl-2oxo-2H-cyclohepta-4,6,8-trieno[b]pyrrol-1-yl)propionamide;

N-[1(R)-(3-Amino-2-hydroxycarbamoyl)-2-(naphthalen-2-yl)ethyl]-3-(5,11-dioxo-2,3,11,11a-tetrahydro-1H,5H-benzo[e]pyrrolo[1,2-a][1,4]diazepin-10-yl)propionamide and N-[1(R)-[2-Hydroxy-3-(2-(R)-hydroxypropylamino)propylcarbamoyl]-2-(naphthalen-2-yl)ethyl]-4-(4-oxo-2,3-dihydro-[1,5]benzothiazepin-5-yl)butyramide.

The compounds of the instant invention all have at least one asymmetric centers as noted by the a sterisk in the structural Formula I a. Additional asymmetric centers may be present on the molecule depending on the nature of the various substituents on the molecule.

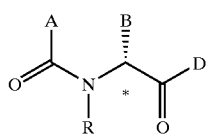

Ia

As consequence of these chiral centers, the compounds of the present invention occur as racemates, mixtures of enantiomers and as individual enantiomers, as well as diastereomers and mixtures of diastereomers. Each such asymmetric center will produce two optical isomers and it is intended that all such optical isomers, as separated, pure or partially purified optical isomers or racemic mixtures thereof, be included within the ambit of the instant invention.

The term "R" and "S" are used herein as commonly used in organic chemistry to donate specific configuration of a chiral center. The term "R" (rectus) refers to that configuration of a chiral center with a clockwise relationship of group priorities (highest to second lowest) when viewed along the bond toward the lowest priorities group. The term "S" (sinsister) refers to that configuration of a chiral center with a counterclockwise relationship of a group priorities (highest to second lowest) when viewed along the bond toward the lowest priority group. The prioity of groups is based on their atomic number (in order of decreasing atomic number).

In the case of the asymmetric center represented by the asterisk in Formula I a, it has been found that the compound in which the B substituent is below the plane of the structure, as seen in Formula I a, is more active and thus more preferred over the compound in which the B substituent is above the plane of the structure.

This invention encompasses the pharmaceutically acceptable salts of the compounds defined by Formula I. A compound of this invention can possess a sufficiently acidic, a sufficient basic, or both functional groups, and accordingly react with any of a number of organic or inorganic acids, and organic or inorganic bases, to form a pharmaceutically acceptable salts. The term "pharmaceutically acceptable salts" as used herein, refers to salts of the compounds of above Formula I which are substantially non-toxic to live organism. Typically pharmaceutically acceptable salts include those salts prepared by reaction of the compounds of the present invention with pharmaceutically acceptable mineral or organic acid or an organic or inorganic base. Such salts are acid addition and base addition.

The instant compounds are generally isolated in the form of their pharmaceutically acceptable acid addition salts, such as the salts derived from using inorganic and organic acids. Examples of such inorganic acids include hydrochloric acid, hydrobromic acid, hydroiodic acid, nitric acid, sulfuric acid, phosphoric acid, and the like. Examples of such organic acids include acetic acid, trifluroacetic acid, propionic acid, maleic acid, succinic acid, maleic acid, oxalic acid, methanesulfonic acid, p-toluenesulfonic acid, and the like. Preferred pharmaceutically acceptable acid addition salts are those formed with mineral acids such as hydrochloric acid and hydrobromic acid, and those formed with organic acids as methanesulfonic acid, trifluroacetic acid, maleic acid.

The instant compounds are also generally isolated in the form of their pharmaceutically acceptable base addition salts, such as salts derived from using inorganic and organic bases. Such bases useful in preparing the salts of this invention thus include sodium hydroxide, potassium hydroxide, ammonium hydroxide, potassium carbonate, sodium carbonate, sodium bicarbonate, potassium bicarbonate, calcium carbonate, and the like. The sodium and potassium salts are particularly preferred.

It should be recognized that the particular couterion forming a part of any salt of this invention is usually not of a critical nature, so long as the salt as a whole is pharmaceutically acceptable and as long as the couterion does not contribute undesired qualities to the salt as a whole.

This invention further encompasses the pharmaceutically acceptable solvates of the compounds of Formula I. Most compounds of the Formula I can be combined with solvents such a s water, methanol, ethanol, and acetonitrile to form pharmaceutically acceptable solvates such as corresponding hydrate, metanolate, ethanolate, and acetonitrilate.

Throughout the instant application the following abbreviations are used with the following meanings:

BOC: t-butoxycarbonyl
BOP: benzotriazole-1-yloxy-tris-(dimethylamino)-phosphoniumhexafluorophosphiate CBZ: benzyloxycarbonyl
DCC: dicyclohexyl carbodiimide
DMF: N,N-dimethylformamide
EDC: 1-(3-dimethylaminopropyl)-3-ethylcarbodiimide hydrochloride
FAB-MASS: FAB Mass Spectrum
Fmoc: 9-fluorenylmeththyloxycarbonyl
HOBt: 1-hydroxybenzotriazole
MHz: Megaherz
NMM :N-Methylmorpholine
NMR: Nuclear Magnetic Resonance
Ser: Serine
Nal: Naphthylalanine
TFA: trifluoroacetic acid The preparation of compounds of Formula I of the present invention may be carried out in sequential or convergent synthetic routes. Syntheses detailing the preparation of the compounds of Formula I in a sequential manner are presented in the following Schemes 1,2, and 3.

The compounds having a Formula I are prepared from intermediates such as 1.

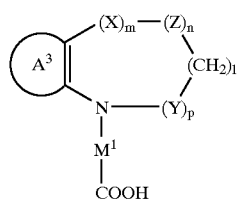

Typical itermediates 3 may be synthesized as shown in Scheme 1. Ester derivatives 2 are, in some cases, commercially available or are prepared by a number of methods well known in the art. Coupling of intermediate 1 with ester derivative 2 is carried out by standard peptide coupling reaction conditions using an acid activating agent such as EDC, DCC, and BOP in an inert solvent such as dichloromethane or DMF, with or without the presence of a catalyst such as HOBt. The skills required in carrying out the reaction and purification of the resulting reaction products are known to those in the art. Purification procedure includes crystallization, and/or chromatography.

Scheme 1

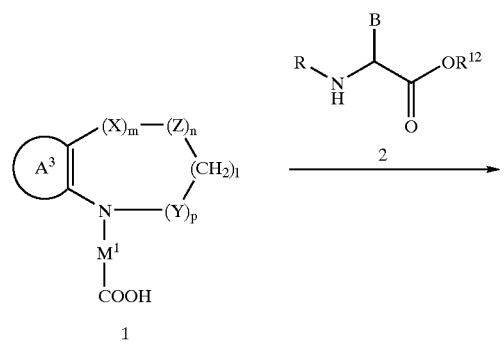

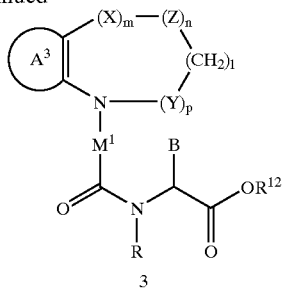

Conversion of typical itermediates 3 to intermediate acids 4 may be accomplished by a number of methods known in the art described in Scheme 2; for example, methyl and ethyl esters can be hydrolyzed with sodium hydroxide, potassium hydroxide, or lithium hydroxide in a protic solvent like aqueous methanol, ethanol, dioxane. In addition, removal f benzyl ester can be achieved by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane, t-Butyl ester can be removed with acid like hydrogen chloride, TFA in a various solvents including dioxane and dichloromethane.

Scheme 2

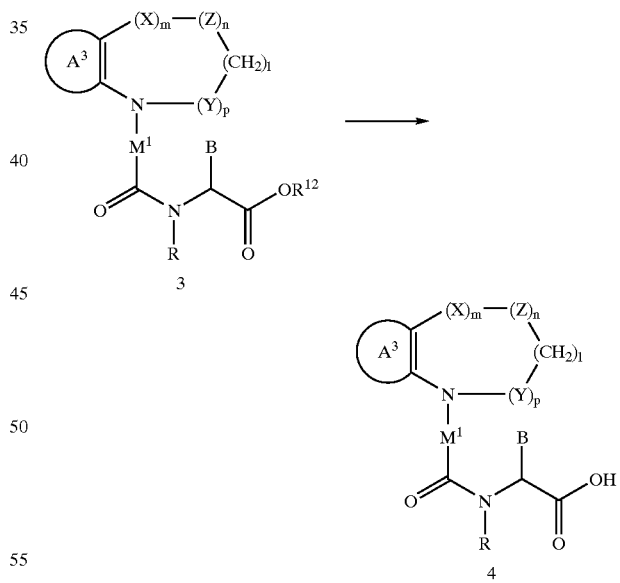

Diammo derivatives 5,6 are either commercially available or can be synthesized by routine methods. Compounds of Formula I and intermediates 7 are synthesized in following Scheme 3. Coupling a carboxylic acid 4 with an amine 5 or 6 is carried out using acid activating agent such as EDC, DCC, and BOP in a solvent such as dichloromethane or DMF with or without the presence of such as HOBt. Purification

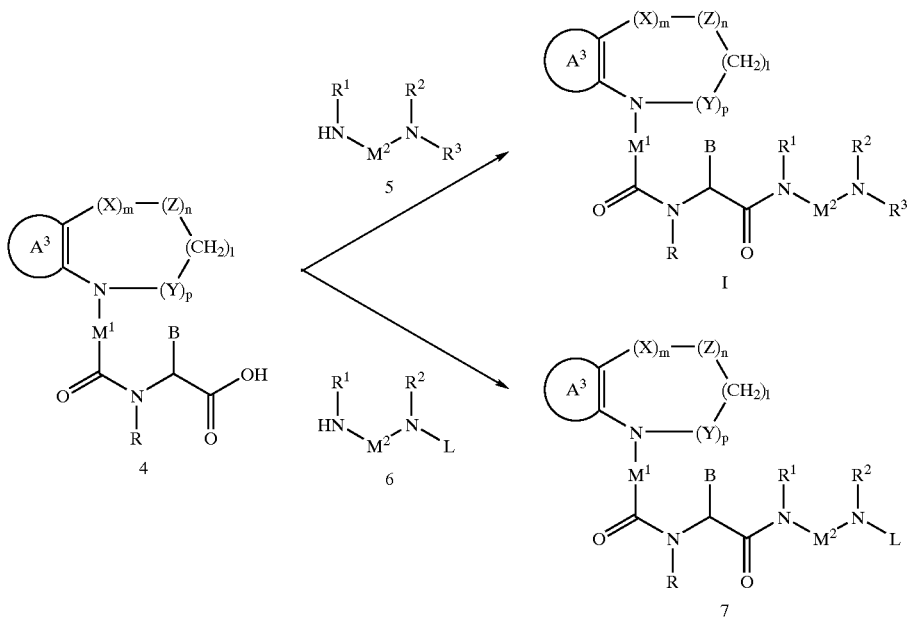

L = protective group of the resulting reaction products are known to those in the art. Purification procedure includes crystallization, and/or chromatography using as a crrier like a silica gel.

The preparation of compounds of Formula I and intermediate 7 may also be carried out in convergent synthetic route illustrated in Scheme 4,5,6,7. The protected amino acid derivatives 8 are, in some cases, commercially available, where the protecting $L^1$ is, for example, BOG or CBZ or Fmoc groups Other protected amino acid derivatives 8 can be prepared by a number of methods well known in the literature Intermediate 9 or 10 are prepared by coupling of protecting amino acids derivatives 8 with diamino derivatives 5 or 6 number of methods known in the art; for example, catalytic hydrogenation with hydrogen in the presence of a novel metal or its oxide such as palladium on activated cabon in a protic solvent such as ethanol. In the cases where catalytic hydrogenation is contraindicated by the presence of other potentially reactive fuctionality, removal of CBZ groups can also be achieved by treatment with a solution of hydrogen bromide in acetic acid, or by treatment with a mixture of TFA and disethylsulfide. Removal of BOC protecting groups is carried out in a solvent such as ethyl acetate or dioxane or methylene chloride or methanol, with a strong acids, such as TFA or hydrochloric acid or hydrogen chloride gas. Removal of Fmoc groups is carried out with a orgic base Scheme 4

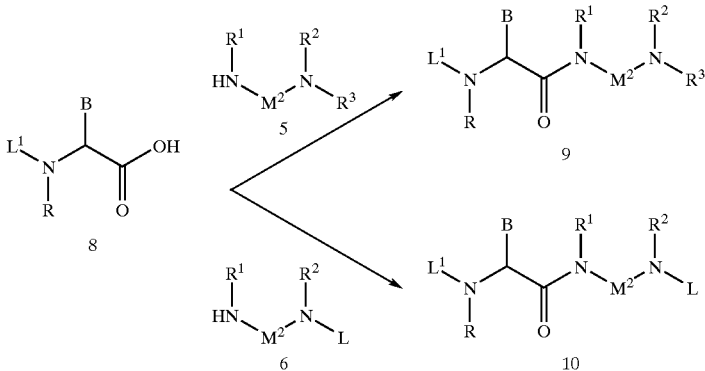

$L^1$ = protective group

Conversion of 9, 10 to intermediate 11, 12 can be achieved as shown in Scheme 5 by removal of the protecting group $L^1$(CBZ, BOC, Fmoc, Formyl, Phthaloyl, etc.). CBZ and BOC are used extensively in the synthesis, and their removal conditions are known to those skilled in the art. For example, removal of CBZ groups can be carried out by a such as dimethylaine or piperazine Removal of f rmyl groups is carried out in a solvent such as water or methnol wvith a acid such as hydrochloric acid or hydrazine-acetic acid. Deprotection of phthaloyl groups is achieved in a solvent such as methanol or ethanol or dioxane with hydrazine. Conditions required to remove other protecting groups which may be present and can be found in Green, T. and Wuts, P. G. M., Protective Group in Organic Synthesis, John Wiley & Sons, Inc., New York, N.Y. 1991. It should be recognized that L is different from $L^1$ and is stable to the removal conditions of $L^1$. For example, when $L^1$ is CBZ or Fmoc, BOC as L is preferred.

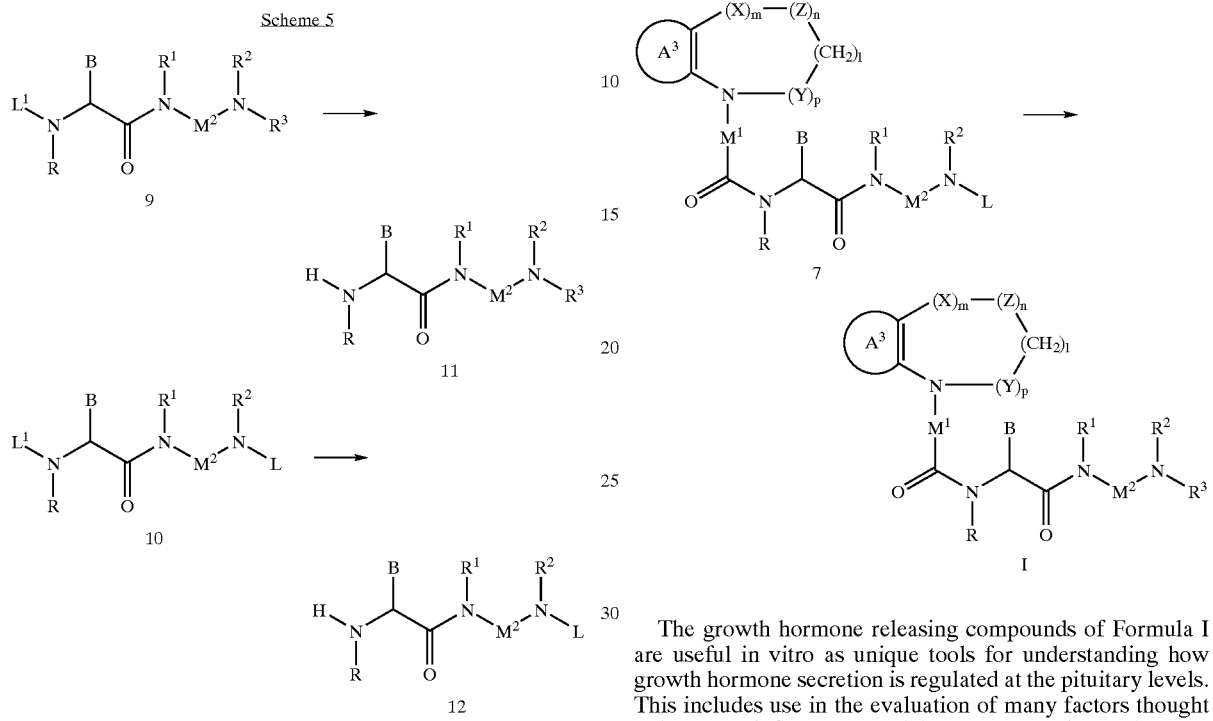

Compouds of Formula I in present invention and intermediates 7 are synthesized as shown in Scheme 6. Coupling a carboxyhc acid 1 with an amine 11 or 12 is achieved using a condition described above.

Conversion of itermediates 7 to compounds of Formula I may be accomplished as illustrated in Scheme 7. Removal of protecting group L may be carried out by various conditions described above.

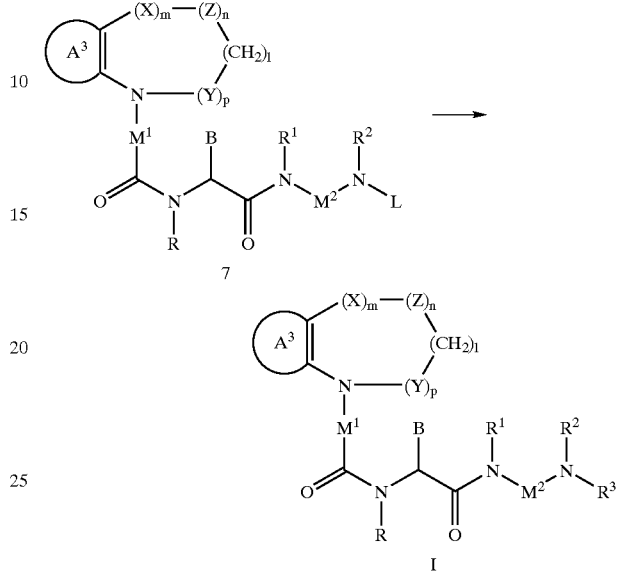

The growth hormone releasing compounds of Formula I are useful in vitro as unique tools for understanding how growth hormone secretion is regulated at the pituitary levels. This includes use in the evaluation of many factors thought or known to influence growth hormone secretion such as age sex, nutritional factors, glucose, amino acids, fatty acids, as well as fasting and non-fasting states. In addition, the compounds of this invention can be used in the evaluation of how other hormones modify growth hormone releasing activity. For example, it has already been established that

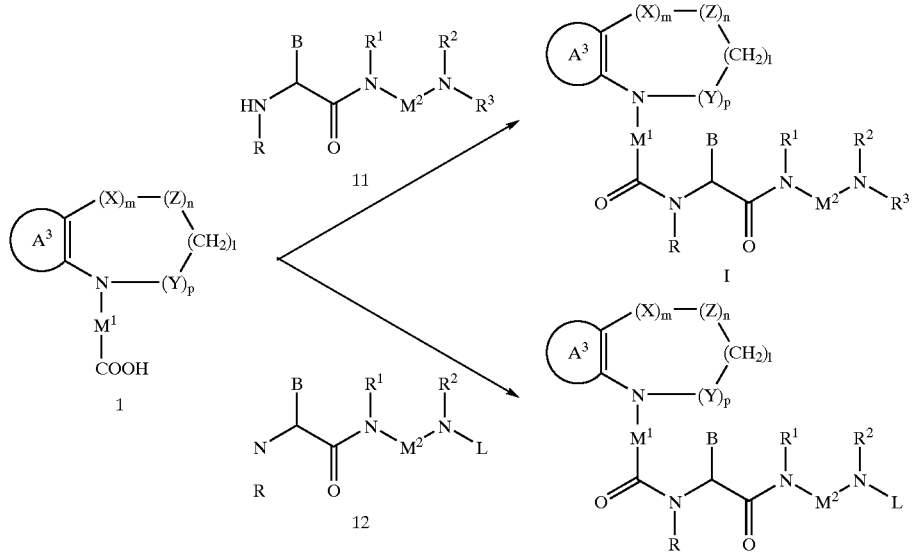

somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of the Formula I can also be employed to investigate the possible negative or positive feedback effects of some the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, sheep,cow and the like to accelerate and increase their rate and extent of growth, to improve feed efficiency and to increase milk production in such animals. In addition, these compounds can be administered to humans in vivo as a diagnostic tool to directly determine whether the hypothalamus-pituitary system is capable of releasing growth hormone. For example, the compounds of Formula I can be administered to humans. Serum samples taken before and after such administration can be assayed for growth hormone. Comparison of the amounts of growth hormone in each of these samples would be a means for directly determining the ability of the patient's hypothalamus-pituitary system to release growth hormone.

Accordingly, the present invention includes within its scope pharmaceutical comprising, as an active ingredient, at least one of the compounds of Formula I in association with a pharmaceutical carrier or diluent. Optionally, the active ingredient of the pharmaceutical composition can comprise an anabolic agent in addition to at least one of the compounds of Formula I or another composition which exhibits a different activity, an antibiotic growth permittant or an agent to treat osteoporosis or in combination with a corticosteroid to minimized the catabolic side effects or with other pharmaceutically active materials wherein the combination enhances efficiency and minimizes side effects.

Growth promoting and anabolic agents include, but are not limited to, THR, diethylstibesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. No. 4,411,890 and publications WO 89/07110, WO89/07111 and B-HT920 as well as hexarelin and GHRP-2 as described in WO 93/04081 or growth hormone releasing hormone (GHRH also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing facor, IGF-1, or IGF-2. For example, a compound of the present invention may be used in combination with IGF-1 for the treatment or prevention of obesity. In addition, a compounds of this invention may be employed in conjunction with retinoic acid to improve the conditon of musculature and skin that results from intrinsic agents.

The present invention is further directed to a method for the manufacture of a medicament for stimulating the release of growth hormone in humans and animals comprising combining a compound of the prsent invention with a pharmaceutical carrieror diluent.

As is well known to those skilled in the art, the known and potential uses of growth hormone are varied and multitudinous. Thus, the administration of the compounds of this invention for purpose of stimulation the release of endogenous growth hormone can have the same effects or uses as growth hormone iself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuopathies; replacement of growth hormone in stressed patients; treatment of osteochondrodysplasias, Noonans syndrome, sleep disorders, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndrome; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosupprssed patients and to enhanced antibody response following vaccination; increasing the total lymphocyte count of a human, in particular, increasing the T4/T8-cell ratio in a human with a depressed T4/T-8-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis in the frail elderly; stimulation of osteoblasts, bone remodeling, and cartilage growth; treatment of male and female infertility; stimulation of the immune system in companion animals and treatment of disorders of aging in companion animals; growth promotant in livestok; and stimulation of wool growth in sheep. Further, the instant compounds are useful for increasing feed efficiency, promoting growth, increasing milk production and improving the carcass quality of livestock. Likewise, the instant compounds are usefully in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of; osteoporosis; catabolic illness; immune deficiency, including that in individuals with a depressed T4/T8-cell ratio; hip fracture; musculoskeletal impairment in the elderly; growth hormone deficiency in adults or in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illness induced or facilitated by corticotropin releasing factor or stress- and anxiety-related disorders, including stress-induced depression, and headache, abdominal bowel syndrome, immune suppression, HIV infections. Alzheimer's disease, gastrointestinal disease, anorexia nervosa, hemorrhagic stress, drug and alchol withdrawal symptons, drug addiction, and fertility problems.

It will be known to those skilles in the art that there are numerous compounds now being used in an effort to treat the diseases or therapeutic indications enumerated above. Combinations of these therapeutic agents some of which have also been mentioned above with the growth hormone secretagogues of this invention will bring additional complementary, and often synergistic properties to enhance the growth promotant, anabolic and desirable properties of these various therapeutic agents. In these combinations, the therapeutic agents and the growth hormone secretagogues of this invention may independently present in dose rages from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" Trends in Endocrinol. Metab., 4,19–25(1993). Bisphosphonates with these utilities include alendronate, tiludronate, diethyl-APD, risedronate, etidronate, YM-175, clodronate, pamidronate, and BM-210995. Accordingly to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Combined therapy to enhance the healing of bone fractures, wounds or burns can be illustrated by combinations of growth factors, especially bFGF (basic fibroblast growth factor), and the growth hormone secretagogues of this invention(Canalis, E. Clin. Orthop., 1985, 193, 246–263; Kawaguchi, H. Endocrinology, 1994, 135, 774–781; Nakamura, T. et al., Endocrinology, 1995,136, 1276–1284: Shida, J. et al., Journal of Orthopaedic Research, 1996, 14,265–272).

Combined therapy to enhance the healing of bone fractures, wounds or burns can also be illustrated by combinations of growth factors, especially PDGF(platelet-derived growth factor), and the growth hormone secretagogues of this invention (Stile, C. D. et al., Proc. Natl. Acad. Sci. USA, 1979, 76, 1279–1283; Chen, Y. et al., J. Cell Physiol., 1989, 140, 59 67).

Osteoporosis and other bone disorders may also be treated with compounds of this invention in combination with calcitonin, estrogen, raloxifene and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and staozolol.

Other uses of the instant compounds will be apparent from the following references;

Amato, et al., Journal of Clinical Endocrinology and Metabolism 77(6):1671–1676 (1993),
Bengtsson, et al., Journal of Clinical Endocrinology and Metabolism 76(2):309–317 (1993),
Binnerts, et al., Clinical Endocrinology 37;79–87(1992);
Bowers, et al., Journal of Clinical Endocrinology and Metabolism 76(4):817–823(1993),
Cuneo, et al., Journal of Applied Physiology 70(2):688–694 (199 1),
Cuneo, et al., Journal of Applied Physiology 70(2):695–700 (1991),
Degerblad, et al., Acta Endocrinologica 126:387–393(1992),
Eden, et al., Arteriosclerosis and Thrombosis 13829:296–301(1993),
Hartman, et al., Horm Research 40:37–47(1993),
Ho, et al., Horm Research 40:80–86(1993),
Jogensen, et al., Acta Endocrinologica 125:449–453(1991),
Jogensen, et al., The Lancet June 3:1221–1224(1989),
Lambert, et al., Clinical Endocrinology 37:111–115(1992),
McGauley, et al., Horm Research 33:52–54(1990),
Moller,et al., Clinical Endocrinology 39:403–408(1993),
O'Halloran, et al., Journal of Clinical Endocrinology and Metabolism 76(5):1344–1348 (1993),
Orme, et al., Clinical Endocrinology 37:453–459(1992),
Rodriguez-Amao, et al., Horm Research 39:87–88(1993),
Rosen, et al., Clinical Endocrinology 40:111–116(L994),
Rosen, et al., Acta Endocrinologica 129:195–200(1993),
Rudman, et al., The New England Journal of Medicine 323(1): 1–6(1990),
Salmon, et al., The New England Journal of Medicine 321(26):1797–1803(1989),
Shibasaki, et al., Journal of Clinical Endocrinology and Metabolism 58(1):212–214 (1984),
Sompsen, et al., Acta Paediatr Scand [Suppec]379:139–146 (1991),
Tauber, et al., Journal of Clinical Endocrinology and Metabolism 76(5):1135–1139 (1993).
Vandeweghe, et al., Clinical Endocrinology 39;409–415 (1993),
Whitehead, et al., Clinical Endocrinology 36:45–52(1992),
Bercu, et al., U.S. Pat. No. 5,246.920.

Additionally, the most potent compounds of this invention can be used as GH antagonists. It is known that hypothalamic hormones that are super agoniats can also used as antagonists. For example super agonists of Gonadotropin Releasing Hormone (GnRH) such as Gonadorelin and Leuprolide act either as agonists or antagonists depending on the method of administration. The action of the GnRH super agonists are summarized in Goodman and Gilmans, The Pharmacological Basis of Theraperfics, $8^{th}$ E D., McGraw Hill Inc. p. 1353(1993). By analogy, it is believed the continuous administration of the compounds of formula I will lead to down-regulation of the growth response. These molecules can therefore be used as functional antagonists of pituitary GH secretion, thereby antagonizing GH or IGF-1.

The uses of such antagonists of CH secretion include but are not limited to; treatment of excess GH secretion as in acromegaly or gigantism; in cancer of the breast, colon and prostate; in diabetes especially in Type I adolescent patients to counteract the dawn phenomenon; and Type I and Type II patients to directly control blood glucose, and to control the long-term affects of diabetes, as for example in retinopathy.

The compounds of this invention can be administered by oral, parenteral (e.g., intramuscular, intraperitoneal, intravenous or subcutaneous injection or infusion, or implant), nasal, pulmonary, vaginal, rectal, sublingual, or topical routes of administration and can be formulated in dosage forms appropriate for each route of administration.

Accordingly, the present invention includes within its scope for pharmaceutical composition comprising, as active ingredient, at least one or the compounds of Formula I in association with a pharmaceutical acceptable carrier. Optionally, the active ingredient of the pharmaceutical compositions can comprise an anabolic agent in addition to at least one of the compounds of formula I or another composition which exhibits a different activity, e.g., an antibiotic growth permittant or an agent to treat osteoporosis or in combination with a corticosteroid to minimize the catabolic side effects or with a growth factor such as bFGF (basic fibroblast growth factor) for treatment of patients recovering from major surgery, bone fractures, wounds, burns or with other pharmaceutically active materials wherein the combination enhances efficacy and minimizes side effects.

The compounds of this invention can be administered by oral, parenteal (e.g., intraperitonial, intramuscular, intravenous, or subcutaneous injection, or implant), nasal, vaginal, rectal, sublingual, or other topical routes of administration and can be formulated with phamaceutically acceptable carries to provide appropriate dosage forms for each route of administration.

Solid dosage forms for oral administration include capsules, tablets, pills, powders and granules. In such solids dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tables and pills can additionally be prepared with enteric coatings.

Liquid dosage forms for oral administration include pharmaceutically acceptable emulsion, solutions, suspensions, syrups, the elixirs coating inert diluents commonly used in the art, such as water. Besides such inert diluents, compositions can also include adjuvants, such as wetting agents, emulsifying and suspending agents, sweetening, flavoring, and perfuming agents.

Preparations according to this invention for parenteral administration include sterile aqueous or non aqueous solutions, suspensions, or emulsions. Examples of non-aqueous solvent or vehicles are propylene glycol, Composition for nasal or sublingual administration are also prepared with standard excipients well known in the art.

The dosage of active ingredient in the compositions of this invention may be varied, however, it is necessary that the amount of the active ingredient be such that a suitable dosage form is obtained. The selected dosage depends upon the desired therapeutic effects, on the route of administration, and on the duration of the treatment. Generally, dosage levels of between 0.0001 to 100 mg/kg of body weight daily are administered to patients and animals, e.g., to obtain effective release of GH.

A preferred dosage range is 0.01 to 10.0 mg/kg of boy weight daily.

EXAMPLES

Example 1

Sequential Method

N-[1(R)-(3-Aminopropylcarbamoyl)-2-(naphthalen-2-yl) ethyl]-3-(4-oxo-2,3-dihydro-[1,5]-benzothiazepin-5-yl) propionamide hydrochloride Step 1

[3-(2(R)-Amino-3-naphthalen-2-yl-propionylamino)propyl] carbamic acid, tert-butyl ester To DMF(15 ml) solution of CBZ-D-Nal-OH(1.1 g) and N-(3-Aminopropyl) carbamic acid tert-butyl ester (500 mg), HOBt(530 mg), EDC(720 mg) were added under cooling on ice-water and then stirring was continued at room temperature overnight. The reaction mixture was poured into saturated sodium hydrogen carbonate solution (150 ml), formed precipitate was collected by filtration and then dried to give white powder (1.43 g). Obtained white powder (1.43 g) in DMF (15 ml) is hydrogenated with 10% Pd—C(400 mg) at 35° C., 4.3 atm. for 4 days. After removal of catalyst by filtration, filtrate was evaporated to dryness and then crystallized from n-hexane:ethyl acetate. The crystal was collected and then dried to afford 640 mg of product.

$^1$HMR (270 MHz, CDCl$_3$)δ: 1.34(2H,s), 1.43(9H,s), 1.59 (2H,m), 2.90(1H,dd), 3.05(2H,q), 3.32(2H,q), 3.41(1H,dd), 3.70(1H,bs), 5.02(1H,bs), 7.38(1H,d), 4.40–7.55(3H,m), 7.66(1H,s), 7.75–7.85(3H,m)

FAB-MSS: m/z 370(M+H)$^+$

Step 2

N-[1(R)-3-Aminopropylcarbamoyl)-2-(naphthalen-2-yl) ethyl]-3-(4-oxo-2,3dihydro-[1,5]-benzothiazepin-5-yl) propionamide hydrochloride To DMF (2 ml) solution of 3-(4oxo-2,3-dihydro-[1,5]-benzothiazepin-5-yl)-propionic acid(100 mg) and [3-(2(R)-Amino-3-naphthalen-2-yl-propionylamino)-propyl]-carbamic acid, t-butyl ester(134 mg), EDC(90 mg) and HOBt (66 mg ) were added under cooling on ice-water and then stirring was continued at room temperature overnight. The reaction mixture was poured into saturated sodium hydrogen carbonate solution (20 ml), formed precipitate was collected by filtration and then dried to give white powder (217 mg). After obtained white powder (80 mg) was dissolved in ethyl acetate (2 ml) under cooling on ice-water 4N hydrogen chloride/ethyl acetate solution was added and then stirring is continued at room temperature for three hours. The reaction mixture was concentrated under reduced pressure. Ether was added to the oily residue. Solidified oily residue was collected by filtration and then dried to give 69 mg of product.

$^1$H-NMR(270 MHz, DMSO-d$_6$)δ: 1.30–1.65(2H,m n), 2.00–2.20(2H,m), 2.20–2.45(2H,m), 2.70–3.00(3H,m), 3.00–3.60(6H,m), 3.98(1H,bs), 4.51(1H,m), 7.25(1H,t), 7.35–7.65(6H,m), 7.66–8.05(6H,m). 8.17(1H,d), 8.25(1H,t)

FAB-MSS: m/z 505(M+H)$^+$

Compounds of Example 2~147,164~166,169,171,174, 175,177,179,187~190, 193~196,199~273 were synthesized by using similar method of Example 1.

Compounds of Example 34~37,40~45,102~103,112, 136~137,177 were free base and NMR were measured in CDCl$_3$.

Compounds of Example 2~33,38~39,46~101,104~111, 113~135,138~147,164,176, 179,187~190,193~196, 199~273 were hydrochloride salts and NMR were measured in DMSO-d$_6$.

Example 148

Convergent Method
N-[1(R)-(2-Amino-ethylcarbamoyl)-2-benzyloxyethyl]-3-(4-oxo-2,3-dihydro-1.5-benzothiazepin-5-yl)propionamide hydrochloride Step 1

3-Benzyloxy-2-[3-(4-oxo-2,3-dihydro-1,5benzothiazepin-5-yl)propionylamino]propionic acid methyl ester To DMF(2 ml) solution of D-Ser(Bzl)—OMe hydrochloride(141 mg) and 3-(4-oxo-2,3-dihydro-1,5-benzothiazepin-5-yl)-propionic acid(138 mg), N-methyl morpholine(61 mg), HOBt (92 mg) and EDC (125 mg) were added under cooling on ice-water and then stirring is continued at room temperature overnight. After reaction, reaction mixture was poured into saturated sodium hydrogen carbonate solution (20 ml) and then extracted with ethyl acetate. Ethyl acetate layer was dried on anhydrous sodium sulfate and then evaporated to dryness. Title compound (270 mg) was isolated by using silica get chromatography (CHCl$_3$MeOH=100:1).

$^1$H-NMR(270 MHz, CDCl$_3$)δ: 2.35–2.60(3H,m), 2.65–2.80(1H,m), 3.20–3.40(1H, m), 3.45–3.90(3H,m), 3.71(3H,s), 4.49(3H,m), 4.64(1H,d), 6.56(1H,d), 7.15–7.50 (8H,m), 7.59(1H,d)

FAB-MSS: m/z 443(M+H)$^{30}$

Step 2

N-[1(R)-(2-Amino-ethylcarbamoyl)-2-benzyloxyethyl]-3-(4-oxo-2,3-dihydro-1,5-benzothiazepin-5-yl) propionamide hydrochloride To amethylalcohol solution (5 ml) of 3-Benzyloxy-2-[3-(4-oxo-2,3-dihydro-1,5-benzothiazepin-5-yl) propionylamino]propionic acid methyl ester (260 mg), 1N sodium hydroxy solution (0.62 ml) was added under cooling on ice-water and the stirring was continued for 3 hours. Reaction mixture is adjusted to pH 2 with 1N hydrochloric acid and then evaporated to dryness. To residue, water is added, extracted with ethyl acetate and then dried on anhydrous sodium sulfate. Ethyl acetate was removed by evaporation to give oily residue (210 mg). To DMF solution of above oily residue and N-(2-aminoethyl)carbamic acid tert-butyl ester (79 mg), HOBt (92 mg) and EDC (120 mg) were added under cooling on ice-water and then stirring was continued at room temperature overnight. Reaction mixture was poured into saturated sodium hydrogen carbonate solution (40 ml), formed precipitate was collected by filtration and then dissolved in ethyl acetate, dried on anhydrous sodium sulfate. After removal ethyl acetate by evaporation, white powder (180 mg) was isolated by using silica gel chromatography (CHCL$_3$:MeOH=100:1). Hydrogen chloride salt of desired product was prepared as following way. To ethyl acetate solution (2 ml) of obtained white powder (70 mg), 4N hydrogen chloride ethyl acetate-solution (2 ml) was added under cooling on ice-water and then stirring was continued at room temperature for 3 hours. After removal of solvent by evaporation, ether was added to oily residue. Solidified oily residue was collected by filtration and then dried to give 48 mg of product.

$^1$H-NMR (270 MHz, DMSO-d$_6$)δ: 2.20–2.65(4H,m), 2.70–2.90(2H,m), 3.20–3.75(7H,m), 4.15–4.55(4H,m), 7.20–7.40(6H,m), 7.50–7.75(3H,m), 7.95(2H,bs), 8.10–8.25 (2H,m)

FAB-MSS; m/z 471(M+H)$^+$

Compounds of Example 149~163, 167,168,170,172,173, 176,178, 180~186, 191, 192,197,198 were synthesized by using similar method of example 148.

Compounds of Example 168,180 were free base and NMR were measured in CDCl$_3$.

Compounds of Example 149~163, 167,170,172,173,176, 178, 181~186, 191, 192, 197,198 were hydrochloride salts and NMR were measured in DMSO-d$_6$.

Test Example

Compounds of Formula I were evaluated in vitro for their efficacy and potency to release growth hormone (GH) in primary rat anterior pituitary cells. Preparation of rat primary anterior pituitary cells were be essentially same as described previously (Chen et al., Endocrinology, 1989, 124, 2791–2798 and Chen et al., Endocrinology, 1991, 129, 3337–3342). Briefly, Rats were killed by decapitation. The pituitary was quickly removed. The anterior pituitaries were digested with 0.2% collagnase, 0.2% hyaluronidase and 200 U/ml DNase I in Hank's balanced salt solution. The cells were resuspended in Dulbecco's Modified Eagle's medium containing 7.5% horse serum 5.0% fetal calf serum, 1% nonessential amino acids, 100 U/ml penicillin and 100 μg/ml streptomycin and adjusted to 1.0×10$^5$ cells/ml. 0.5 ml of this suspension was placed in each well of 48-well trays and left for 3 days before release experiments were performed.

On day of the experiments, cells were washed twice with the above medium containing 20 mM HEPES, pH 7.4. Growth hormone release was initiated by addition of medium containing 20 mM HEPES and test compound. Incubation was carried out for 15 minutes at 3.7° C. After incubation, GH release into the medium was measured by a standard radioimmunoassay (RIA) procedure.

Compounds of Example number 1,9,10,14,15,19,64,68, 79,94,96,107,112, 115,121, 126, 129,134,135,140,144,145, 159,160,164,165,181,182,200,205,206,212,216,236,241, 242,244,249,252, 253,254,255,257,258,259,262,263,264 have shown growth hormone (GH) releasing activity below 10$^{-8}$ M.

Evaluation of GH-releasing activity by oral administration in rats were carried out as follows.

Male Sprague-Dawley rats (4 weeks old, n=6 per group) were fasted overnight and test compounds (10 mg/kg) were orally administered. Thirty minutes after the administration the rats were decapitated and the trunk blood was collected in a heparin-containing tube. After centrifugation, the plasma was stored at −20° C. before the GH assay by RIA as described above. Plasma GH values were converted into logarithms and the analysis of variance (ANOVA) was performed. The significance of the difference was examined by the LSD method.

Compound of Example number 165,206,253,257,259, 262,264 have shown plasma GH value above 10 ng/ml.

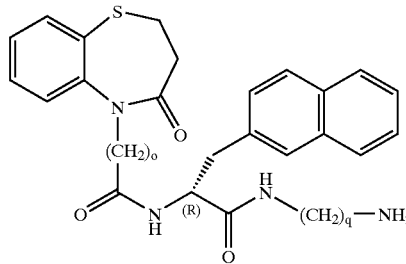

| Example number | o | q | $^1$H-NMR ($\delta$ ppm): | FAB-MS $(M + H)^+$ |
|---|---|---|---|---|
| 2 | 1 | 2 | 2.30–2.45(2H, m), 2.80–3.50(8H, m), 3.55–4.10(1H, m), 4.68(2H, bs), 7.17(1H, bs), 7.40–7.60(5H, m), 7.65–8.10 (7H, m), 8.30–8.50(2H, m) | 477 |
| 3 | 1 | 3 | 1.60–1.80(2H, m), 2.30–2.55(2H, m), 2.60–4.20(9H, m), 4.66(2H, bs), 7.16(1H, bs), 7.35–7.60(6H, m), 7.65–8.00 (7H, m), 8.25(1H, bs), 8.41(1H, bs) | 491 |
| 4 | 1 | 4 | 1.30–1.65(4H, m), 2.30–2.55(2H, m), 2.60–2.80(2H, m), 2.90–4.15(7H, m), 4.50–4.80(2H, m), 7.16(1H, bs), 7.35–7.6(5H, m), 7.65–8.00(7H, m), 8.16(1H, bs), 8.40(1H, bs) | 505 |
| 5 | 2 | 2 | 2.05–2.45(3H, m), 2.75–3.00(3H, m), 3.10–3.65(6H, m), 3.90–4.25(1H, m), 4.50(1H, dd), 7.26(1H, t), 7.35–7.55 (5H, m),7.58(1H, d), 7.69(1H, s), 7.75–7.95(3H, m), 8.07(2H, bs), 8.25–8.40(2H, m) | 491 |
| 6 | 2 | 4 | 1.30–1.55(4H, m), 2.00–2.55(4H, m), 2.60–2.75(2H, m), 2.80–4.30(8H, m), 4.49(1H, dd), 7.26(1H, t), 7.30–7.65 (5H, m), 7.65–7.90(7H, m), 8.03(1H, t), 8.24(1H, d) | 519 |
| 7 | 2 | 5 | 1.10–1.40(4H, m), 1.40–1.60(2H, m), 2.00–3.65(13H, m), 3.90–4.25(1H, m), 4.48(1H, dd), 7.26(1H, t), 7.30–7.55 (5H, m), 7.58(1H, d), 7.67(1H, d), 7.70–8.00(6H, m), 8.22(1H, d) | 533 |
| 8 | 2 | 6 | 1.00–1.60(8H, m), 2.00–3.65(13H, m), 3.90–4.25(1H, m), 4.48(1H, dd), 7.15–8.00(14H, m), 8.21(1H, d) | 547 |
| 9 | 3 | 2 | 1.30–1.65(2H, m), 2.00–2.20(2H, m), 2.20–2.45(2H, m), 2.70–3.00(3H, m), 3.00–3.60(6H, m), 3.98(1H, bs), 4.51 (1H, dd), 7.25(1H, t), 7.35–7.65(6H, m), 7.65–8.05(6H, m), 8.17(1H, d), 8.25(1H, t) | 505 |
| 10 | 3 | 3 | 1.30–1.75(4H, m), 2.00–2.15(2H, m), 2.20–2.45(2H, m), 2.60–2.80(2H, m), 2.89(1H, dd), 3.05–3.45(6H, m), 3.95 (1H, bs), 4.50(1H, dd), 7.28(1H, t), 7.30–7.65(6H, m), 7.65–7.95(6H, m), 8.10–8.20(2H, m) | 519 |
| 11 | 3 | 4 | 1.30–1.70(6H, m), 1.95–2.15(2H, m), 2.20–2.50(2H, m), 2.60–2.80(2H, m), 2.80–3.45(7H, m), 3.85–4.10(1H, m), 4.52(1H, dd), 7.24(1H, t), 7.30–7.55(5H, m), 7.58(1H, d), 7.65–7.95(6H, m), 8.00–8.20(2H, m) | 533 |
| 12 | 3 | 5 | 1.10–1.65(8H, m), 1.95–2.15(2H, m), 2.20–2.45(2H, m), 2.55–2.80(2H, m), 2.85–3.50(7H, m), 3.80–4.10(1H, m), 4.40–4.60(1H, m), 7.24(1H, t), 7.30–7.50(5H, m), 7.58(1H, d), 7.65–7.90(6H, m), 7.95(1H, t), 8.09(1H, d) | 547 |
| 13 | 3 | 6 | 1.00–1.60(10H, m), 1.95–2.15(2H, m), 2.20–2.50(2H, m), 2.60–2.85(2H, m), 2.85–3.55(7H, m), 3.80–4.10(1H, m), 4.51(1H, dd), 7.15–8.00(14H, m), 8.08(1H, d) | 561 |
| 14 | 4 | 2 | 1.05–1.40(4H, m), 1.85–2.10(2H, m), 2.20–2.45(2H, m), 2.70–3.00(3H, m), 3.05–3.40(4H, m), 3.50–3.80(2H, m), 3.85–4.10(1H, m), 4.52(1H, dd), 7.25(1H, s), 7.30–7.65(6H, m), 7.65–8.00(6H, m), 8.10(1H, d), 8.21(1H, t) | 519 |
| 15 | 4 | 3 | 1.00–1.50(4H, m), 1.55–1.80(2H, m), 1.90–2.10(2H, m), 2.25–2.45(2H, m), 2.60–2.80(2H, m), 2.91(1H, dd), 3.00–3.50(6H, m), 3.85–4.10(1H, m), 4.51(1H, dd), 7.25(1H, t), 7.30–7.65(6H, m), 7.65–7.95(5H, m), 8.00–8.25 (2H, m) | 533 |

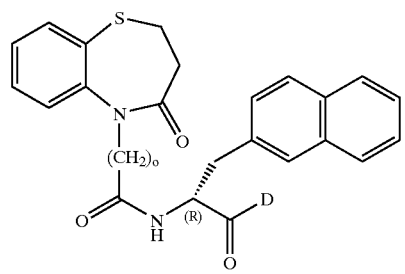

| Example number | o | D | $^1$H-NMR ($\delta$ ppm): | FAB-MS $(M + H)^+$ |
|---|---|---|---|---|
| 16 | 1 | —N(H)—CH₂CH₂—NHCH₃ | 2.35–2.60(5H, m), 3.85–3.10(3H, m), 3.10–3.50(5H, m), 3.55–4.05(1H, m), 4.70 (2H, bs), 7.16(1H, bs), 7.40–7.60(5H, m), 7.65–7.95(5H, m), 8.20–8.55(2H, m), 8.80 (2H, bs) | 491 |
| 17 | 2 | —N(H)—CH₂CH₂—NHCH₃ | 2.00–2.65(7H, m), 2.75–3.00(3H, m), 3.10–3.60(6H, m), 3.90–4.25(1H, m), 4.49(1H, dd), 7.27(1H, t), 7.30–7.65(6H, m), 7.65–7.90(4H, m), 8.20–8.35(1H, m), 8.75(2H, bs) | 505 |
| 18 | 1 | —N(H)—CH₂CH₂CH₂—NHCH₃ | 1.60–1.80(2H, m), 2.35–2.60(5H, m), 2.70–3.45(8H, m), 3.45–4.20(1H, m), 4.65(2H, bs), 7.15(1H, bs), 7.40–7.60(5H, m), 7.72(1H, s), 7.75–7.95(4H, m), 8.25(1H, bs), 8.42(1H, bs), 8.63(2H, bs) | 505 |
| 19 | 2 | —N(H)—CH₂CH₂CH₂—NHCH₃ | 1.55–1.75(2H, m), 2.00–2.65(7H, m), 2.65–2.80(2H, m), 2.89(1H, dd), 3.00–3.60(6H, m), 3.95–4.40(1H, m), 4.46(1H, dd), 7.26(1H, t), 7.35–7.65(6H, m), 7.65–7.90(4H, m), 8.15(1H, t), 8.28(1H, d), 8.59(2H, bs) | 519 |

-continued

| | | | | |
|---|---|---|---|---|
| 20 | 3 | —NH—CH2CH2CH2—NHCH3 | 1.30–1.85(4H, m), 1.95–2.20(2H, m), 2.20–3.00(7H, m), 3.00–3.70(6H, m), 4.00(1H, bs), 4.49(1H, bs), 7.15–8.00(11H, m), 8.17(2H, bs), 8.56(2H, bs) | 533 |
| 21 | 1 | —NH—C(CH3)2—CH2NH2 | 1.25(6H, s), 2.35–2.50(2H, m), 2.85–3.45(6H, m), 3.55–4.20(1H, m), 4.71(2H, bs), 7.27(1H, t), 7.35–7.60(6H, m), 7.65–8.10(7H, m), 8.36(1H, d) | 505 |
| 22 | 2 | —NH—C(CH3)2—CH2NH2 | 1.15(6H, s), 2.05–2.60(4H, m), 2.80–3.00(2H, m), 3.05–3.80(5H, m), 3.95–4.40(1H, bs), 4.49(1H, dd), 7.20–7.30(1H, m), 7.35–7.60(6H, m), 7.65–8.00(7H, m), 8.26(1H, d) | 519 |
| 23 | 2 | —NH—CH2—C(CH3)2—CH2NH2 | 0.75(3H, s), 0.80(3H, s), 2.00–2.65(6H, m), 2.85–3.00(3H, m), 3.00–3.60(4H, m), 4.10(1H, bs), 4.53(1H, dd), 7.26(1H, t), 7.35–7.60(6H, m), 7.65–7.90(6H, m), 8.25–8.45(2H, m) | 533 |
| 24 | 3 | —NH—CH2—C(CH3)2—CH2NH2 | 0.75(3H, s), 0.80(3H, s), 1.30–1.70(2H, m), 2.00–2.20(2H, m), 2.20–2.60(4H, m), 2.85–3.05(3H, m), 3.05–3.50(4H, m), 3.90–4.10(1H, m), 4.55(1H, dd), 7.24(1H, t), 7.35–7.56(6H, m), 7.65–7.95(6H, m), 8.19(1H, d), 8.36(1H, t) | 547 |
| 25 | 2 | —N(CH3)—CH2CH2CH2—NH2 / CH2CH2—NH2 | 1.55(2H, m), 2.00–2.60(4H, m), 2.60–4.30(14H, m), 4.85(1H, dd), 7.28(1H, t), 7.35–7.55(5H, m), 7.60(1H, d), 7.65–8.20(9H, m) | 548 |
| 26 | 3 | —N(CH3)—CH2CH2CH2—NH2 / CH2CH2—NH2 | 1.30–1.90(4H, m), 2.00–2.15(2H, m), 2.20–2.50(2H, m), 2.50–4.15(14H, m), 4.86(1H, dd), 7.25(1H, t), 7.30–7.55(4H, m), 7.59(1H, d), 7.65–8.20(9H, m) | 562 |
| 27 | 2 | —N(CH3)—CH2CH2CH2—NH2 / CH2CH2CH2—NH2 | 1.60–1.95(4H, m), 2.00–2.55(4H, m), 2.60–2.85(3H, m), 2.85–3.60(10H, m), 3.95–4.25(1H, m), 4.85(1H, dd), 7.28(1H, t), 7.35–7.55(5H, m), 7.60(1H, d), 7.65–8.10(6H, m), 8.50(1H, d) | 562 |
| 28 | 3 | —N(CH3)—CH2CH2CH2—NH2 / CH2CH2CH2—NH2 | 1.30–1.65(2H, m), 1.65–1.95(4H, m), 2.00–2.15(2H, m), 2.20–2.50(2H, m), 2.60–2.85(3H, m), 2.85–3.45(10H, m), 3.99(1H, bs), 4.87(1H, dd), 7.25(1H, t), 7.35–7.55(5H, m), 7.59(1H, d), 7.70–8.10(6H, m), 8.37(1H, d) | 576 |
| 29 | 2 | —NH—CH2—CH=CH—CH2—NH2 (cis) | 2.00–2.60(4H, m), 2.89(1H, dd), 3.05–3.60(6H, m), 3.65–3.80(2H, m), 3.90–4.25(1H, m), 4.50(1H, dd), 5.45–5.60(2H, m), 7.24(1H, t), 7.35–7.55(5H, m), 7.58(1H, d), 7.67(1H, s), 7.75–7.90(3H, m), 8.01(2H, bs), 8.20–8.35(2H, m) | 517 |
| 30 | 3 | —NH—CH2—CH=CH—CH2—NH2 (cis) | 1.30–1.60(2H, m), 1.95–2.15(2H, m), 2.20–2.50(2H, m), 2.90(1H, dd), 3.05–3.60(6H, m), 3.05–4.10(3H, m), 4.51(1H, dd), 5.40–5.65(2H, m), 7.24(1H, t), 7.30–7.50(5H, m), 7.58(1H, d), 7.65–8.05(6H, m), 8.12(1H, d), 8.27(1H, t) | 531 |
| 31 | 2 | 1-methyl-4-aminopiperidinyl | 1.20–1.50(2H, m), 1.75–1.95(2H, m), 2.00–2.60(4H, m), 2.75–3.60(8H, m), 3.90–4.40(3H, bs), 4.97(1H, dd), 7.20–7.90(11H, m), 8.00–8.20(2H, m), 8.41(1H, dd) | 531 |

-continued
| | | | | |
|---|---|---|---|---|
| 32 | 2 | 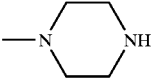 | 2.10–2.65(4H, m), 2.80–3.80(13H, m), 4.10(1H, bs), 4.95(1H, dd), 7.27(1H, t), 7.35–7.65(6H, m), 7.65–7.85(4H, m) | 517 |
| 33 | 2 | 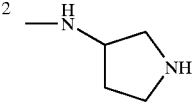 | 1.50–1.90(2H, m), 1.90–2.70(6H, m), 2.75–3.00(2H, m), 3.00–3.60(5H, m), 3.90–4.35(2H, m), 4.48(1H, dd), 7.20–7.90(11H, m), 8.20–8.50(2H, m), 9.12(1H, bs) | 517 |
| 34 | 1 | 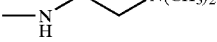 | 1.70–2.65(10H, m), 3.05–3.50(6H, m), 4.05–4.40(1H, m), 4.45–4.70(1H, m), 4.75–4.95(1H, m), 7.05–7.90(13H, m) | 505 |
| 35 | 2 | 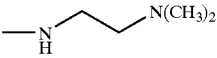 | 1.85(6H, s), 1.90–2.05(1H, m), 2.10–2.20(1H, m), 2.30–2.75(4H, m), 3.00–3.40(6H, m), 3.60–3.80(1H, m), 4.40–4.65(2H, m), 7.15–7.50(6H, m), 7.55–7.70(2H, m), 7.70–7.85(3H, m) | 519 |
| 36 | 2 | 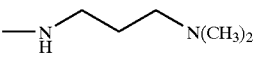 | 1.40–1.65(2H, m), 1.90–2.80(12H, m), 3.00–3.40(6H, m), 3.55–3.80(1H, m), 4.35–4.65(2H, m), 6.60–6.80(1H, m), 7.05–7.85(12H, m) | 533 |
| 37 | 3 | 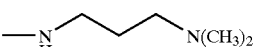 | 1.35–1.95(4H, m), 2.05–2.70(10H, m), 2.85–3.60(9H, m), 3.95–4.45(1H, m), 4.60–4.80(1H, m), 7.00–7.90(13H, m) | 547 |
| 38 | 1 | 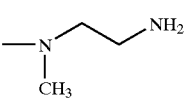 | 1.45(2H, bs), 2.15–2.80(7H, m), 3.05–3.50(6H, m), 4.00–4.95(3H, m), 7.05–7.85(11H, m) | 491 |
| 39 | 2 | 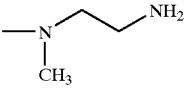 | 1.35(2H, bs), 2.10(2H, d), 2.30–2.75(7H, m), 2.95–3.45(6H, m), 3.55–3.80(1H, m), 4.40–4.70(2H, m), 7.15–7.50(6H, m), 7.5–7.85(5H, m) | 505 |
| 40 | 1 | 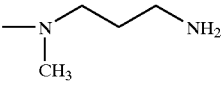 | 1.35–1.75(4H, m), 2.30–3.50(13H, m), 4.15–4.75(2H, m), 5.10–5.40(1H, m), 7.10–7.90(12H, m) | 505 |
| 41 | 2 | 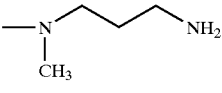 | 1.20–1.75(4H, m), 2.25–2.75(9H, m), 2.90–3.45(6H, m), 3.60–3.80(1H, m), 4.40–4.60(1H, m), 5.05–5.25(1H, m), 6.70–6.90(1H, m), 7.15–7.50(6H, m), 7.50–7.85(5H, m) | 519 |
| 42 | 3 | 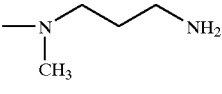 | 1.30–2.75(14H, m), 2.75–3.55(8H, m), 4.20–4.55(1H, m), 5.10–5.35(1H, m), 6.85–7.5(7H, m), 7.55–7.90(5H, m) | 533 |
| 43 | 1 | 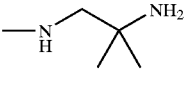 | 0.90(3H, s), 1.05(3H, s), 2.25–2.65(4H, m), 2.95–3.50(6H, m), 4.05–4.60(2H, m), 4.75–5.00(1H, m), 7.00–7.85(13H, m) | 505 |
| 44 | 2 |  | 0.85(3H, s), 0.90(3H, s), 1.85(2H, bs), 2.30–2.70(4H, m), 2.95–3.40(6H, m), 3.55–3.75(1H, m), 4.35–4.60(1H, m), 4.65–4.80(1H, dd), 7.15–7.50(6H, m), 7.55(1H, d), 7.65–7.85(4H, m) | 519 |
| 45 | 2 | 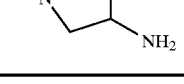 | 1.05–1.55(4H, m), 2.35–2.80(5H, m), 2.90–2.85(9H, m), 4.45–4.65(1H, m), 4.75–4.95(1H, m), 6.80–6.95(1H, m), 7.15–8.50(11H, m) | 517 |

-continued

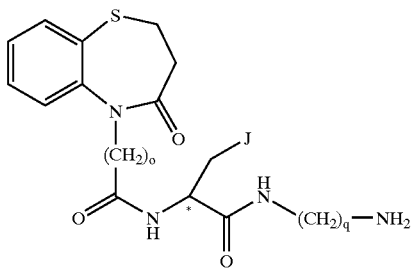

| Example number | o | q | * | J | ¹H-NMR (δ ppm): | FAB-MS (M + H)⁺ |
|---|---|---|---|---|---|---|
| 46 | 1 | 2 | (S) | naphthalen-2-ylmethyl | 2.35–2.45(2H, m), 2.80–3.50(8H, m), 3.55–4.10(1H, m), 4.69(1H, bs), 7.16(1H, bs), 7.40–7.60(5H, m), 7.65–8.10(7H, m), 8.30–8.50(2H, m) | 477 |
| 47 | 2 | 2 | (S) | naphthalen-2-ylmethyl | 2.05–2.60(4H, m), 2.70–2.95(3H, m), 3.10–3.60(6H, m), 3.85–4.25(1H, m), 4.47(1H, dd), 7.26(1H, t), 7.30–7.50(5H, m), 7.58(1H, d), 7.60–8.00(6H, m), 8.15–8.35(2H, m) | 491 |
| 48 | 2 | 3 | (S) | naphthalen-2-ylmethyl | 1.55–1.75(2H, m), 2.00–2.95(7H, m), 3.00–3.65(6H, m), 3.90–4.35(1H, m), 4.46(1H, dd), 7.20–7.65(7H, m), 7.65–7.95(6H, m), 8.15(1H, t), 8.27(1H, d) | 505 |
| 49 | 3 | 3 | (S) | naphthalen-2-ylmethyl | 1.30–1.75(4H, m), 1.90–2.15(2H, m), 2.20–2.45(2H, m), 2.65–2.80(2H, m), 2.91(1H, dd), 3.00–3.55(6H, m), 3.85–4.10(1H, m), 4.49(1H, dd), 7.15–7.65(7H, m), 7.65–7.95(6H, m), 8.05–8.25(2H, m) | 519 |
| 50 | 1 | 2 | (R) | benzyl | 2.35–2.55(2H, m), 2.75–2.95(3H, m), 3.09(1H, dd), 3.20–3.50(4H, m), 3.55–4.15(1H, m), 4.56(2H, bs), 7.15–7.35(7H, m), 7.35–7.45(1H, m), 7.58(1H, d), 7.99(2H, bs), 8.20–8.45(2H, m) | 427 |
| 51 | 2 | 2 | (R) | benzyl | 2.10–2.45(4H, m), 2.65–2.85(3H, m), 2.85–3.85(6H, m), 4.10(1H, bs), 4.38(1H, dd), 7.10–7.35(6H, m), 7.40–7.65(3H, m), 8.10–8.25(2H, m) | 441 |
| 52 | 1 | 2 | (S) | benzyl | 2.35–2.50(2H, m), 2.70–2.95(3H, m), 3.09(1H, dd), 3.15–3.50(4H, m), 3.60–4.10(2H, m), 4.57(2H, bs), 7.15–7.30(7H, m), 7.35–7.45(1H, m), 7.59(1H, d), 7.97(2H, bs), 8.20–8.45(2H, m) | 427 |
| 53 | 2 | 2 | (S) | benzyl | 2.10–2.45(4H, m), 2.65–2.85(3H, m), 2.85–3.85(6H, m), 4.10(1H, bs), 4.38(1H, dd), 7.10–7.35(6H, m), 7.40–7.65(3H, m), 8.10–8.25(2H, m) | 441 |
| 54 | 3 | 2 | (S) | benzyl | 1.35–1.65(2H, m), 1.95–2.20(2H, m), 2.25–2.50(2H, m), 2.70–2.90(3H, m), 3.02(1H, dd), 3.85–4.15(1H, m), 4.40(1H, d), 7.05–7.30(6H, m), 7.35–7.55(2H, m), 7.61(1H, d), 7.86(2H, bs), 8.05–8.25(2H, m) | 455 |
| 55 | 2 | 2 | (R) | 1H-indol-3-ylmethyl | 2.05–2.60(4H, m), 2.75–2.95(3H, m), 3.00–3.70(6H, m), 4.15(1H, bs), 4.39(1H, dd), 6.90–7.15(3H, m), 7.25–7.35(2H, m), 7.45–7.65(4H, m), 7.88(2H, bs), 8.05–8.20(2H, m), 10.80(1H, s) | 480 |

| | | | | | |
|---|---|---|---|---|---|
| 56 | 2 | 3 | (R) | 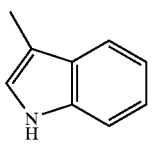 | 1.55–1.70(2H, m), 2.00–2.60(4H, m), 2.60–2.75(2H, m), 2.87(1H, dd), 2.95–3.15(3H, m), 3.15–3.65(3H, m), 3.95–4.30(1H, m), 4.37(1H, dd), 6.85–7.10(3H, m), 7.20–7.35(2H, m), 7.40–7.65(4H, m), 7.82(2H, bs), 8.00–8.20(2H, m), 10.80(1H, s) | 494 |
| 57 | 3 | 2 | (R) | 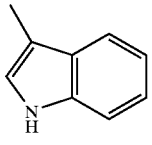 | 1.35–1.70(2H, m), 2.00–2.25(2H, m), 2.25–2.50(2H, m), 2.70–3.00(3H, m), 3.00–3.60(6H, m), 3.90–4.20(1H, m), 4.42(1H, dd), 6.90–7.15(3H, m), 7.20–7.65(6H, m), 7.75–8.10(3H, m), 8.16(1H, t), 10.80(1H, s) | 494 |
| 58 | 3 | 3 | (R) | 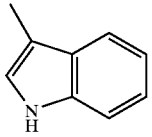 | 1.35–1.75(4H, m), 2.05–2.20(2H, m), 2.30–2.45(2H, m), 2.60–2.80(2H, m), 2.91(1H, dd), 3.00–3.15(3H, m), 3.15–3.55(3H, m), 3.95–4.15(1H, m), 4.36(1H, dd), 6.90–7.15(3H, m), 7.20–7.65(6H, m), 7.80(2H, bs), 8.01(1H, d), 8.11(1H, t), 10.81(1H, s) | 508 |
| 59 | 1 | 2 | (S) | 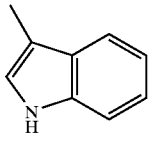 | 2.35–2.45(2H, m), 2.70–3.50(8H, m), 3.60–4.20(1H, m), 4.58(2H, bs), 6.90–7.45(7H, m), 7.57(2H, t), 7.98(3H, bs), 8.20–8.40(2H, m), 10.86(1H, s) | 466 |
| 60 | 2 | 3 | (R) | 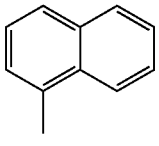 | 1.55–1.75(2H, m), 2.00–2.80(6H, m), 3.00–3.70(7H, m), 3.90–4.30(1H, m), 4.49(1H, dd), 7.20–7.65(9H, m), 7.70–8.00(4H, m), 8.05–8.25(2H, m), 8.25–8.40(1H, m) | 505 |
| 61 | 3 | 3 | (R) | 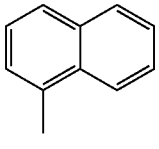 | 1.30–1.75(4H, m), 1.95–2.20(2H, m), 2.25–2.50(2H, m), 2.60–2.80(2H, m), 3.05–3.80(7H, m), 3.90–4.10(1H, m), 4.51(1H, dd), 7.20–7.65(9H, m), 7.65–8.00(4H, m), 8.05–8.25(3H, m) | 519 |
| 62 | 3 | 3 | (R) | 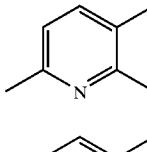 | 1.35–1.55(2H, m), 1.65–1.80(2H, m), 2.00–2.20(2H, m), 2.25–2.45 (2H, m), 3.10–3.50(6H, m), 3.67(1H, dd), 3.80–4.10(1H, m), 4.81(1H, dd), 7.25 (1H, t), 7.35–7.50(1H, m), 7.58(1H, d), 7.75–8.10(6H, m), 8.15–8.45(4H, m), 8.75–8.95(1H, m) | 520 |
| 63 | 2 | 3 | (R) | 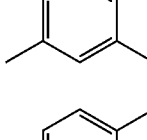 | 1.60–1.75(6H, m), 2.10–2.90(12H, m), 3.05–3.35(4H, m), 3.40–3.65 (1H, m), 3.95–4.10(1H, m), 4.10–4.35(2H, m), 6.85(3H, d), 7.25–7.30(1H, m), 7.45–7.50(2H, m), 7.60(1H, d), 7.80(3H, bs), 8.05(1H, t), 8.15(1H, d) | 509 |
| 64 | 3 | 3 | (R) | 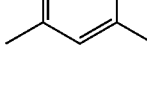 | 1.45–1.80(10H, m), 2.15(2H, bs), 2.45(2H, bs), 2.65–3.00(8H, m), 3.15–3.25(2H, m), 3.25–3.40(1H, m), 4.10(1H, bs), 4.35–4.45(1H, m), 6.95 (3H, bs), 7.35(2H, t), 7.55(2H, bs), 7.70(1H, d), 7.98(2H, bs), 8.15(1H, d), 8.25(1H, t) | 523 |
| 65 | 2 | 3 | (RS) | 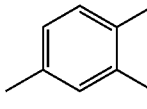 | 1.55–1.70(2H, m), 2.10–2.50(4H, m), 2.65–2.85(4H, m), 2.95–3.15(4H, m), 3.30–3.40(1H, m), 4.00–4.10(1H, m), 4.35–4.45(1H, m), 7.00–7.05 (2H, m), 7.20–7.30(2H, m), 7.35–7.65(6H, m), 7.80(3H, bs), 8.10(1H, t), 8.25(1H, d), 9.50(1H, bs) | 521 |
| 66 | 3 | 3 | (RS) | 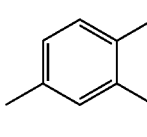 | 1.40–1.55(2H, m), 1.60–1.70(2H, m), 2.00–2.10(2H, m), 2.00–2.10(2H, m), 2.25–2.40(2H, m), 2.65–2.90(4H, m), 3.00–3.15(4H, m), 3.35–3.45 (1H, m), 3.90–4.00(1H, m), 4.35–4.45(1H, m), 7.00–7.05 (2H, m), 7.20–7.25(2H, m), 7.45(1H, bs), 7.50–7.65(4H, m), 7.75(3H, bs), 8.05–8.15(2H, m), 9.50(1H, bs) | 535 |

-continued

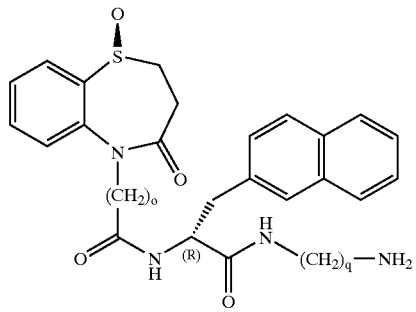

| Example number | o | q | ¹H-NMR (δ ppm): | FAB-MS (M + H)⁺ |
|---|---|---|---|---|
| 67 | 3 | 2 | 1.30–1.55(2H, m), 1.95–2.15(2H, m), 2.25–2.45(2H, m), 2.75–3.00(3H, m), 3.10–3.45(3H, m), 3.50–4.25 (4H, m), 4.52(1H, dd), 7.30–8.10(13H, m), 8.10–8.35(2H, m) | 521 |
| 68 | 3 | 3 | 1.30–1.55(2H, m), 1.55–1.75(2H, m), 1.95–2.10(2H, m), 2.25–2.45(2H, m), 2.60–2.80(2H, m), 2.85–3.25 (4H, m), 3.25–4.20(4H, m), 4.49(1H, dd), 7.30–7.95(13H, m), 8.05–8.25(2H, m) | 535 |

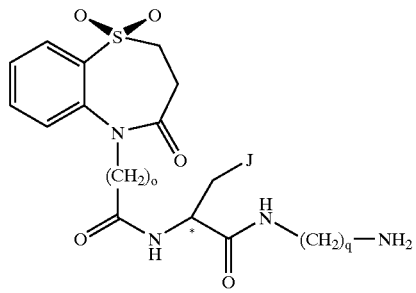

| Example number | o | q | * | J | ¹H-NMR (δ ppm): | FAB-MS (M + H)⁺ |
|---|---|---|---|---|---|---|
| 69 | 1 | 2 | (R) | 2-naphthylmethyl | 2.35–2.70(2H, m), 2.80–4.20(9H, m), 4.50–4.85(2H, m), 7.10–8.15(13H, m), 8.25–8.50(1H, m), 8.60(1H, d) | 509 |
| 70 | 2 | 2 | (R) | 2-naphthylmethyl | 2.05–2.60(4H, m), 2.70–3.00(3H, m), 3.00–4.20(7H, m), 4.49(1H, dd), 7.35–7.60(7H, m), 7.60–7.95(6H, m), 8.31(2H, bs) | 523 |
| 71 | 3 | 2 | (R) | 2-naphthylmethyl | 1.35–1.70(2H, m), 2.00–2.10(2H, m), 2.45–2.55(2H, m), 2.65–3.00(3H, m), 3.05–3.50 (5H, m), 3.60–3.90(2H, m), 4.53(1H, dd), 7.35–7.55(5H, m), 7.65–8.00(8H, m), 8.17 (1H, d), 8.26(1H, t) | 537 |
| 72 | 3 | 3 | (R) | 2-naphthylmethyl | 1.30–1.80(4H, m), 1.95–2.15(2H, m), 2.40–2.60(2H, m), 2.60–2.80(2H, m), 2.91(1H, dd), 3.00–3.20(4H, m), 3.45–3.95(3H, m), 4.51(1H, dd), 7.30–7.55(5H, m), 7.65–7.95 (8H, m), 8.05–8.25(2H, m) | 551 |
| 73 | 1 | 2 | (R) | benzyl | 2.35–2.55(1H, m), 2.55–2.65(1H, m), 2.70–2.95(3H, m), 3.11(1H, dd), 3.10–3.45(3H, m), 3.50–4.15(2H, m), 4.25–4.85(2H, m), 7.27(6H, s), 7.50–7.65(1H, m), 7.75(1H, t), 7.90(1H, d), 7.98(2H, bs), 8.26(1H, bs), 8.52(1H, d) | 459 |
| 74 | 2 | 2 | (R) | benzyl | 2.05–2.60(4H, m), 2.70–2.85(2H, m), 3.02(1H, dd), 3.10–3.45(3H, m), 3.55–4.25(3H, m), 4.38(1H, dd), 7.10–7.30(5H, m), 7.56(1H, t), 7.67(1H, d), 7.80–8.10(4H, m), 8.15–8.30(2H, m) | 473 |
| 75 | 1 | 2 | (S) | benzyl | 2.35–2.55(1H, m), 2.55–2.70(1H, m), 2.70–2.95(3H, m), 3.12(1H, dd), 3.20–3.45(3H, m), 3.50–4.20(2H, m), 4.25–4.85(2H, m), 7.27(6H, s), 7.45–7.60(1H, m), 7.75(1H, t), 7.89 (1H, d), 7.96(2H, bs), 8.26(1H, bs), 8.53(1H, d) | 459 |

-continued

| | | | | | |
|---|---|---|---|---|---|
| 76 | 2 | 2 | (S) | ![benzyl] | 2.05–2.60(4H, m), 2.70–2.85(2H, m), 3.02(1H, dd), 3.10–3.45(3H, m), 3.55–4.25(3H, m), 4.38(1H, dd), 7.10–7.30(5H, m), 7.56(1H, t), 7.67(1H, d), 7.80–8.10(4H, m), 8.15–8.30 (2H, m) | 473 |
| 77 | 3 | 2 | (S) | ![benzyl] | 1.40–1.75(2H, m), 1.95–2.15(2H, m), 2.30–2.60(2H, m), 2.70–2.90(3H, m), 3.00(1H, dd), 3.15–4.30(6H, m), 4.40(1H, dd), 7.05–7.25(5H, m), 7.45–7.80(3H, m), 7.80–8.00 (3H, m), 8.05–8.25(2H, m) | 487 |
| 78 | 3 | 3 | (R) | ![indolyl-methyl] | 1.45–1.75(4H, m), 2.00–2.15(2H, m), 2.40–2.60(2H, m), 2.60–2.75(2H, m), 2.89(1H, dd), 3.00–3.15(3H, m), 3.25–3.95(4H, m), 4.41(1H, dd), 6.90–7.15(3H, m), 7.31(1H, d), 7.45–7.60(3H, m), 7.65–7.95(4H, m), 8.01(1H, d), 8.10(1H, t), 10.80(1H, s) | 540 |

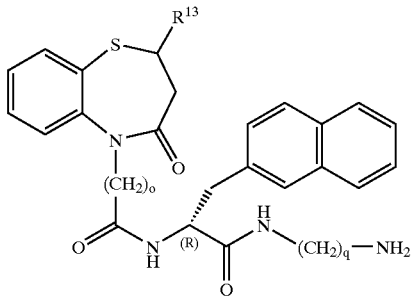

| Example number | o | q | R¹³ | ¹H-NMR (δ ppm): | FAB-MS (M + H)⁺ |
|---|---|---|---|---|---|
| 79 | 2 | 3 | CH₃ | 1.15(2H, d), 1.35(1H, d), 1.65(2H, t) 1.80–2.30(2H, m), 2.48(2H, m), 2.71(2H, t), 2.90(1H, m), 3.12 (3H, m), 3.25–4.30(3H, m), 4.45(1H, m), 7.20–7.60(7H, m), 7.65–8.00(6H, m), 8.15(1H, m), 8.27 (1H, m) | 519 |
| 80 | 3 | 2 | CH₃ | 1.17(2H, m), 1.25–1.60(3H, m), 1.85–2.25(3H, m), 2.45(1H, m), 2.60–3.05(3H, m), 3.05–3.45(3H, m), 3.60–4.10(3H, m), 4.52(1H, m), 7.00–7.60(7H, m), 7.65–7.90(4H, m), 8.00–8.30(3H, m), 8.34 (1H, bs) | 519 |
| 81 | 3 | 3 | CH₃ | 1.18(2H, m), 1.25–1.60(3H, m), 1.69(2H, t), 1.90–2.35(3H, m), 2.50(1H, m), 2.73(2H, m), 2.90(1H, m), 3.17(3H, m), 3.30–4.10(3H, m), 4.50(1H, m), 7.00–7.60(7H, m), 7.65–7.90(4H, m), 7.96(2H, bs), 8.10–8.30(2H, m) | 533 |
| 82 | 2 | 3 | ![methylfuryl] | 1.65(2H, t), 2.15(2H, m), 2.35–3.00(5H, m), 3.10(3H, m), 3.25–3.65(2H, m), 4.00–4.30(1H, m), 4.47(1H, m), 4.89(1H, m), 6.10(1H, s), 6.34(1H, s), 7.20–7.60(8H, m), 7.65–7.95(6H, m), 8.16(1H, bs), 8.29(1H, t) | 571 |

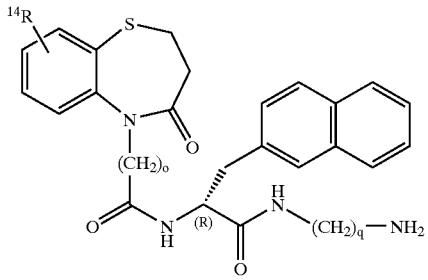

| Example number | o | q | R¹⁴ | ¹H-NMR (δ ppm): | FAB-MS (M + H)⁺ |
|---|---|---|---|---|---|
| 83 | 2 | 2 | 7-CF₃ | 2.05–2.60(4H, m), 2.70–2.95(3H, m), 3.10–3.70(6H, m), 3.90–4.25(1H, m), 4.49(1H, dd), 7.30–7.50(3H, m), 7.60(1H, d), 7.62(1H, s), 7.70–8.10(7H, m), 8.20–8.35(2H, m) | 559 |
| 84 | 3 | 2 | 7-CF₃ | 1.30–1.60(2H, m), 1.95–2.20(2H, m), 2.25–2.50(2H, m), 2.70–3.00(3H, m), 3.15–3.60(6H, m), 3.75–4.15(1H, m), 4.51(1H, m), 7.30–7.50(3H, m), 7.59(1H, d), 7.65–8.10(8H, m), 8.16(1H, d), 8.25(1H, t) | 573 |
| 85 | 2 | 3 | 7-CF₃ | 1.50–1.75(2H, m), 2.05–2.80(6H, m), 2.88(1H, dd), 3.00–3.20(3H, m), 3.20–3.70(2H, m), 3.95–4.35(1H, m), 4.46(1H, dd), 7.30–7.50(3H, m), 7.60(1H, d), 7.67(1H, s), 7.70–7.95(7H, m), 8.14(1H, t), 8.26(1H, d) | 573 |
| 86 | 3 | 3 | 7-CF₃ | 1.30–1.75(4H, m), 1.95–2.15(2H, m), 2.25–2.50(2H, m), 2.65–2.80(2H, m), 2.91(1H, dd), 3.00–3.50(6H, m), 3.80–4.15(1H, m), 4.50(1H, dd), 7.30–7.50(3H, m), 7.58(1H, d), 7.65–7.95(9H, m), 8.05–8.25(2H, m) | 587 |
| 87 | 2 | 4 | 7-CF₃ | 1.25–1.55(4H, m), 2.00–2.60(4H, m), 2.60–2.80(2H, m), 2.80–3.80(7H, m), 3.85–4.25(1H, m), 4.40–4.60(1H, m), 7.25–7.95(12H, m), 8.03(1H, t), 8.23(1H, d) | 587 |

-continued

| | | | | | |
|---|---|---|---|---|---|
| 88 | 3 | 4 | 7-CF$_3$ | 1.25–1.60(6H, m), 2.05(2H, t), 2.25–2.55(2H, m), 2.60–2.80(2H, m), 2.80–3.50(7H, m), 3.95(1H, bs), 4.45–4.60(1H, m), 7.30–7.95(12H, m), 8.00–8.15(2H, m) | 601 |
| 89 | 2 | 2 | 8-F | 2.00–2.65(4H, m), 2.70–3.00(3H, m), 3.10–3.65(6H, m), 3.85–4.25(1H, m), 4.40–4.60(1H, m), 7.20–7.55(5H, m), 7.65–8.10(6H, m), 8.15–8.35(2H, m) | 509 |
| 90 | 3 | 2 | 8-F | 1.25–1.60(2H, m), 1.95–2.20(2H, m), 2.25–2.55(2H, m), 2.70–3.70(9H, m), 3.85–4.10(1H, m), 4.40–4.60(1H, m), 7.20–7.50(5H, m), 7.65–8.10(7H, m), 8.17(1H, d), 8.26(1H, t) | 523 |
| 91 | 2 | 3 | 8-F | 1.55–1.75(2H, m), 2.00–2.55(4H, m), 2.55–2.80(2H, m), 2.89(1H, dd), 3.00–3.60(6H, m), 3.90–4.35(1H, m), 4.35–4.55(1H, m), 7.20–7.50(5H, m), 7.65–7.95(6H, m), 8.15(1H, t), 8.26(1H, d) | 523 |
| 92 | 3 | 3 | 8-F | 1.25–1.80(4H, m), 1.95–2.15(2H, m), 2.20–2.50(2H, m), 2.60–2.80(2H, m), 2.92(1H, dd), 3.00–3.65(6H, m), 3.85–4.10(1H, m), 4.40–4.60(1H, m), 7.20–7.55(5H, m), 7.60–8.00(7H, m), 8.05–8.25(2H, m) | 537 |

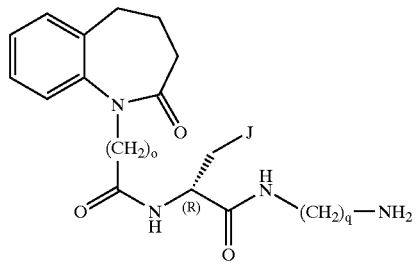

| Example number | o | q | J | $^1$H-NMR (δ ppm): | FAB-MS (M + H)$^+$ |
|---|---|---|---|---|---|
| 93 | 2 | 2 | 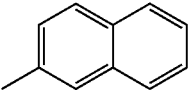 | 1.85–2.10(4H, m), 2.30(2H, m), 2.70–2.95(3H, m), 3.10–3.40(3H, m), 3.75–3.95(2H, bs), 4.50(1H, dd), 7.10–7.55(7H, m), 7.68(1H, s), 7.75–8.10(5H, m), 8.20–8.30(2H, m) | 473 |
| 94 | 2 | 3 | 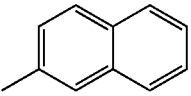 | 1.65(2H, m), 1.90–2.10(4H, m), 2.30(2H, m), 2.65–2.75(2H, m), 2.86(1H, dd), 3.05–3.15(3H, m), 3.70–3.90(2H, bs), 4.44(1H, dd), 7.10–7.50(7H, m), 7.68(1H, s), 7.75–7.95(5H, m), 8.16(1H, t), 8.27(1H, d) | 487 |
| 95 | 2 | 2 | 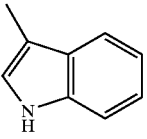 | 2.05(4H, m), 2.32(2H, m), 2.58(2H, m), 2.76(2H, m), 2.84(1H, dd), 3.09(1H, dd), 3.26(2H, m), 3.85(2H, bs), 4.38(1H, m), 6.90–7.40(8H, m), 7.53(1H, d), 7.89(2H, bs), 8.16(2H, m), 10.89(1H, s) | 462 |

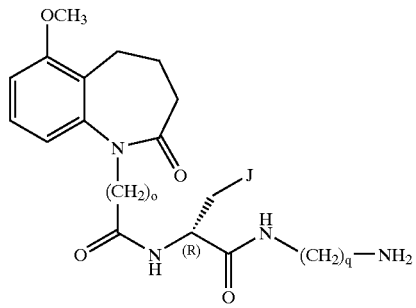

| Example number | o | q | J | $^1$H-NMR (δ ppm): | FAB-MS (M + H)$^+$ |
|---|---|---|---|---|---|
| 96 | 2 | 3 | 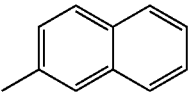 | 1.65(2H, m), 2.03(2H, m), 2.30(2H, m), 2.70(2H, m), 2.89(1H, dd), 3.10(3H, m), 3.78(3H, s), 4.45(1H, dd), 7.87(2H, d), 7.22(1H, t), 7.38(1H, d), 7.46(2H, m), 7.68(1H, s), 7.75–7.95(5H, m), 8.16(1H, t), 8.26(1H, d) | 517 |
| 97 | 3 | 3 | 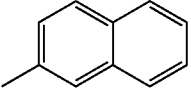 | 1.45(2H, m), 1.59(2H, m), 2.01(6H, m), 2.72(2H, m), 2.90(1H, dd), 3.14(3H, m), 3.80(3H, s), 4.50(1H, dd), 6.73(1H, bs), 6.87(1H, d), 7.19(1H, t), 7.35–7.55(3H, m), 7.69(1H, s), 7.75–7.95(5H, m), 8.21(2H, m) | 531 |

-continued
| | | | | | |
|---|---|---|---|---|---|
| 98 | 2 | 3 |  | 1.60–1.80(6H, m), 1.90–2.10(4H, m), 2.30(2H, bs), 2.55–2.85(7H, m), 3.05–3.15 (2H, m), 3.80(3H, s), 4.25(1H, dd), 6.85–6.95(5H, m), 7.25(1H, t), 7.80(3H, bs), 8.05–8.15(2H, m) | 521 |
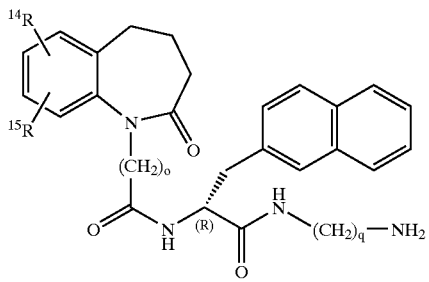
| Example number | o | q | R$^{14}$ | R$^{15}$ | $^1$H-NMR (δ ppm): | FAB-MS (M + H)$^+$ |
|---|---|---|---|---|---|---|
| 99 | 2 | 3 | 8-OMe | H | 1.65(2H, m), 1.80–2.15(4H, m), 2.31(2H, m), 2.70(2H, t), 2.87(1H, dd), 3.10(3H, m), 3.74(3H, s), 3.85(2H, bs), 6.75(1H, d), 6.86(1H, s), 7.10(1H, d), 7.38(1H, d), 7.46(2H, m), 7.68(1H, s), 7.70–7.95(5H, m), 8.15(1H, t), 8.26(1H, d) | 517 |
| 100 | 3 | 3 | 6-Me | 8-Me | 1.46(2H, bs), 1.68(2H, m), 2.02(4H, m), 2.22(3H, s), 2.25(3H, s), 2.73(2H, m), 2.91(1H, dd), 3.12 (3H, m), 4.51(1H, m), 6.87(2H, s), 7.43(3H, m), 7.70(1H, s), 7.75–7.95(5H, m), 8.20(2H, m) | 529 |
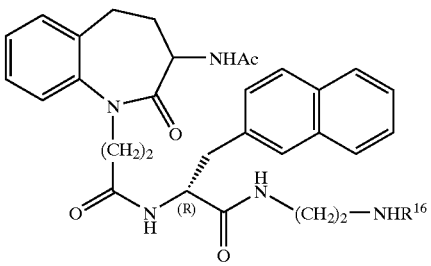
| Example number | R$^{16}$ | $^1$H-NMR (δ ppm): | FAB-MS (M + H)$^+$ |
|---|---|---|---|
| 101 | H | 1.79(3H, s), 1.85–2.70(4H, m), 2.70–2.95(3H, m), 3.10–3.35(3H, m), 4.14(2H, m), 4.46(1H, m), 7.15–7.55(7H, m), 7.67(1H, s), 7.70–8.00(5H, m), 8.10(1H, d), 8.23(1H, m), 8.25(1H, m) | 530 |
| 102 |  | 1.18(3H, t), 1.90(3H, s), 2.20–3.50(13H, m), 3.85–4.45(5H, m), 7.05–7.40(5H, m), 7.47(2H, m), 7.63 (1H, s), 7.77(3H, m) | 602 |
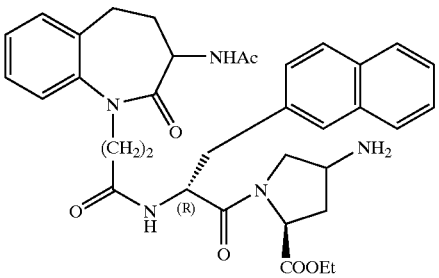
| Example number | $^1$H-NMR (δ ppm): | FAB-MS (M + H)$^+$ |
|---|---|---|
| 103 | 1.26(3H, t), 1.90–2.35(6H, m), 2.40–2.80(5H, m), 3.00–3.20(3H, m), 4.94(1H, m), 6.64(1H, d), 7.00–7.40(5H, m), 7.45(2H, m), 7.67(1H, s), 7.75(3H, m) | 571 |

-continued

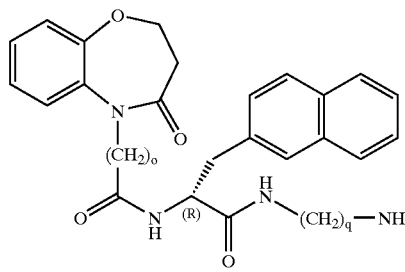

| Example number | o | q | ¹H-NMR (δ ppm): | FAB-MS (M + H)⁺ |
|---|---|---|---|---|
| 104 | 2 | 2 | 2.20–2.35(2H, m), 2.44(2H, t), 2.70–3.00(3H, m), 3.10–3.35(3H, m), 3.60–3.90(2H, m), 4.35–4.55(3H, m), 7.05–7.25(3H, m), 7.30–7.50(4H, m), 3.68(1H, s), 7.70–8.00(5H, m), 8.23(1H, t), 8.30(1H, d) | 475 |
| 105 | 2 | 3 | 1.55–1.75(2H, m), 2.20–2.35(2H, m), 2.43(2H, t), 2.60–2.80(2H, m), 2.89(1H, dd), 3.00–3.20(3H, m), 3.60–3.90(2H, m), 4.35–4.55(3H, m), 7.05–7.25(3H, m), 7.30–7.50(4H, m), 7.68(1H, s), 7.70–7.95(5H, m), 8.15(1H, t), 8.29(1H, d) | 489 |
| 106 | 3 | 2 | 1.35–1.55(2H, m), 1.95–2.20(2H, m), 2.40–2.55(2H, m), 2.75–3.00(3H, m), 3.15–3.45(3H, m), 3.50–3.70(2H, m), 4.35–4.60(3H, m), 7.05–7.25(4H, m), 7.35–7.50(3H, m), 7.69(1H, s), 7.75–8.05(5H, m), 8.15–8.30(2H, m) | 489 |
| 107 | 3 | 3 | 1.35–1.55(2H, m), 1.55–1.75(2H, m), 2.40–2.55(2H, m), 2.65–2.50(2H, m), 2.92(1H, dd), 3.05–3.20(3H, m), 3.45–3.75(2H, m), 4.40–4.55(3H, m), 7.05–7.25(4H, m), 7.35–7.50(3H, m), 7.70(1H, s), 7.75–7.90(5H, m), 8.10–8.25(2H, m) | 503 |

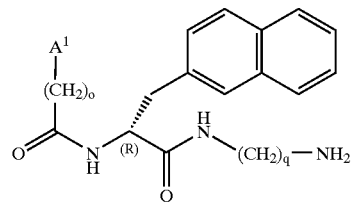

| Example number | o | q | A¹ | ¹H-NMR (δ ppm) | FAB-MS (M + H)⁺ |
|---|---|---|---|---|---|
| 108 | 2 | 3 | ![pyrrolo-benzodiazepinedione] | 1.64(2H, m), 2.27(2H, t), 2.42(1H, bs), 2.73(2H, m), 2.40(1H, dd), 3.00(3H, m), 5.40 (1H, m), 3.73(1H, m), 4.04(1H, m), 4.20(1H, m), 4.43(1H, dd), 7.30–7.60(6H, m), 7.65–7.95(7H, m), 8.15(1H, t), 8.30(1H, d) | 542 |
| 109 | 2 | 4 | ![N,N'-dimethyl-benzodiazepinedione] | 1.39(4H, m), 2.29(2H, m), 2.68(2H, m), 2.89(1H, m), 3.06(3H, m), 3.09(3H, s), 3.55–3.80(2H, m), 3.90–4.25(2H, m), 4.49(1H, m), 7.25–7.60(6H, m), 7.60–7.90 (7H, m), 8.01(1H, bs), 8.25(1H, t) | 530 |
| 110 | 2 | 3 | ![acetyl-dimethyl-benzodiazepinone] | 1.09(3H, m), 1.75(4H, m), 2.10–2.65(3H, m), 2.81(4H, m), 3.00–3.40(3H, m), 4.00–4.40(2H, m), 4.53(1H, m), 7.20–7.55(9H, m), 7.65–7.90(6H, m) | 545 |

-continued

| | | | | <sup>1</sup>H-NMR (DMSO-d<sub>6</sub>) δ: | FAB-MS |
|---|---|---|---|---|---|
| 111 | 2 | 2 | 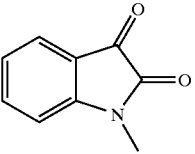 | 2.45(2H, m), 2.78(2H, m), 2.90(1H, dd), 3.15(1H, dd), 3.28(2H, m), 3.74(2H, m), 4.53 (1H, dd), 7.09(2H, m), 7.35–7.55(4H, m), 7.59(1H, t), 7.68(1H, s), 7.78(3H, m), 8.02(2H, bs), 8.31(1H, t), 8.48(1H, t) | 459 |
| 112 | 2 | 3 | 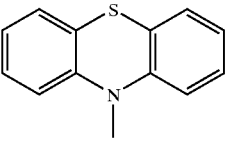 | 1.28(2H, m), 2.42(2H, m), 2.67(2H, m), 3.15(4H, m), 4.15(2H, m), 4.62(1H, dd), 6.51 (1H, d), 6.87(3H, m), 6.96(2H, t), 7.10–7.25(5H, m), 7.40–7.55(3H, m), 7.68– 7.85(3H, m) | 525 |
| 113 | 3 | 3 | 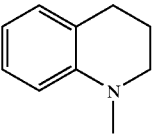 | 1.50–1.85(6H, m), 2.10(2H, m), 2.55–2.80(3H, m), 2.80–3.20(7H, m), 4.58(1H, m), 6.59(2H, m), 6.89(2H, m), 7.44(3H, m), 7.60–8.00(6H, m), 8.28(2H, m) | 473 |

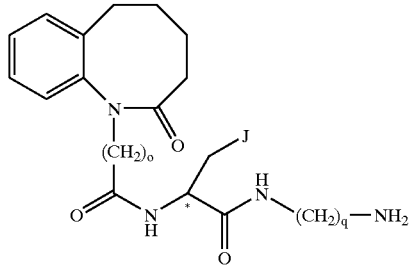

| Example number | o | q | * | J | <sup>1</sup>H-NMR (DMSO-d<sub>6</sub>) δ: | FAB-MS (M + H)<sup>+</sup> |
|---|---|---|---|---|---|---|
| 114 | 2 | 2 | (R) | 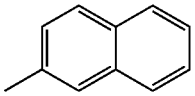 | 1.20(1H, m), 1.51(1H, m), 1.73(2H, m), 2.25–3.00(9H, m), 3.10–3.50(4H, m), 4.15(1H, m), 4.47(1H, m), 7.27(4H, m), 7.35–7.55(3H, m), 7.69(1H, s), 7.75–8.10(5H, m), 8.27(2H, m) | 487 |
| 115 | 2 | 3 | (R) | 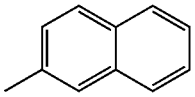 | 1.20(1H, m), 1.35–2.65(11H, m), 2.70(2H, m), 2.88(1H, m), 3.10(3H, m), 4.15(1H, m), 4.45(1H, m), 7.25(4H, m), 7.35–7.55(3H, m), 7.69(1H, s), 7.75–7.95(5H, m), 8.17(1H, t), 8.27(1H, d) | 501 |
| 116 | 2 | 3 | (RS) | 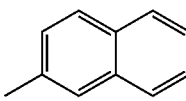 | 1.55–1.80(4H, m), 1.95–2.20(4H, m), 2.30–2.45(1H, m), 2.55–2.85 (5H, m), 2.95–3.15(4H, m), 3.30–3.45(1H, m), 4.10–4.20(1H, m), 4.35–4.45(1H, m), 7.00–7.05(2H, m), 7.20–7.30(5H, m), 7.55–7.60 (2H, m), 7.65(1H, d), 7.80(3H, bs), 8.10(1H, t), 8.25(1H, d), 9.50(1H, s) | 517 |

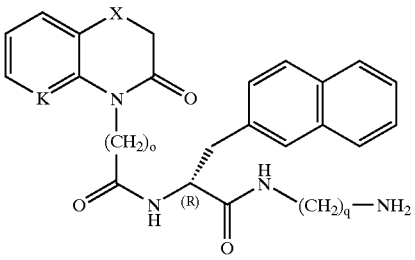

| Example number | o | q | X | K | <sup>1</sup>H-NMR (DMSO-d<sub>6</sub>) δ: | FAB-MS (M + H)<sup>+</sup> |
|---|---|---|---|---|---|---|
| 117 | 2 | 2 | CH<sub>2</sub> | CH | 2.30–2.55(4H, m), 2.80(4H, m), 2.95(1H, dd), 2.95(1H, dd), 3.25(1H, dd), 3.88(1H, m), 3.96(1H, m), 4.55(1H, dd), 7.00(2H, m), 7.18(2H, m), 7.46(3H, m), 7.72(1H, s), 7.75–7.95(3H, m), 8.00(2H, bs), 8.30(1H, t), 8.43(1H, d) | 459 |
| 118 | 2 | 3 | CH<sub>2</sub> | CH | 1.68(2H, m), 2.25–2.50(4H, m), 2.77(4H, m), 2.92(1H, dd), 3.13(3H, m), 3.87(1H, m), 3.97(1H, m), 4.56(1H, dd), 7.08(2H, m), 7.18(2H, m), 7.45(3H, m), 7.72(1H, s), 7.75–7.95(5H, m), 8.22(1H, t), 8.41(1H, d) | 473 |

-continued

| | | | | | | |
|---|---|---|---|---|---|---|
| 119 | 2 | 3 | S | CH | 1.64(2H, m), 2.75(2H, m), 2.94(1H, m), 3.13(3H, m), 3.90(1H, m), 4.54(1H, m), 7.04(1H, m), 7.23(2H, m), 7.35–7.50(4H, m), 7.60–7.90(6H, m), 8.32(1H, t), 8.41(1H, d) | 491 |
| 120 | 3 | 2 | S | CH | 1.58(2H, m), 2.09(2H, m), 2.82(2H, m), 2.93(1H, dd), 3.23(1H, dd), 3.43(2H, s), 3.53(1H, m), 3.77(1H, m), 4.58(1H, m), 7.03(1H, t), 7.19(2H, m), 7.40(4H, m), 7.72(4H, m), 7.98(2H, bs), 8.27(1H, d), 8.32(1H, t) | 491 |
| 121 | 3 | 3 | S | CH | 1.50–1.75(4H, m), 2.10(2H, t), 2.74(2H, m), 2.91(1H, dd), 3.13(3H, m), 3.43(2H, s), 3.52(1H, m), 3.77(1H, m), 4.57(1H, m), 7.03(1H, t), 7.10–7.25(2H, m), 7.41(4H, m), 7.65–7.95(6H, m), 8.25(2H, m) | 505 |
| 122 | 2 | 2 | O | CH | 2.41(2H, m), 2.82(2H, m), 2.94(1H, dd), 3.22(1H, dd), 3.87(1H, m), 4.00(1H, m), 4.54(1H, m), 4.55(2H, s), 6.99(3H, s), 7.11(1H, d), 7.35–7.50(3H, m), 7.71(1H, s), 7.82(3H, m), 7.95(2H, bs), 8.30(1H, t), 8.49(1H, t) | 461 |
| 123 | 2 | 3 | O | CH | 1.68(2H, m), 2.41(2H, m), 2.72(2H, m), 2.91(1H, dd), 3.13(3H, m), 4.53(1H, m), 4.57(2H, s), 6.99(3H, m), 7.13(1H, m), 7.44(3H, m), 7.72(1H, s), 7.75–8.00(5H, m), 8.24(1H, t), 8.46(1H, d), | 475 |
| 124 | 2 | 2 | O | N | 2.45(2H, m), 2.81(2H, m), 2.92(1H, dd), 3.19(1H, dd), 3.30(2H, m), 4.12(2H, t), 4.53(1H, dd), 4.72(2H, s), 7.03(3H, dd), 7.38(1H, d), 7.47(3H, m), 7.72(1H, s), 7.82(3H, m), 7.97(1H, d), 7.97(2H, bs), 8.29(1H, t), 8.37(1H, d) | 462 |
| 125 | 2 | 3 | O | N | 1.67(2H, m), 2.44(2H, m), 2.72(2H, m), 2.93(1H, dd), 3.11(3H, m), 4.12(2H, t), 4.51(1H, m), 4.72(2H, s), 7.04(1H, dd), 7.37(1H, d), 7.47(3H, m), 7.72(1H, s), 7.75–7.95(5H, m), 7.97(1H, d), 8.22(1H, t), 8.36(1H, d) | 476 |

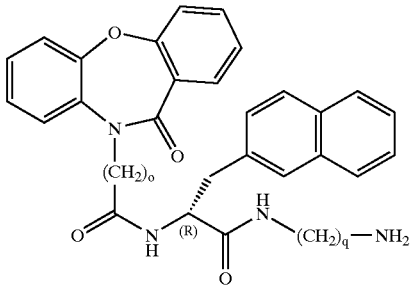

| Example number | o | q | $^1$H-NMR ($\delta$ ppm): | FAB-MS $(M + H)^+$ |
|---|---|---|---|---|
| 126 | 2 | 3 | 1.65(2H, m), 2.55(2H, m), 2.73(2H, m), 2.90(1H, dd), 3.10–3.20(3H, m), 4.10(2H, bs), 4.50(1H, dd), 7.20–7.65(9H, m), 7.65–7.90(7H, m), 8.20(1H, t), 8.39(1H, d) | 537 |
| 127 | 3 | 3 | 1.67(4H, m), 2.11(2H, t), 2.75(2H, m), 2.90(1H, dd), 3.13(3H, m), 3.83(1H, m), 3.93(1H, m), 4.52(1H, m), 7.15–7.50(9H, m), 7.57(1H, t), 7.65–7.95(7H, m), 8.22(2H, m) | 551 |

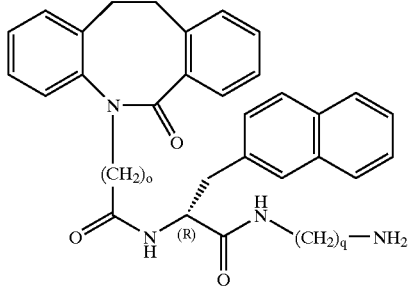

| Example number | o | q | $^1$H-NMR ($\delta$ ppm): | FAB-MS $(M + H)^+$ |
|---|---|---|---|---|
| 128 | 3 | 2 | 1.30–1.75(2H, m), 2.14(2H, t), 2.70–3.50(11H, m), 3.89(1H, m), 4.55(1H, m), 6.90–7.15(8H, m), 7.47(3H, m), 7.70–7.90(4H, m), 8.01(2H, bs), 8.30(2H, m) | 549 |
| 129 | 3 | 3 | 1.45–1.75(4H, m), 2.13(2H, t), 2.65–3.35(10H, m), 3.89(1H, m), 4.54(1H, m), 6.90–7.15(8H, m), 7.47(3H, m), 7.70–7.95(6H, m), 8.24(2H, m) | 563 |
| 130 | 4 | 3 | 1.15–1.50(4H, m), 1.66(2H, m), 2.08(2H, t), 2.71(2H, m), 2.91(3H, m), 3.52(1H, m), 3.91(1H, m), 4.53(1H, dd), 6.90–7.15(8H, m), 7.49(3H, m), 7.71(1H, s), 7.75–7.95(5H, m), 8.19(2H, m) | 577 |
| 131 | 4 | 4 | 1.20–1.55(8H, m), 2.07(2H, t), 2.70(2H, m), 2.80–3.20(8H, m), 3.90(1H, m), 4.56(1H, dd), 6.96(1H, d), 7.07(7H, m), 7.45(3H, m), 7.70(1H, s), 7.75–7.90(5H, m), 8.07(1H, t), 8.13(1H, d) | 591 |

-continued

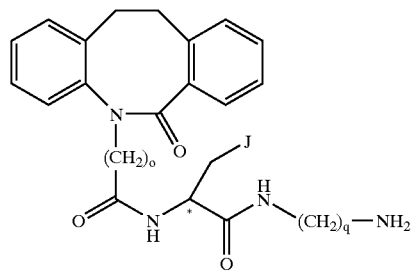

| Example number | o | q | * | J | ¹H-NMR (δ ppm): | FAB-MS (M + H)⁺ |
|---|---|---|---|---|---|---|
| 132 | 2 | 3 | (R) | ![tetrahydronaphthyl] | 1.60–1.75(6H, m), 2.30–2.50(2H, m), 2.60–2.90(10H, m), 3.05–3.20(4H, m), 3.50–3.60(1H, m), 4.20–4.40(2H, m), 6.85–7.15 (11H, m), 7.75–7.90(3H, bs), 8.13(1H, t), 8.25(1H, d) | 553 |
| 133 | 2 | 3 | (RS) | ![hydroxynaphthyl] | 1.55–1.75(2H, m), 2.30–2.50(2H, m), 2.60–2.90(5H, m), 2.90–3.20(5H, m), 3.40–3.55(1H, m), 4.20–4.30(1H, m), 4.40–4.50(1H, m), 6.90–7.20(10H, m), 7.25–7.30(1H, m), 7.55–7.65(3H, m), 7.75(3H, bs), 8.15(1H, t), 8.30–8.35(1H, m), 9.65(1H, s) | 565 |

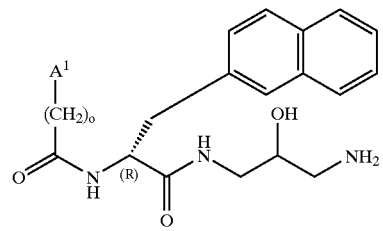

| Example number | o | A¹ | ¹H-NMR (δ ppm): | FAB-MS (M + H)⁺ |
|---|---|---|---|---|
| 134 | 2 | ![benzothiazepinone] | 2.00–2.70(5H, m), 2.70–2.95(2H, m), 3.00–3.60(6H, m), 3.65–3.80(1H, m), 3.73(1H, bs), 4.50(1H, bs), 5.54(1H, bs), 7.26(1H, t), 7.30–7.50(5H, m), 7.57(1H, d), 7.60–7.95(6H, m), 8.15–8.35(2H, m) | 521 |
| 135 | 3 | ![benzothiazepinone] | 1.25–1.60(2H, m), 1.95–2.15(2H, m), 2.15–2.70(3H, m), 2.70–3.00(2H, m), 3.00–3.45 (6H, m), 3.72(1H, bs), 4.00(1H, bs), 4.55(1H, dd), 5.55(1H, bs), 7.24(1H, t), 7.30–7.50(5H, m), 7.58(1H, d), 7.65–7.95(6H, m), 8.14(1H, d), 8.23(1H, t) | 535 |
| 136 | 2 | ![F-benzothiazepinone] | 1.95–2.70(4H, m), 2.70–2.95(2H, m), 3.00–3.55(7H, m), 3.65–3.80(1H, m), 3.85–4.25 (1H, m), 4.40–4.60(1H, m), 7.20–7.50(6H, m), 7.60–7.95(6H, m), 8.10–8.35(2H, m), | 539 |
| 137 | 3 | ![F-benzothiazepinone] | 1.25–1.60(2H, m), 1.95–2.15(2H, m), 2.25–2.60(4H, m), 2.60–3.55(7H, m), 3.65–3.80 (1H, m), 3.85–4.10(1H, m), 4.53(1H, dd), 7.20–7.50(6H, m), 7.65–7.95(6H, m), 8.13(1H, d), 8.22(1H, t) | 553 |

| | | | | |
|---|---|---|---|---|
| 138 | 2 | (structure: 7-CF3 benzothiazepinone, N-methyl) | 2.00–2.70(5H, m), 2.70–2.95(2H, m), 3.00–3.80(7H, m), 3.90–4.35(1H, m), 4.50(1H, bs), 5.54(1H, bs), 7.30–7.50(3H, m), 7.59(1H, d), 7.68(1H, s), 7.70–8.00(7H, m), 8.15–8.40(2H, m) | 589 |
| 139 | 3 | (structure: 7-CF3 benzothiazepinone, N-methyl) | 1.25–1.60(2H, m), 1.90–2.15(2H, m), 2.20–2.70(3H, m), 2.70–3.50(8H, m), 3.73(1H, bs), 3.95(1H, bs), 4.54(1H, dd), 5.54(1H, d), 7.30–7.95(12H, m), 8.13(1H, d), 8.23(1H, t) | 603 |
| 140 | 2 | (structure: OCH3-benzazepinone, N-methyl) | 1.85–2.10(4H, m), 2.28(2H, bs), 2.56(2H, m), 2.70–2.95(2H, m), 3.05–3.30(3H, m), 3.73(2H, m), 3.78(3H, s), 4.50(1H, m), 5.60(1H, bs), 6.84(2H, m), 7.22(1H, t), 7.45–7.55(3H, m), 7.69(1H, s), 7.75–7.95(5H, m), 8.25(2H, m) | 533 |
| 141 | 3 | (structure: OCH3-benzazepinone, N-methyl) | 1.44(2H, m), 2.02(4H, m), 2.40–3.85(12H, m), 4.54(1H, m), 6.73(1H, bs), 6.86(1H, d), 7.18(1H,t), 7.46(3H, m), 7.70–7.95(6H, m), 8.20(1H, d), 8.25(1H, t) | 547 |
| 142 | 2 | (structure: benzoxazepinone, N-methyl) | 2.15–2.35(2H, m), 2.43(2H, t), 2.50–2.70(1H, m), 2.70–2.95(2H, m), 3.00–3.25(3H, m), 3.60–3.90(3H, m), 4.41(2H, t), 4.45–4.60(1H, m), 5.56(1H, bs), 7.05–7.25(3H, m), 7.25–7.35(1H, m), 7.35–7.50(3H, m), 7.69(1H, s), 7.70–8.00(5H, m), 8.23(1H, t), 8.31(1H, d) | 505 |
| 143 | 3 | (structure: benzoxazepinone, N-methyl) | 1.35–1.55(2H, m), 1.90–2.10(2H, m), 2.35–2.70(3H, m), 2.70–3.00(2H, m), 3.00–3.85(6H, m), 4.35–4.60(3H, m), 5.55(1H, bs), 7.05–7.25(4H, m), 7.35–7.50(3H, m), 7.60–7.95(6H, m), 8.17(1H, d), 8.23(1H, t) | 519 |
| 144 | 2 | (structure: benzazocinone, N-methyl) | 1.23(1H, m), 1.50(1H, m), 1.74(2H, m), 1.95–3.60(15H, m), 3.73(1H, m), 4.12(1H, m), 4.48(1H, m), 5.54(1H, bs), 7.24(4H, m), 7.46(3H, m), 7.70(1H, s), 7.75–7.90(5H, m), 8.25(2H, m) | 517 |
| 145 | 2 | (structure: dibenzoxazepinone, N-methyl) | 2.55(2H, m), 2.70–3.00(3H, m), 3.15(3H, m), 3.75(1H, m), 4.06(2H, m), 4.55(1H, m), 7.15–7.50(10H, m), 7.55–7.95(7H, m), 8.25(1H, t), 8.38(1H, m) | 553 |

-continued
| | | | | |
|---|---|---|---|---|
| 146 | 2 | 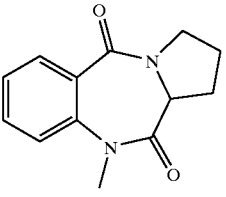 | 1.90(2H, m), 2.25(2H, m), 2.40–2.65(3H, m), 2.70–2.95(2H, m), 3.16(3H, m), 3.41 (1H, m), 3.53(1H, m), 3.71(2H, m), 4.04(2H, m), 4.16(1H, m), 4.47(1H, m), 5.53(1H, d), 7.25–7.60(6H, m), 7.65–7.95(7H, m), 8.19(1H, t), 8.26(1H, d) | 558 |
| 147 | 2 | 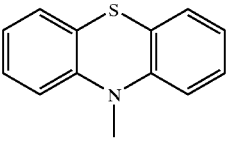 | 2.40–2.70(2H, m), 2.70–3.00(2H, m), 3.05–3.45(4H, m), 3.70–3.90(3H, m), 4.64 (1H, m), 5.58(1H, bs), 6.90(4H, m), 7.11(4H, m), 7.45(3H, m), 7.73(1H, s), 7.75–7.95 (5H, m), 8.31(1H, t), 8.39(1H, d) | 541 |
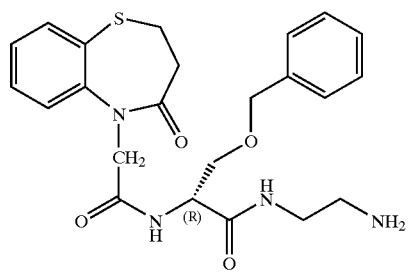
| Example number | $^1$H-NMR (δ ppm): | FAB-MS (M + H)$^+$ |
|---|---|---|
| 149 | 2.35–2.55(2H, m), 2.75–2.95(2H, m), 3.10–3.50(4H, m), 3.60–3.75(2H, m), 4.03(1H, bs), 4.45–4.90(4H, m), 7.2–7.5(8H, m), 7.59(1H, d), 7.94(2H, bs), 8.22(1H, t), 8.40 (1H, d) | 457 |
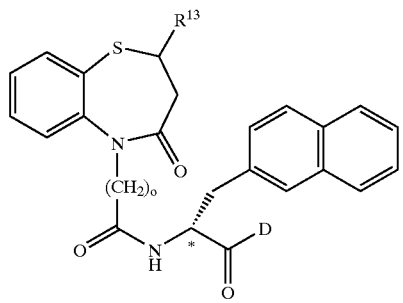
| Example number | o | * | R$^{13}$ | D | $^1$H-NMR (δ ppm): | FAB-MS (M + H)$^+$ |
|---|---|---|---|---|---|---|
| 150 | 1 | (S) | H | 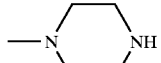 | 2.30–2.45(2H, m), 2.80–3.95(13H, m), 4.60(1H, bs), 5.10(1H, dd), 7.10–7.25(1H, m), 7.40–7.60(5H, m), 7.65–7.95(5H, m), 8.59 (1H, bs), 9.25(1H, bs), 9.64(1H, bs) | 503 |
| 151 | 2 | (S) | H | 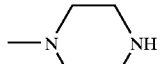 | 2.30–2.60(4H, m), 2.80–3.80(12H, m), 4.10(1H, bs), 4.45(1H, bs), 4.95(1H, bs), 7.20–7.90(11H, m), 8.50(1H, d), 8.80(1H, bs) | 517 |
| 152 | 2 | (R) | CH$_3$ | 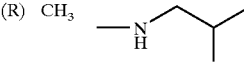 | 1.14(2H, d), 1.32(1H, d), 1.80–3.55(11H, m), 3.55–4.20(3H, m), 4.49(1H, m), 5.55(1H, bs), 7.26(1H, m), 7.30–7.60(6H, m), 7.65–7.95(6H, m), 8.15–8.35(2H, m), | 535 |
| 153 | 2 | (R) | CH$_3$ |  | 1.17(2H, d), 1.36(1H, d), 1.80–2.30(2H, m), 2.47(2H, m), 2.90 (1H, m), 3.10(1H, m), 3.52(2H, m), 3.60–4.20(3H, m), 3.73(2H, m), 4.50(1H, m), 5.51(2H, m), 7.27(1H, m), 7.30–7.60(6H, m), 7.65–7.90(4H, m), 8.04(2H, bs), 8.27(2H, m) | 531 |

-continued

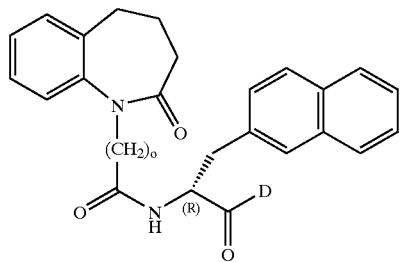

| Exampl number | o | D | ¹H-NMR (δ ppm): | FAB-MS (M + H)⁺ |
|---|---|---|---|---|
| 154 | 2 | —NH—(CH₂)₄—NH₂ | 1.30–1.50(4H, m), 1.90–2.10(4H, m), 2.30(2H, m), 2.68(2H, m), 2.86(1H, dd), 3.07 (3H, m), 3.80(1H, bs), 4.48(1H, dd), 7.10–7.30(4H, m), 7.30–7.50(3H, m), 7.67(1H, s), 7.75–7.90(5H, m), 8.04(1H, t), 8.23(1H, d) | 501 |
| 155 | 2 | —NH—CH₂—CH(OH)—CH₂—NH₂ | 2.01(4H, m), 2.29(2H, m), 2.70–2.90(2H, m), 3.12(3H, m), 3.38(2H, m), 3.74(2H, m), 4.49(1H, m), 5.55(1H, bs), 7.10–7.30(4H, m), 7.35–7.55(3H, m), 7.69(1H, s), 7.75–7.95(5H, m), 8.23(2H, m) | 503 |
| 156 | 2 | —NH—CH₂—CH=CH—CH₂—NH₂ (cis) | 2.00(4H, m), 2.30(2H, m), 2.86(1H, m), 3.07(1H, m), 3.45–4.00(6H, m), 4.49(1H, m), 5.50(2H, m), 7.10–7.30(4H, m), 7.30–7.50(3H, m), 7.67(1H, s), 7.75–7.95(3H, m), 8.04(2H, b), 8.25(2H, m) | 499 |
| 157 | 2 | —NH—CH₂—C≡C—CH₂—NH₂ | 2.02(4H, m), 2.29(2H, m), 2.86(1H, dd), 3.12(1H, dd), 3.71(2H, s), 3.60–4.10(2H, m), 3.95(2H, d), 4.52(1H, m), 7.10–7.30(4H, m), 7.35–7.50(3H, m), 7.68(1H, s), 7.70–7.90(3H, m), 8.26(1H, d), 8.34(2H, bs), 8.54(1H, t) | 497 |

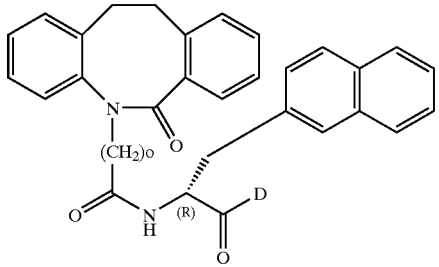

| Example number | o | D | ¹H-NMR (δ ppm): | FAB-MS (M + H)⁺ |
|---|---|---|---|---|
| 158 | 2 | —NH—CH₂—CH₂—NH₂ | 2.25–3.60(13H, m), 4.20(1H, m), 4.35(1H, m), 6.85–7.15(8H, m), 7.35–7.50 (3H, m), 7.72(1H, s), 7.80–8.00(5H, m), 8.29(1H, t), 8.38(1H, d) | 535 |
| 159 | 2 | —NH—CH₂—CH₂—NH₂ | 1.66(2H, m), 2.30–3.55(13H, m), 4.24(1H, m), 4.51(1H, m), 6.85–7.15(8H, m), 7.40–7.55(3H, m), 7.71(1H, s), 7.80–7.95(5H, m), 8.22(1H, t), 8.36(1H, d) | 549 |
| 160 | 2 | —NH—CH₂—CH(OH)—CH₂—NH₂ | 2.25–3.60(13H, m), 3.73(1H, m), 4.22(1H, m), 4.57(1H, m), 5.55(1H, bs), 6.85–7.15(8H, m), 7.47(3H, m), 7.73(1H, s), 7.80–7.95(m, 5H), 8.27(1H, t), 8.34 (1H, m) | 565 |
| 161 | 2 | —NH—CH₂—CH=CH—CH₂—NH₂ | 2.42(2H, m), 2.70(2H, m), 2.85–3.20(4H, m), 3.50(3H, m), 3.75(2H, m), 4.15–4.65(2H, m), 5.51(2H, m), 6.85–7.15(8H, m), 7.46(3H, m), 7.71(1H, s), 7.75–7.90(3H, m), 8.08(2H, bs), 8.35(2H, m) | 561 |

-continued

| | | | ¹H-NMR (δ ppm): | FAB-MS (M + H)⁺ |
|---|---|---|---|---|
| 162 | 2 | ![structure: -NH-CH2-CH=CH-CH2-NH2] | 2.41(2H, m), 2.69(2H, m), 2.85–3.25(4H, m), 3.34(2H, m), 4.22(1H, m), 4.59(1H, m), 5.55(1H, m), 5.70(1H, m), 6.85–7.15(8H, m), 7.48(3H, m), 7.73(1H, s), 7.83(3H, m), 8.02(2H, bs), 8.34(2H, m) | 561 |
| 163 | 2 | ![structure: -NH-CH2-C≡C-CH2-NH2] | 2.40(2H, m), 2.67(2H, m), 2.80–3.20(4H, m), 3.50(1H, m), 3.71(2H, m), 3.99(2H, m), 4.21(1H, m), 4.58(1H, m), 6.85–7.15(8H, m), 7.48(3H, m), 7.72(1H, s), 7.82(3H, m), 8.35(3H, m), 8.60(1H, t) | 559 |

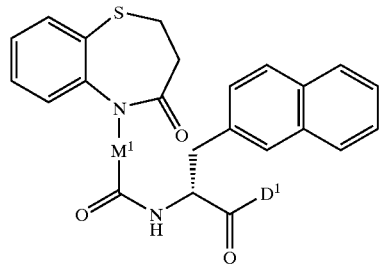

| Example number | M¹ | D¹ | ¹H-NMR (δ ppm): | FAB-MS (M + H)⁺ |
|---|---|---|---|---|
| 164 | isobutyl (CH3-CH(CH3)-CH2-) | -NH-CH2CH2-NH2 | 0.50–1.05(3H, m), 2.35(2H, m), 2.84(3H, m), 3.10–3.60(8H, m), 3.60–4.65(1H, m), 7.23(1H, m), 7.45(6H, m), 7.68(1H, s), 7.75–8.10(5H, m), 8.10–8.45(2H, m) | 505 |
| 165 | isobutyl | -NH-(CH2)3-NH2 | 0.45–1.15(3H, m), 1.15–1.80(2H, m), 2.15–2.45(2H, m), 2.50–3.00(4H, m), 3.00–3.75(7H, m), 3.85–4.65(1H, m), 7.10–8.35(15H, m) | 519 |
| 166 | n-pentyl | -NH-CH2-C(CH3)2-NH2 | 1.10(6H, s), 1.30–1.65(2H, m), 1.95–2.20(2H, m), 2.20–2.45(2H, m), 2.95(1H, dd), 3.99(1H, bs), 4.57(1H, m), 7.25(1H, t), 7.30–7.55(4H, m), 7.59(1H, d), 7.65, 8.05(7H, m), 8.22(1H, d), 8.33(1H, t) | 533 |
| 167 | n-pentyl | -NH-CH2CH2-(4-piperidyl) | 1.26(2H, m), 1.95–2.72(6H, m), 2.73–3.10(3H, m), 3.11–3.75(6H, m), 4.10(2H, m), 4.50(1H, m), 4.89(1H, m), 7.20–7.40(2H, m), 7.45(4H, m), 7.60(2H, m), 7.75(3H, m), 8.22(1H, t), 8.37(1H, d) | 545 |
| 168 | n-pentyl | -NH-CH2CH2-NH-CH2CH2-OH | 2.25–2.75(8H, m), 3.05–3.40(6H, m), 3.51(2H, m), 4.30–4.70(2H, m), 6.96(1H, m), 7.10–7.50(7H, m), 7.50–7.85(5H, m) | 535 |
| 169 | n-pentyl | -NH-(CH2)3-NH-CH2CH2-OH | 1.30–1.60(2H, m), 1.60–1.80(2H, m), 1.95–2.15(2H, m), 2.15–2.45(2H, m), 2.70–2.95(4H, m), 3.55–3.70(2H, m), 3.97(1H, bs), 3.47(1H, m), 5.27(1H, bs), 7.24(1H, t), 7.30–7.50(5H, m), 7.58(1H, d), 7.65–7.90(4H, m), 8.10–8.25(2H, m), 8.61(1H, bs) | 563 |
| 170 | n-pentyl | -NH-(CH2)3-NH-C(CH3)2-CH2OH | 1.15(6H, s), 1.35–1.60(2H, m), 1.65–1.85(2H, m), 2.00–2.15(2H, m), 2.20–2.45(2H, m), 2.65–2.85(2H, m), 2.92(1H, dd), 3.05–3.45(7H, m), 3.95(1H, bs), 4.48(1H, m), 5.58(1H, s), 7.24(1H, t), 7.35–7.50(4H, m), 7.58(1H, d), 7.65–7.90(4H, m), 8.10–8.45(4H, m) | 591 |
| 171 | n-pentyl | -NH-CH2-CH(OH)-C(CH3)2-NH2 | 1.16(3H, d), 1.22(3H, s), 1.30–1.60(2H, m), 1.95–2.15(2H, m), 2.20–2.45(2H, m), 2.80–3.60(8H, m), 3.94(1H, bs), 4.50–4.70(1H, m), 7.24(1H, t), 7.30–7.50(5H, m), 7.58(1H, d), 7.65–7.95(6H, m), 8.05–8.30(2H, m) | 563 |

-continued

| | | | |
|---|---|---|---|
| 172 | (structure) | 1.80(3H, d), 1.30–1.60(2H, m), 1.95–2.15(2H, m), 2.20–2.45(2H, m), 2.60–2.80(2H, m), 2.80–3.65(9H, m), 3.75–4.10(3H, m), 4.45–4.60(1H, m), 5.30(1H, bs), 5.60(1H, bs), 7.24(1H, bs), 7.30–7.50(5H, m), 7.58(1H, d), 7.65–7.90 (5H, m), 8.10–8.35(2H, m) | 593 |
| 173 | (structure) | 2.00–2.55(4H, m), 2.65–4.30(16H, m), 7.26(1H, m), 7.45(5H, m), 7.70(1H, s), 7.75–7.90(3H, m), 8.52(1H, d) | 547 |
| 174 | (structure) | 1.22–1.65(2H, m), 1.65–1.85(2H, m), 1.95–2.15(2H, m), 2.20–2.45(2H, m), 3.95(1H, bs), 4.98(1H, bs), 7.24(1H, t), 7.30–7.50(4H, m), 7.58(1H, d), 7.65–8.05(5H, m), 8.32(1H, t) | 563 |
| 175 | (structure) | 1.30–1.65(2H, m), 1.65–1.80(2H, m), 1.90(3H, s), 1.95–2.15(2H, m), 2.20–2.50(2H, m), 2.60–2.85(2H, m), 2.85–3.75(10H, m), 3.90–4.15(2H, m), 4.85–5.05(1H, m), 7.24 (1H, t), 7.30–7.55(4H, m), 7.58(1H, d), 7.65–8.05(5H, m), 8.25–8.45(1H, m) | 605 |
| 176 | (structure) | 1.40–1.60(2H, m), 1.75–1.90(2H, m), 2.00–2.15(2H, m), 2.30–2.45(2H, m), 2.95(2H, bt), 3.15(4H, bt), 3.90–4.00 (1H, m), 4.40–4.50(1H, m), 7.1(1H, bs), 7.25(1H, bt), 7.35–7.50(4H, m), 7.55–7.90(7H, m), 8.15(1H, s), 8.20–8.30(5H, m) | — |
| 177 | (structure) | 1.35–1.95(4H, m), 2.00–2.55(4H, m), 2.64(1H, m), 2.90–3.55(8H, m), 3.85–4.60(1H, m), 4.73(1H, m), 6.92(1H, m), 7.00–7.50(6H, m), 7.52(1H, d), 7.69(4H, m), 8.18(1H, m) | 561 |
| 178 | (structure) | 1.30–1.60(2H, m), 1.65–1.85(2H, m), 2.00–2.15(2H, m), 2.20–2.45(2H, m), 2.70–3.00(3H, m), 3.20–3.70(8H, m), 3.85–4.10(1H, m), 4.40–4.55(1H, m), 7.24(1H, t), 7.35–7.65(6H, m), 7.65–7.95(9H, m), 8.10–8.30(2H, m), 8.88 (2H, bs) | 576 |
| 179 | (structure) | 0.45–1.10(3H, m), 1.45(6H, m), 2.35(2H, m), 2.89(1H, m), 3.05–3.75(10H, m), 3.80–4.65(1H, m), 7.15–7.62(7H, m), 7.69(1H, s), 7.76(3H, m), 8.22(5H, m) | 590 |
| 180 | (structure) | 1.70–1.95(2H, m), 2.30–2.65(4H, m), 3.03(2H, m), 3.15–3.40(4H, m), 3.64(2H, m), 3.74(2H, t), 4.40–4.75(2H, m), 6.81(1H, s), 6.97(1H, s), 7.20–7.55(7H, m), 7.56–7.90 (5H, m) | 556 |
| 181 | (structure) | 1.35–1.60(2H, m), 2.00–2.10(2H, m), 2.25–2.45(3H, m), 2.55–2.70(1H, m), 2.75–3.00(3H, m), 3.00–3.40(4H, m), 3.70–3.80(1H, m), 3.90–4.00(1H, m), 4.45–4.55(1H, m), 7.25(2H, t), 7.35–7.50(5H, m), 7.55(1H, d), 7.70(1H, s), 7.65–7.90(6H, m), 8.15(1H, d), 8.20–8.35(1H, m) | 535 |
| 182 | (structure) | 1.35–1.60(2H, m), 2.0–2.10(2H, m), 2.25–2.45(2H, m), 2.55–2.70(1H, m), 2.80–2.95(2H, m), 3.0–3.4(6H, m), 3.70–3.80(1H, m), 3.90–4.00(1H, m), 4.45–4.55(1H, m), 7.25(1H, bt), 7.40–7.50(4H, m), 7.60(1H, d), 7.85–8.00 (6H, m), 8.05–8.10(1H, m), 8.15(1H, d), 8.25(1H, bt) | 535 |

-continued

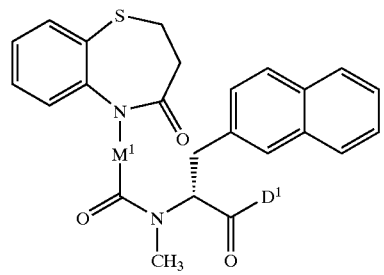

| Example number | M[1] | D[1] | $^1$H-NMR (δ ppm): | FAB-MS (M + H)[+] |
|---|---|---|---|---|
| 183 | (pentyl) | HN(Me)-CH2-CH(OH)-CH2-NH2 | 1.25–1.55(2H, m), 1.60–1.80(2H, m), 2.05–2.45(4H, m), 2.65–3.50(12H, m), 3.90–4.10(1H, m), 5.05–5.35(1H, m), 7.15–8.15(14H, m) | 533 |
| 184 | (butyl) | HN(Me)-CH2-CH(OH)-CH2-NH2 | 2.05–2.45(3H, m), 2.50–2.95(6H, m), 2.95–3.55(7H, m), 3.65–3.90(1H, m), 3.95–4.20(1H, m), 5.15(1H, m), 5.55(1H, bs), 7.15–8.15(14H, m) | 535 |
| 185 | (pentyl) | HN(Me)-CH2-CH(OH)-CH2-NH2 | 1.25–1.55(2H, m), 1.95–2.45(4H, m), 2.50–2.65(1H, m), 2.78(3H, s), 2.75–2.90(1H, m), 2.95–3.50(7H, m), 3.65–3.85(1H, m), 3.85–4.05(1H, m), 5.05–5.40(1H, m), 5.56(1H, bs), 7.10–8.10(14H, m) | 549 |

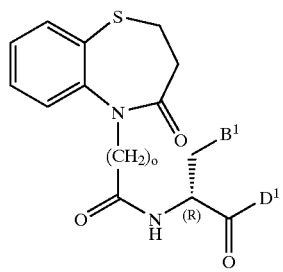

| Example number | o | B[1] | D[1] | $^1$H-NMR (δ ppm): | FAB-MS (M + H)[+] |
|---|---|---|---|---|---|
| 186 | 3 | 2-methylindole | HN(Me)-CH2-CH(OH)-CH2-NH2 | 1.30–1.65(2H, m), 1.95–2.20(2H, m), 2.25–2.65(3H, m), 2.70–2.95(2H, m), 3.00–3.45(5H, m), 3.50–3.85(2H, m), 3.90–4.15(1H, m), 4.42(1H, m), 5.50(1H, bs), 6.85–7.15 (3H, m), 7.15–7.65(6H, m), 7.83(2H, s), 8.01(1H, d), 8.16 (1H, t), 10.81(1H, s) | 524 |
| 187 | 2 | 4-methylbenzophenone | HN(Me)-(CH2)3-NH2 | 1.55–1.75(2H, m), 2.05–2.45(3H, m), 2.60–2.90(3H, m), 3.00–3.65(7H, m), 3.90–4.30(1H, m), 4.35–4.55(1H, m), 7.20–7.75(13H, m), 7.86(2H, s), 8.20(1H, t), 8.30(1H, d) | 559 |
| 188 | 3 | 4-methylbenzophenone | HN(Me)-(CH2)3-NH2 | 1.35–1.75(4H, m), 2.00–2.15(2H, m), 2.25–2.45(2H, m), 2.65–2.95(3H, m), 3.00–3.45(6H, m), 4.22(1H, bs), 4.46 (1H, m), 7.22(1H, t), 7.30–7.75(12H, m), 7.86(2H, m), 8.10–8.30(2H, m) | 573 |
| 189 | 2 | 4-methylbenzophenone | 3-(HN-CH2-CH(OH)-CH2-NH2)phenyl | 2.00–2.70(4H, m), 2.75–2.95(2H, m), 3.00–3.65(7H, m), 3.65–3.85(1H, m), 3.95–4.30(1H, m), 4.35–4.60(1H, m), 5.55(1H, bs), 7.20–7.75(13H, m), 7.85(2H, s), 8.15–8.40 (2H, m) | 575 |

| | | | | | |
|---|---|---|---|---|---|
| 190 | 3 | 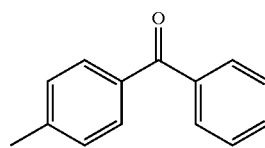 | 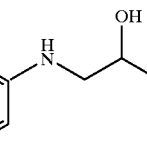 | 1.35–1.60(2H, m), 2.00–2.20(2H, m), 2.25–2.45(2H, m), 2.55–2.70(1H, m), 2.75–2.95(2H, m), 3.00–3.65(6H, m), 3.65–3.85(1H, m), 3.90–4.15(1H, m), 4.40–4.60(1H, m), 5.55(1H, bs), 7.22(1H, t), 7.30–7.75(12H, m), 7.89(2H, s), 8.17(1H, d), 8.28(1H, t) | 589 |
| 191 | 3 | 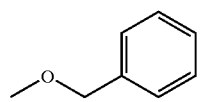 | 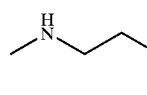 | 1.50–1.75(4H, m), 2.10–2.25(2H, m), 2.30–2.45(2H, m), 2.75(2H, q), 3.14(2H, q), 3.20–3.50(3H, m), 3.56(2H, d), 4.11(1H, bs), 4.41(1H, q), 4.47(2H, s), 7.22–7.35(6H, m), 7.45–7.55(2H, m), 7.61(1H, d), 7.08(2H, s), 2.05(1H, d), 8.18(1H, t) | 499 |
| 192 | 3 | 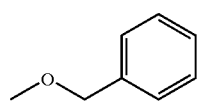 | 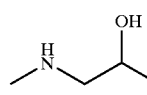 | 1.50–1.75(2H, m), 2.10–2.25(2H, m), 2.30–2.45(2H, m), 2.50–2.70(1H, m), 2.75–2.90(1H, m), 3.00–3.65(7H, m), 3.75(1H, bs), 4.12(1H, bs), 4.35–4.50(3H, m), 7.15–7.35(6H, m), 7.40–4.55(2H, m), 7.61(1H, d), 7.86(2H, s), 8.07(1H, d), 8.19(1H, t) | 515 |
| 193 | 2 | 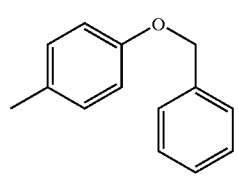 | 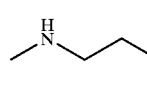 | 1.65(2H, m), 2.00–2.50(3H, m), 2.55–2.75(3H, m), 2.85(1H, dd), 3.09(2H, q), 3.15–3.60(3H, m), 4.02(1H, bs), 4.28(1H, bs), 5.03(2H, s), 6.87(2H, d), 7.10(2H, bd), 7.25–7.55(8H, m), 7.60(1H, d), 7.85(2H, bs), 8.12(1H, t), 8.19(1H, d) | 561 |
| 194 | 3 | 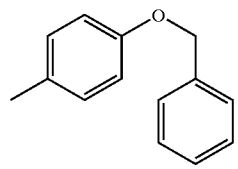 | 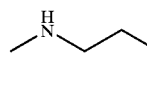 | 1.52(2H, bs), 1.66(2H, m), 2.07(2H, bs), 2.60–2.80(3H, m), 2.89(1H, dd), 3.11(2H, q), 3.15–3.45(3H, m), 4.02(1H, bs), 4.31(1H, m), 5.03(2H, s), 6.87(2H, d), 7.12(2H, d), 7.20–7.55(8H, m), 7.60(1H, d), 7.85(2H, bs), 8.05(1H, d), 8.14(1H, t) | 575 |
| 195 | 2 | 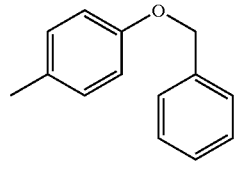 | 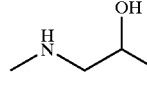 | 2.00–2.70(5H, m), 2.75–3.00(2H, m), 3.00–3.60(5H, m), 3.71(1H, bs), 4.10(1H, m), 4.32(1H, bs), 5.03(2H, s), 6.78(2H, d), 7.13(2H, d), 7.20–7.55(5H, m), 7.60(1H, d), 7.24(2H, bs), 8.05–8.25(2H, m) | 577 |
| 196 | 3 | 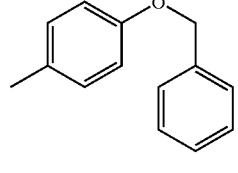 | 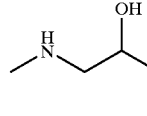 | 1.51(2H, bs), 2.06(2H, bs), 2.39(2H, bs), 2.55–2.75(2H, m), 2.55–3.00(2H, m), 3.00–3.80(5H, m), 4.02(1H, bs), 4.35(1H, m), 5.03(2H, s), 6.87(2H, d), 7.13(2H, d), 7.20–7.55(8H, m), 7.60(1H, d), 7.86(2H, bs), 8.04(1H, d), 8.18(1H, t) | 591 |
| 197 | 3 | 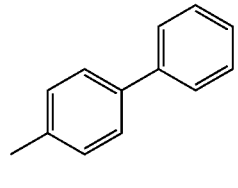 | 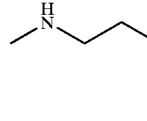 | 1.35–1.75(4H, m), 2.00–2.15(2H, m), 2.20–2.45(2H, m), 2.65–2.85(3H, m), 3.02(1H, dd), 3.05–3.55(5H, m), 4.00(1H, bs), 4.41(1H, m), 7.15–7.65(13H, m), 7.86(2H, s), 8.14(1H, d), 8.20(1H, t) | 545 |
| 198 | 3 | 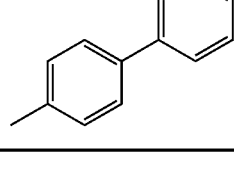 | 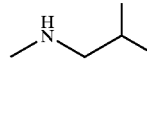 | 1.30–1.65(2H, m), 1.95–2.15(2H, m), 2.20–2.45(2H, m), 2.55–2.70(1H, m), 2.70–2.90(2H, m), 2.95–3.45(4H, m), 3.50–3.85(3H, m), 3.90–4.15(1H, m), 4.46(1H, m), 7.15–7.65(13H, m), 7.87(2H, s), 8.13(1H, d), 8.25(1H, t) | 561 |

-continued

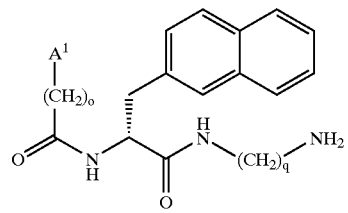

| Example number | o | q | A¹ | ¹H-NMR (δ ppm): | FAB-MS (M + H)⁺ |
|---|---|---|---|---|---|
| 199 | 2 | 2 | 5-methyl-10,11-dihydro-5H-dibenzo[b,f]azepin-6-one | 2.78(2H, m), 2.92(2H, m), 3.16(2H, m), 3.41(2H, m), 3.72(2H, q), 3.83(1H, m), 4.49–4.57(2H, m), 7.07–8.33(19H, m) | 521 |
| 200 | 2 | 3 | 5-methyl-10,11-dihydro-5H-dibenzo[b,f]azepin-6-one | 1.65(4H, bs), 2.70(2H, m), 2.88(1H, m), 3.10(2H, d), 3.70(2H, ABq), 3.82(2H, m), 4.47(1H, m), 4.58(1H, dd), 7.03–8.32(19H, m) | 535 |
| 201 | 3 | 2 | 5-methyl-10,11-dihydro-5H-dibenzo[b,f]azepin-6-one | 1.61(2H, m), 2.11(2H, m), 2.82(2H, m), 2.95(1H, m), 3.25(2H, m), 3.36(2H, m), 3.31(2H, ABq), 4.34(1H, m), 4.54(1H, m), 7.09–8.31(19H, m) | 535 |
| 202 | 3 | 3 | 5-methyl-10,11-dihydro-5H-dibenzo[b,f]azepin-6-one | 1.68(4H, d), 2.10(2H, m), 2.75(2H, m), 2.91(1H, m), 3.15(4H, m), 3.81(2H, ABq), 4.33(1H, m), 4.52(1H, m), 7.10–8.31(19H, m) | 549 |
| 203 | 4 | 2 | 5-methyl-10,11-dihydro-5H-dibenzo[b,f]azepin-6-one | 1.37(4H, bs), 2.05(2H, d), 2.85(2H, bs), 2.95(1H, m), 3.20(1H, m), 3.29(2H, m), 3.54(1H, m), 3.81(2H, ABq), 4.45(1H, m), 4.54(1H, m), 7.05–8.30(19H, m) | 549 |
| 204 | 4 | 3 | 5-methyl-10,11-dihydro-5H-dibenzo[b,f]azepin-6-one | 1.37(4H, bs), 1.66(2H, m), 2.05(2H, d), 2.71(2H, m), 2.92(1H, m), 3.12(2H, m), 3.54(1H, m), 3.81(2H, ABq), 4.43(1H, m), 4.52(2H, m), 7.07–8.31(19H, m) | 563 |
| 205 | 2 | 2 | 5-methyl-5H-dibenzo[b,f]azepine-6,11(10H)-dione | 2.80(2H, bs), 2.93(1H, m), 3.33(4H, m), 4.18(2H, m), 4.49(1H, m), 7.27–8.34(19H, m) | 535 |

-continued

| | | | | | |
|---|---|---|---|---|---|
| 206 | 2 | 3 | | 1.66(2H, m), 2.59–3.15(8H, m), 4.18(2H, m), 4.47(1H, m),7.26–8.33(19H, m) | 549 |
| 207 | 3 | 2 | | 1.68(2H, t), 2.07(2H, m), 2.80(2H, m), 2.92(2H, m), 3.22(2H, m), 3.63–3.97(2H, m), 4.55(1H, m), 7.29–8.38(19H, m) | 549 |
| 208 | 3 | 3 | | 1.70(4H, q) 2.09(2H, t), 2.74(1H, m), 2.92(1H, m), 3.16(4H, m), 3.61–3.94(2H, m), 4.55(1H, m), 7.28–8.27(19H, m) | 563 |
| 209 | 2 | 2 | | 0.85–1.15(2H, m), 2.10–2.62(4H, m), 2.76–3.80(8H, m), 4.29–4.38(1H, m), 4.42–4.55(1H, m), 6.69(1H, d), 6.77(1H, d), 6.86–7.07(3H, m), 7.12–7.38(4H, m), 7.40–7.52(3H, m), 7.72–7.89(5H, m), 8.28–8.32(2H, m) | 533 |
| 210 | 2 | 3 | | 1.63–1.69(4H, m), 2.25–2.38(1H, m), 2.67–2.70(2H, m), 2.76–2.89(1H, m), 3.10–3.29(4H, m), 3.25–3.40(3H, m), 4.20–4.50(2H, m), 6.71(1H, d), 6.78(1H, d), 6.82–7.07(4H, | 547 |
| 211 | 3 | 2 | | 1.01–1.14(2H, m), 2.06–2.64(2H, m), 2.74–3.02(3H, m), 3.15–3.97(7H, m), 4.23–4.37(1H, m), 4.40–4.52(1H, m), 6.73(1H, d), 6.82(1H, d), 6.86–7.09(3H, m), 7.12–7.30(2H, m), 7.37–7.57(3H, m), 7.69–7.99(5H, m), 8.26–8.34(2H, m) | 547 |
| 212 | 3 | 3 | | 1.30–1.50(4H, m), 1.64–1.72(2H, m), 2.02–2.06(2H, m), 2.74–2.80(2H, m), 2.89–3.00(2H, m), 3.14–3.42(7H, m), 4.10–4.50(2H, m), 6.72–7.23(4H, m), 7.40–7.60 (3H, m), 7.70–8.00(6H, m), 8.15–8.27(2H, m) | 561 |
| 213 | 4 | 2 | | 1.35–1.50(2H, m), 2.05–2.10(2H, m), 2.81–2.98(4H, m), 3.10–3.38(7H, m), 4.47–4.60(2H, m), 6.70(1H, d), 6.82(1H, d), 6.88–7.25(5H, m), 7.40–7.50(3H, m), 7.73 (1H, bs), 7.80–7.98(5H, m), 8.20–8.34(2H, m) | 561 |

| | | | | | |
|---|---|---|---|---|---|
| 214 | 4 | 3 | 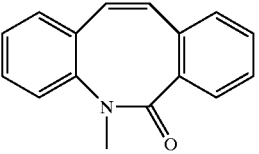 | 1.10–1.20(2H, m), 1.25–1.40(4H, m), 1.64–1.76(4H, m), 1.97–2.00(1H, m), 2.70–2.78(2H, m), 2.91–4.03(8H, m), 4.48–4.60(2H, m), 6.85–6.99(1H, m), 7.03–7.34 (5H, m), 7.41–7.48(3H, m), 7.63–7.84(6H, m), 8.13–8.32(2H, m) | 575 |
| 215 | 2 | 2 | 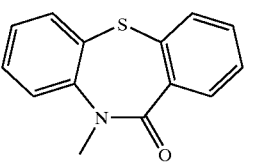 | 2.22–2.98(4H, m), 3.12(4H, m), 3.68(1H, m), 4.49(1H, m), 7.30–7.65(8H, m), 7.65–7.90(3H, m), 8.17(2H, bs), 8.35(2H, m) | 539 |
| 216 | 2 | 3 | 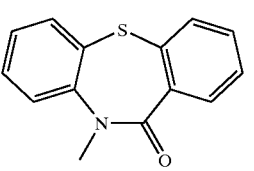 | 1.66(2H, m), 2.20–2.78(4H, m), 2.88(1H, m), 3.10(1H, m), 3.68(1H, m), 3.91(1H, m), 4.96(1H, m), 7.18(1H, m), 7.30–8.00(12H, m), 8.19(1H, m), 8.32(1H, t) | 553 |
| 217 | 3 | 2 | 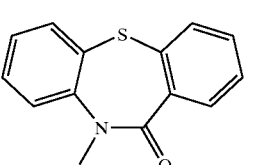 | 1.50(2H, m), 2.06(2H, m), 2.70–3.00(3H, m), 3.15–3.45(3H, m), 3.47(1H, m), 4.33 (1H, m), 4.44(1H, m), 7.10–7.86(1H, m), 7.91(2H, bs), 8.13(1H, d), 8.21(1H, m) | 553 |
| 218 | 3 | 3 | 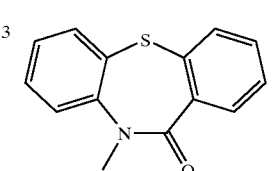 | 1.32–1.54(4H, m), 2.11(2H, m), 2.49–2.61(2H, m), 2.64–2.82(2H, m), 3.10(2H, m), 3.04–3.44(1H, m), 4.14–4.39(2H, m), 6.94–7.82(11H, m), 7.89(2H, bs), 8.18 (2H, m) | 567 |
| 219 | 4 | 2 | 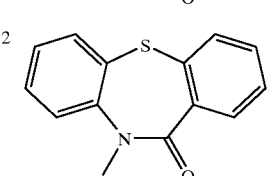 | 1.17–1.45(4H, m), 2.01(2H, m), 2.70–2.97(3H, m), 3.13–3.52(4H, m), 4.36–4.58 (2H, m), 7.17(1H, m), 7.34–7.52(5H, m), 7.54–7.63(2H, m), 7.69(1H, bs), 7.45–7.87(2H, m), 7.95(2H, bs), 8.14(1H, t), 8.26(1H, t) | 567 |
| 220 | 4 | 3 | 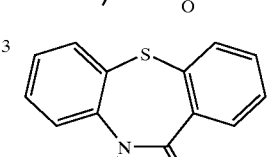 | 1.15–1.65(4H, m), 1.65(2H, t), 2.01(2H, m), 2.66–2.78(2H, m), 2.89(1H, m), 3.06–3.18(2H, m), 4.34–4.65(2H, m), 7.20(1H, m), 7.33–7.49(2H, m), 7.53–7.66 (2H, m), 7.69(1H, d), 7.75–7.89(4H, m), 8.12(1H, t), 8.18(1H, t) | 581 |
| 221 | 2 | 2 | 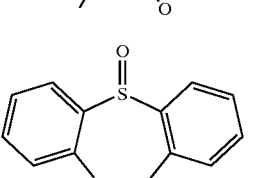 | 2.77(2H, m), 2.91(1H, dd), 3.10–3.40(4H, m), 3.15(1H, dd), 4.51(1H, m), 4.66–4.95(2H, m), 7.34–7.87(11H, m), 7.95(2H, bs), 8.27(1H, m), 8.37(1H, dd) | 555 |
| 222 | 2 | 3 | 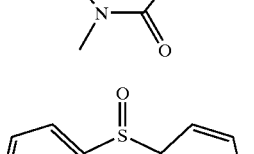 | 1.64(2H, m), 2.89(1H, dd), 2.40–3.65(7H, m), 3.78(1H, m), 4.46–4.64(2H, m), 7.35–8.05(13H, m), 8.19(1H, m), 8.36(1H, d) | 569 |

| | | | | | |
|---|---|---|---|---|---|
| 223 | 3 | 2 | 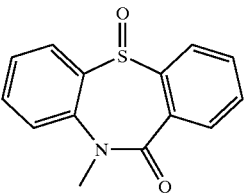 | 1.54–1.73(2H, m), 2.14(2H, m), 2.72–3.00(3H, m), 3.13–3.62(4H, m), 4.37(1H, m), 4.53(1H, m), 7.26–7.85(11H, m), 8.04(2H, m), 8.30(2H, m) | 569 |
| 224 | 3 | 3 | 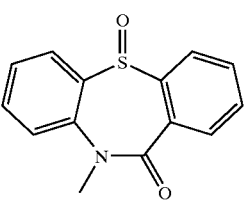 | 1.50–1.75(4H, m), 2.14(2H, t), 2.66–2.86(2H, m), 2.89(1H, m), 3.06–3.20(2H, m), 3.20–3.60(2H, m), 4.37(1H, m), 4.51(1H, m), 7.35–7.95(13H, m), 8.17–8.27 (2H, m) | 583 |
| 225 | 4 | 2 | 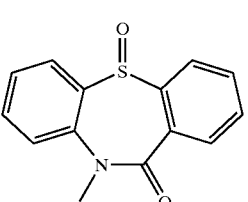 | 1.20–1.45(4H, m), 2.05(2H, m), 2.80(2H, m), 2.91(1H, m), 3.10–3.52(4H, m), 4.38–4.60(2H, m), 7.35–7.85(11H, m), 7.96(2H, m), 8.17(1H, dd), 8.27(1H, t) | 583 |
| 226 | 4 | 3 | 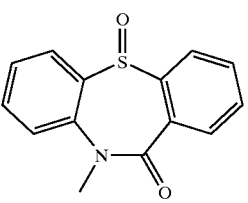 | 1.20–1.46(4H, m), 1.65(2H, m), 2.04(2H, m), 2.64–2.78(2H, m), 2.90(1H, m), 3.10 (1H, m), 3.15–3.55(2H, m), 4.33–4.65(2H, m), 7.36–7.88(13H, m), 8.17(1H, m) | 597 |
| 227 | 2 | 2 | 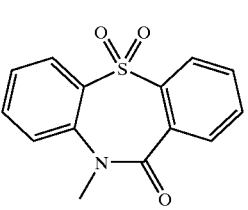 | 2.22–3.68(8H, m), 3.85(1H, m), 4.35–4.68(2H, m), 7.33–7.55(4H, m), 7.62–8.53 (11H, m) | 571 |
| 228 | 2 | 3 | 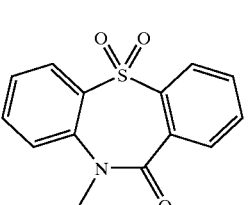 | 1.68(2H, m), 2.24–3.68(5H, m), 3.85(1H, m), 4.35–4.72(2H, m), 7.36–7.64(4H, m), 7.64–8.47(11H, m) | 585 |

| | | | | | |
|---|---|---|---|---|---|
| 229 | 3 | 2 | 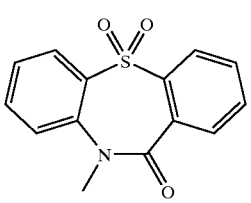 | 1.45–1.85(2H, m), 2.13(2H, m), 2.43–3.64(4H, m), 2.93(1H, dd), 3.22(1H, dd), 3.78(1H, m), 4.31(1H, m), 4.53(1H, m), 7.22–8.18(13H, m), 8.18–8.37(2H, m) | 585 |
| 230 | 3 | 3 | 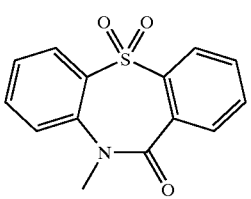 | 1.67(4H, m), 2.12(2H, m), 2.42–3.62(6H, m), 3.73(1H, m), 4.33(1H, m), 4.51(1H, m), 7.23–8.02(13H, m), 8.22(2H, m) | 599 |
| 231 | 4 | 2 | 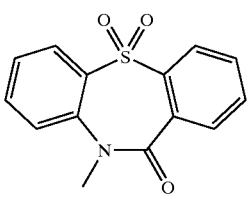 | 1.27–1.55(4H, m), 2.04(2H, m), 2.80(2H, m), 2.93(1H, dd), 3.23–3.45(2H, m), 3.29(1H, dd), 3.67(1H, m), 4.36(1H, m), 4.52(1H, m), 7.36–7.52(4H, m), 7.68–8.04 (9H, m), 8.17(1H, t), 8.26(1H, t) | 599 |
| 232 | 4 | 3 | 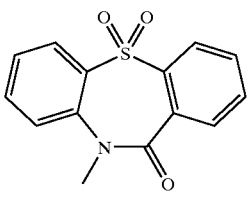 | 1.28–1.58(4H, m), 1.65(2H, m), 2.04(2H, m), 2.66–2.78(2H, m), 2.91(1H, m), 3.10(2H, m), 3.20–3.50(1H, m), 3.67(1H, m), 4.37(1H, m), 4.51(1H, m), 7.36–7.53 (4H, m), 7.67–7.97(9H, m), 8.12–8.20(2H, m) | 613 |
| 233 | 2 | 3 | 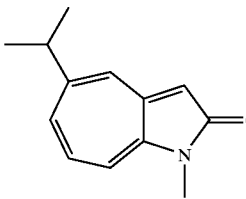 | 1.28(6H, d), 1.60–1.68(2H, m), 2.62–2.93(5H, m), 3.07–3.17(4H, m), 4.14 (2H, t), 4.40–4.50(1H, m), 7.33–7.47(4H, m), 7.61–7.85(9H, m), 8.20(1H, t), 8.44(1H, d) | 538 |
| 234 | 3 | 3 | 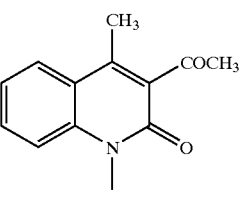 | 1.71(4H, m), 2.19(2H, m), 2.34(3H, s), 2.45(3H, s), 2.74(2H, m), 2.91(1H, m), 3.16 (3H, m), 3.48(1H, bs), 3.96(1H, bs), 4.66(1H, m), 7.32(4H, m), 7.45(1H, d), 7.56 (2H, m), 7.68(3H, m), 7.90(3H, m), 8.36(2H, m) | 541 |
| 235 | 2 | 3 | 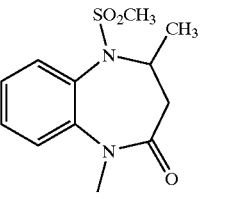 | 1.07, 1.11(3H, d), 1.66(2H, m), 1.80–2.15(1H, m), 2.20–2.80(5H, m), 2.89, 3.01 (3H, s), 3.15(3H, m), 3.65–3.95(2H, m), 4.45–4.80(2H, m), 7.25–7.55(6H, m), 7.65–7.95(7H, m), 8.15–8.50(2H, m) | 580 |

-continued

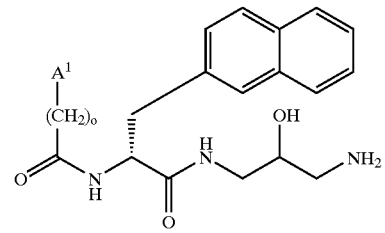

| Example number | o | A¹ | ¹H-NMR (δ ppm): | FAB-MS (M + H)⁺ |
|---|---|---|---|---|
| 236 | 2 | *N-methyl dibenzazepinone* | 2.47(2H, m), 2.86(2H, m), 3.09(4H, m), 3.79–4.05(4H, m),4.55(2H, m), 7.03–8.31 (20H, m) | 551 |
| 237 | 3 | *N-methyl dibenzazepinone* | 1.64(2H, m), 2.09(2H, m), 2.63(1H, m), 2.89(2H, m), 3.15(4H, m), 3.75(1H, m), 3.80 (2H, ABq), 4.30(1H, m), 4.56(1H, m), 7.08–8.31(20H, m) | 565 |
| 238 | 4 | *N-methyl dibenzazepinone* | 1.40(9H, s), 1.62(4H, bs), 1.75(2H, bs), 2.22(2H, bs), 2.90(1H, m), 3.22(4H, bs), 4.09(1H, m), 4.52(1H, m), 4.75(1H, m), 5.01(1H, m), 6.45(1H, m), 6.81(1H, bs), 7.08–7.77(15H, m) | 579 |
| 239 | 2 | *N-methyl dibenzazocinone* | 1.05–1.18(4H, m), 1.22–1.39(2H, m), 1.95–2.05(2H, m), 2.80–3.38(11H, m), 4.50–4.60(2H, m), 6.85–7.27(5H, m) 7.50–7.34(4H, m), 7.68–7.90(4H, m), 7.90–8.00(2H, m), 8.15–8.31(2H, m) | 563 |
| 240 | 3 | *N-methyl dibenzazocinone* | 1.01–1.14(2H, m), 2.10–2.03(2H, m), 2.54–2.72(1H, m), 2.72–3.00(3H, m), 3.02–4.25(10H, m), 4.62–4.50(1H, m), 6.65–7.30(8H, m), 7.35–7.58(3H, m), 7.70–7.96(4H, m), 8.10–8.47(2H, m) | 577 |
| 241 | 4 | *N-methyl dibenzazocinone* | 1.12–1.18(2H, m), 1.23–1.49(2H, m), 1.76(1H, d), 2.14–1.99(2H, m), 2.79–2.49(1H, m), 2.86–3.65(9H, m), 3.80–3.65(1H, m), 4.09–4.55(1H, m), 4.50–4.60(1H, m), 5.53 (1H, bs), 6.81–7.36(8H, m), 7.39–7.78(3H, m), 7.80–7.99(4H, m), 8.09–8.30(2H, m) | 591 |
| 242 | 2 | *N-methyl dibenzazepinedione* | 2.61(2H, m), 2.85–2.94(2H, m), 3.11(4H, m), 3.72(1H, m), 4.15(2H, m), 4.51(1H, m), 7.27–8.32(20H, m) | 565 |

| | | | | |
|---|---|---|---|---|
| 243 | 3 | 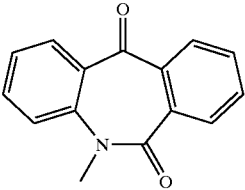 | 1.67(2H, m), 1.84(2H, m), 2.03–2.32(3H, m), 2.86(2H, m), 3.18(2H, m), 4.15(1H, t), 4.58(1H, m), 7.29–8.31(20H, m) | 579 |
| 244 | 2 | 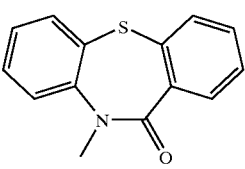 | 2.55–3.60(8H, m), 3.71(2H, m), 4.55(2H, m), 5.52(1H, m), 7.35–8.00(13H, m), 8.24(1H, m), 8.35(1H, m) | 569 |
| 245 | 3 | 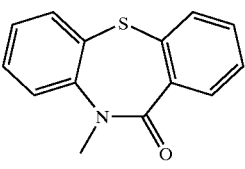 | 1.55(2H, m), 2.11(2H, m), 2.44(1H, m), 2.54–3.44(6H, m), 4.35(1H, m), 4.53(1H, m), 5.55(1H, m), 7.10–7.97(13H, m), 8.05–8.30(2H, m) | 583 |
| 246 | 3 | 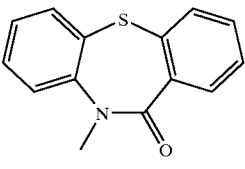 | 1.13–1.60(4H, m), 1.99(2H, m), 2.45–3.80(8H, m), 4.42(1H, m), 4.56(1H, m), 7.19(1H, m),7.33–7.53(5H, m), 7.53–7.66(2H, m), 7.70(1H, m), 7.74–7.95(4H, m) | 597 |
| 247 | 2 | 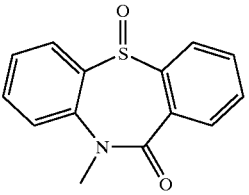 | 2.22–3.45(7H, m), 3.74(2H, m), 4.51(2H, m), 5.59(1H, d), 7.32–7.65(7H, m), 7.39(1H, m), 7.74(1H, m), 7.78(1H, m), 7.85(1H, m), 7.90–8.03(2H, m), 8.24–8.39(2H, m) | 585 |
| 248 | 3 | 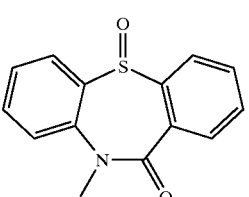 | 1.62(2H, m), 2.13(2H, t), 2.40–3.62(7H, m), 3.74(1H, m), 4.36(1H, m), 4.56(1H, m), 5.56(1H, d), 7.37–7.90(13H, m), 8.25(2H, d) | 599 |
| 249 | 4 | 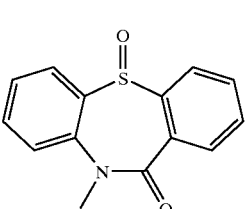 | 1.15–1.45(4H, m), 2.03(2H, m), 2.40–2.68(1H, m), 2.68–2.95(2H, m), 3.00–3.20 (2H, m), 3.20–3.60(2H, m), 3.72(1H, m), 4.44(1H, m), 4.55(1H, m), 5.55(1H, bs), 7.36–7.87(13H, m), 8.14(1H, m), 8.22(1H, m) | 613 |
| 250 | 2 | 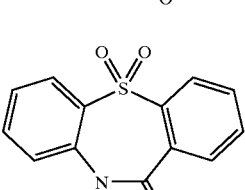 | 2.20–2.70(3H, m), 2.70–2.95(2H, m), 3.05–3.25(2H, m), 3.27–3.47(1H, m), 3.65–3.95(2H, m), 4.33–4.70(2H, m), 5.55(1H, m), 7.37–7.53(4H, m), 7.60–8.46(1H, m) | 601 |

-continued
| | | | | FAB-MS (M + H)+ |
|---|---|---|---|---|
| 251 | 3 | 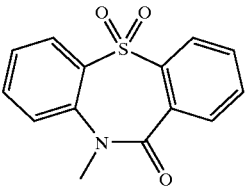 | 1.45–1.85(2H, m), 2.10(2H, m), 2.45–3.60(7H, m), 2.78(1H, dd), 4.16–4.61(2H, m), 5.58(1H, d), 7.20–8.34(15H, m) | 615 |
| 252 | 4 | 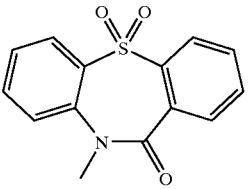 | 1.25–1.57(4H, m), 2.02(2H, m), 2.40–3.79(6H, m), 4.28–4.60(4H, m), 5.55(1H, d), 7.37–7.57(4H, m), 7.63–8.00(9H, m), 8.13(1H, t), 8.22(1H, t) | 629 |
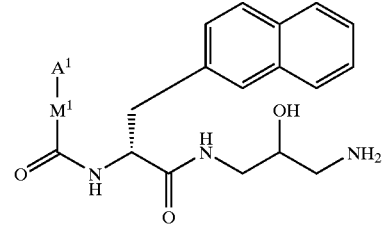
| Example number | A$^1$ | M$^1$ | $^1$H-NMR (δ ppm): | FAB-MS (M + H)$^+$ |
|---|---|---|---|---|
| 253 | 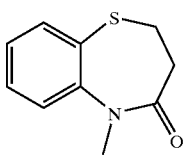 | 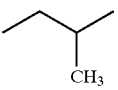 | 0.45–1.15(3H, m), 2.15–2.45(2H, m), 2.50–2.70(1H, m), 2.75–3.00(2H, m), 3.20–3.55(8H, m), 3.60–3.85(1H, m), 4.05–4.65(1H, m), 5.56(1H, bs), 7.10–8.35(15H, m) | 535 |
| 254 | 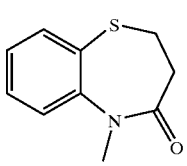 | 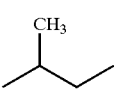 | 0.68(1H, d), 0.85–1.05(2H, m), 2.00–3.30(10H, m), 3.60–4.70(5H, m), 7.20–8.00(13H, m), 8.15–8.40(2H, m) | 535 |
| 255 | 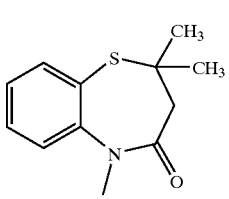 | 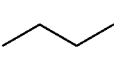 | 1.23(3H, m), 1.44(3H, m), 2.14(4H, m), 2.56(1H, m), 2.85 (2H, m), 3.12(3H, m), 3.72(1H, m), 3.95–4.25(1H, m), 4.49 (1H, m), 5.53(1H, d), 7.26(1H, m), 7.35–7.60(6H, m), 7.65–7.95(6H, m), 8.19(1H, d), 8.27(1H, t) | 549 |
| 256 | 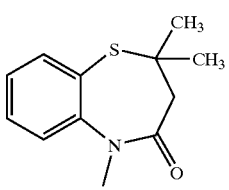 | 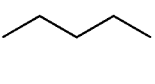 | 1.23(3H, m), 1.45(5H, m), 2.04(2H, m), 2.17(2H, m), 2.61 (1H, bs), 2.90(1H, m), 3.15(3H, m), 3.74(1H, m), 3.95(1H, m), 4.53(1H, m), 5.55(1H, bs), 7.25(1H, m), 7.35–7.65(6H, m), 7.70–7.95(6H, m), 8.13(1H, t), 8.23(1H, d) | 563 |
| 257 | 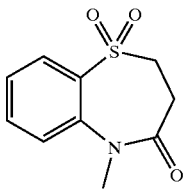 | 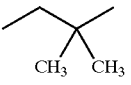 | 1.03(3H, s), 1.10(3H, s), 2.60(2H, t), 2.90(3H, m), 3.19(3H, m), 3.59(2H, t), 3.76(1H, m), 4.62(1H, m), 7.06(1H, t), 7.23 (1H, t), 7.35(1H, d), 7.45(3H, m), 7.65–7.95(8H, m), 8.22 (1H, t) | 581 |

| | | | | |
|---|---|---|---|---|
| 258 | 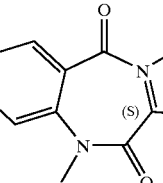 |  | 1.16(1H, m), 1.50(1H, m), 1.64–1.89(2H, m), 1.90–2.23 (3H, m), 2.28–2.96(6H, m), 3.00–3.28(3H, m), 3.72(1H, m), 4.13(1H, m), 4.49(1H, m), 5.56(1H, bs) | 535 |
| 259 | 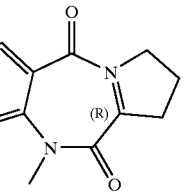 |  | 1.90(4H, m), 2.25(2H, t), 2.42(1H, m), 2.70–2.95(2H, m), 3.00–3.20(3H, m), 3.40(1H, m), 3.56(1H, m), 3.70(2H, m), 4.05–4.25(2H, m), 4.46(1H, m), 5.53(1H, d), 7.35–7.52(4H, m), 7.61(1H, dd), 7.68(1H, d), 7.70–7.95(6H, m), 8.19(1H, t), 8.26(1H, m) | 592 |
| 260 | 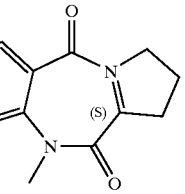 |  | 1.90(4H, m), 2.20–2.60(3H, m), 2.85(2H, m), 3.14(3H, m), 3.40(1H, m), 3.57(1H, m), 3.74(2H, m), 4.02(2H, m), 4.52 (1H, m), 7.30–7.60(7H, m), 7.70–7.95(6H, m), 8.22(1H, t), 8.32(1H, d) | 558 |
| 261 | 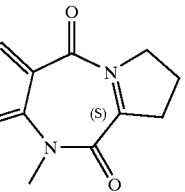 | 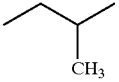 | 1.50(2H, m), 1.95(6H, m), 2.42(1H, m), 2.60(1H, m), 2.75–2.95(2H, m), 3.15(3H, m), 3.35–3.80(4H, m), 4.03(1H, m), 4.56(1H, m), 7.40(5H, m), 7.56(1H, m), 7.71(5H, m), 7.88 (2H, bs), 8.18(1H, d), 8.27(1H, t) | 572 |
| 262 | 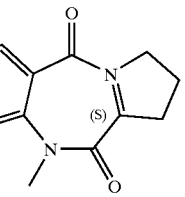 | 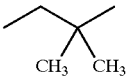 | 0.35–0.80(3H, m), 1.92(4H, m), 2.20–3.90(11H, m), 4.07 (1H, m), 4.14–4.62(2H, m), 7.20–7.62(6H, m), 7.63–8.00 (7H, m), 8.01–8.38(2H, m) | 572 |
| 263 | 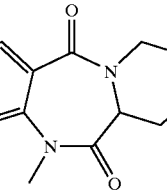 |  | 0.40–0.90(6H, m), 1.91(4H, m), 2.40(1H, m), 2.62(1H, m), 2.87(1H, m), 2.95–2.85(7H, m), 4.04(1H, m), 7.25–7.50 (6H, m), 7.69(2H, m), 7.75–8.00(6H, m), 8.16(1H, m) | 586 |
| 264 | | | 1.25–2.00(6H, m), 2.27(2H, m), 2.50–2.95(3H, m), 3.12 (3H, m), 3.72(3H, m), 4.11(1H, m), 4.28(1H, m), 4.48(1H, m), 7.25–7.60(6H, m), 7.60–7.73(2H, m), 7.74–7.95 (5H, m), 8.18(1H, t), 8.32(1H, d) | 572 |

-continued
| | | | | FAB-MS (M + H)+ |
|---|---|---|---|---|
| 265 | 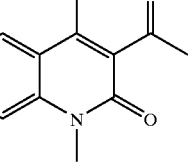 |  | 2.20(3H, s), 2.58–3.45(8H, m), 3.72–3.88(1H, m), 4.25–4.50(2H, m), 4.60–4.72(1H, m), 5.64(1H, bs), 7.13–7.35(4H, m), 7.44–7.65(8H, m), 7.77–7.97(6H, m), 8.39(1H, t), 8.59(1H, d) | 605 |
| 266 | 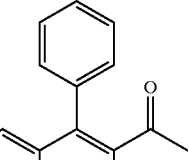 |  | 1.50–1.70(2H, m), 2.23(3H, s), 2.57–3.55(8H, m), 3.75–3.85(1H, m), 4.30–4.50(2H, m), 4.60–4.70(1H, m), 5.70(1H, bs), 7.15–7.37(4H, m), 7.44–7.66(8H, m), 7.77–7.98(6H, m), 8.35(1H, t), 8.60(1H, d) | 619 |
| 267 | 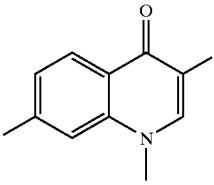 |  | 1.28(3H, t), 2.58–3.26(6H, m), 3.88–4.03(1H, m), 4.21 (2H, q), 4.61–4.74(1H, m), 5.12(2H, s), 7.38–7.58(5H, m), 7.70–7.88(4H, m), 7.90(2H, bs), 8.18(1H, d), 8.50 (1H, bt), 8.62(1H, s), 9.00(1H, d) | 579 |
| 268 | 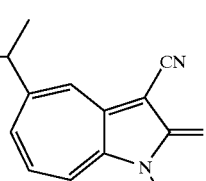 | 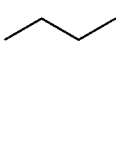 | 1.28(6H, d), 2.63–2.73(1H, m), 2.74–2.94(2H, m), 3.12–3.19(4H, m), 3.33(2H, s), 3.74–3.82(1H, m), 4.13(2H, t), 4.53–4.56(1H, m), 5.56(1H, bs), 7.35–7.49(4H, m), 7.61–7.89(9H, m), 8.23(1H, t), 8.31–8.46(1H, m) | 554 |
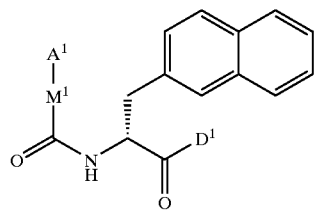
| Example number | A¹ | M¹ | D¹ | ¹H-NMR (δ ppm): | FAB-MS (M + H)+ |
|---|---|---|---|---|---|
| 269 | 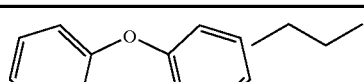 | | 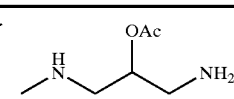 | 2.01, 2.04(3H, s), 2.35–3.63(8H, m), 4.05(2H, m), 4.54(1H, m), 4.95(1H, m), 7.21(2H, m), 7.31 3H, m), 7.44(4H, m), 7.56(1H, m), 7.65–7.90 (5H, m), 8.08(2H, bs), 8.36(2H, m) | 595 |
| 270 | 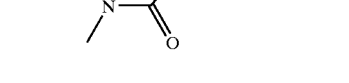 | |  | 2.55(2H, m), 2.93(1H, m), 3.20(1H, m), 3.35(2H, m), 4.06(4H, m), 4.65(1H, m), 7.20(2H, m), 7.32 (3H, m), 7.45(5H, m), 7.56(1H, m), 7.68(1H, m), 7.70–7.90(4H, m), 8.20(2H, bs), 8.44(1H, d), 8.58(1H, t) | 551 |

-continued
| 271 | 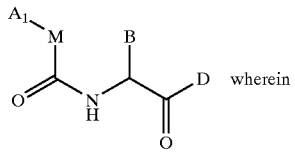 | | 1.16(1H, m), 1.50(1H, m), 1.65–2.25(7H, m), 2.30–3.30(4H, m), 3.85–4.25(3H, m), 4.47(1H, m), 7.24(4H, m), 7.46(3H, m), 7.72(1H, s), 7.75–7.95(3H, m), 8.05–8.60(4H, m), 10.08, 10.30(1H, bs) | 530 |
| Example number | Structure | $^1$H-NMR (δ ppm): | FAB-MS (M + H)$^+$ |
|---|---|---|---|
| 272 | 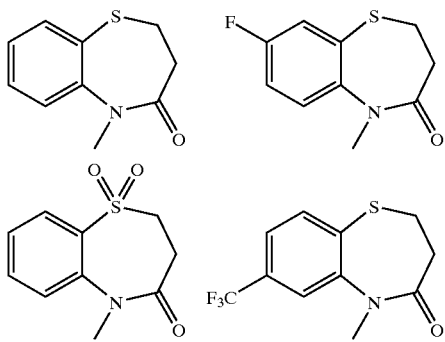 | 1.64–1.70(4H, m), 2.42–2.82(6H, m), 3.11–3.18(8H, m), 3.34–3.50(3H, m), 4.08–4.14(4H, m), 4.20–4.60(2H, m), 6.29–7.40(11H, m), 7.84(1H, bs), 8.10–8.20(1H, m) | 551 |
| 273 | 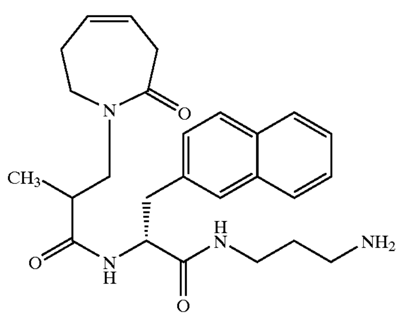 | 0.67(2H, d), 0.85(2H, d), 1.00–1.35(2H, m), 1.35–1.65(3H, m), 2.25–2.70(3H, m), 2.70–3.55(10H, m), 3.65–3.85(1H, m), 4.50–4.80(1H, m), 6.05(1H, bs), 7.25–7.55(3H, m), 7.65–8.05(6H, m), 8.20–8.40(2H, m) | 469 |
What is claimed is:
1. A compound having the following formula:
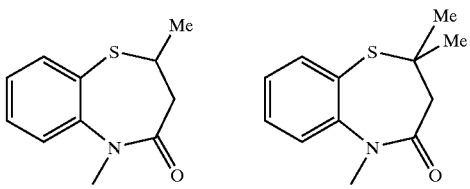 wherein
A$_1$ is
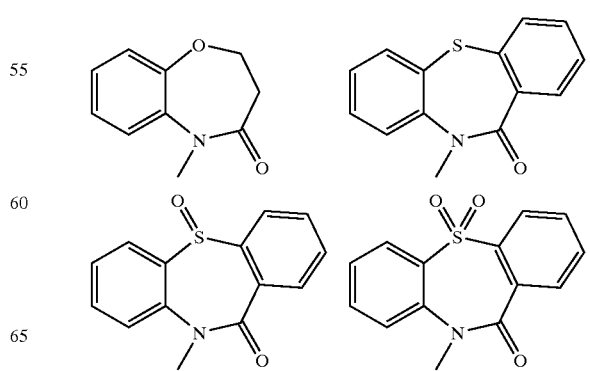

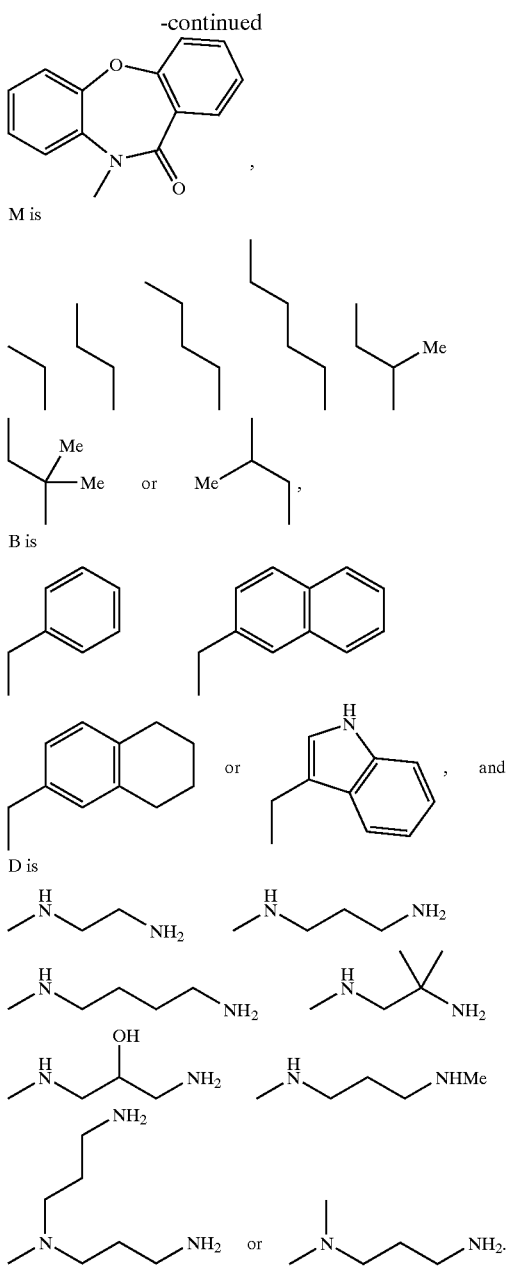

2. A composition which comprises an inert carrier and a compound according to claim 1.

3. A composition which comprises an inert carrier, a compound according to claim 1 and at least one of the following components:
   a growth hormone secretagogues selected from KP-102 (GHRP-2), GHRP-6, Hexarelin, and GHRP-1,
   a growth hormone releasing factor (GRF) selected from IGF-1, IGF-2 and B-HT920.

4. A method for increasing levels of endogenous growth hormones in a human or an animal which comprises administering to such human or animal an effective amount of a compound according to claim 1.

5. A method for treating diseases or conditions which may be treated by growth hormone which comprises administering to a human or an animal of such treatment an amount of a compound according to claim 1 which is effective in promoting release of said growth hormone.

6. A method of claim 5 wherein the disease or condition is selected from the group consisting of osteoporosis; catabolic illness; immune deficiency, hip fracture; musculoskeletal impairment in the elderly; growth hormone deficiency in adults or in children; obesity; cachexia and protein loss due to chronic illness and treatment of patients recovering from major surgery, wounds and burns.

7. A method for increasing the level of growth hormone in a human or an animal which comprises administering to a human or animal a compound according to claim 1 in combination with any one of the following components:
   an additional growth hormone secretagogue selected from KP-102(GHRP-2), GHRP-6, Hexarelin and GHRP-1, a growth hormone releasing factor (GRF) selected from IGF-1, IGF-2 and B-HT920, and a growth hormone.

8. A method for the treatment of osteoporosis which comprises administering to a patient with osteoporosis a combination of a bisphosphonate compound and a compound according to claim 1.

9. A method for the treatment of bone fractures, wounds or burns which comprises administering to a patient with bone fractures, wounds or burns a combination of fibroblast growth factor (FGF) or platelet-derived growth factor (PDGF) and a compound of claim 1.

10. A method to increase the rate and extent of growth of animals, to increase the milk or wool production of animals the method comprising administering to a subject in need thereof an effective amount of a compound according to claim 1.

11. A compound selected from:

N-(2-Aminoethyl)-3-phenyl-2(R)-[2-(1,1,4-trioxo-2,3-dihydro-[1,5]benzothiazepin-5-yl)-acetylamino]propionamide;

N-[1(R)-(3-Aminopropylcarbamoyl)-2-(naphthalen-2-yl)ethyl]-3-(4-oxo-2,3-dihydro-[1,5]benzothiazepin-5-yl)propionamide;

N-[1(R)-(4-Aminobutylcarbamoyl)-2-(naphthalen-2-yl)ethyl]-3-(4-oxo-2,3-dihydro-[1,5]benzothiazepin-5-yl)propionamide;

N-(4-Aminobutyl)-3-(naphthalen-2-yl)-2(R)-[2-(4-oxo-2,3-dihydro-[1,5]benzothiazepin-5-yl)-acetylamino]propionamide;

N-[1(R)-(3-Aminopropylcarbamoyl)-2-(naphthalen-2-yl)ethyl]-3-(11-oxo-11H-dibenzo[b,f][1,4]oxazepin-10-yl)propionamide;

N-[1(R)-(3-Aminopropylcarbamoyl)-2-(naphthalen-2-yl)ethyl]-4-(4-oxo-2,3-dihydro-[1,5]benzothiazepin-5-yl)butyramide;

N-(2-Amino-2-methylpropyl)-3-(naphthalen-2-yl)-2(R)-[3-(4-oxo-2,3-dihydro-[1,5]benzothiazepin-5-yl)-propionylamino]propionamide;

N-[1(R)-(3-Aminopropylcarbamoyl)-2-(naphthalen-2-yl)ethyl]-3-(2-methyl-4-oxo-2,3-dihydro[1,5]benzothiazepin-5-yl)propionamide;

N-[1(R)-(3-Methylamino-propylcarbamoyl)-2-(naphthalen-2-yl)ethyl-]-3-(4-oxo-2,3-dihydro-[1,5]benzothiazepin-5-yl)propionamide;

N-[1(R)-(3-Methylamino-propylcarbamoyl)-2-(naphthalen-2-yl)ethyl]-4-(4-oxo-2,3-dihydro-[1,5]benzothiazepin-5-yl)butyramide;

N-(1(R)-[(3-Aminopropyl)-methylcarbamoyl]-2-(naphthalen-2-yl)ethyl)-4-(4-oxo-2,3-dihydro-[1,5]benzothiazepin-5-yl)butyramide;

N-(3-Amino-2-hydroxypropyl)-3-(naphthalen-2-yl)-2(R)-[3-(4-oxo-2,3-dihydro-[1,5]benzothiazepin-5-yl)-propionylamino]propionamide;

N-[1(R)-(3-Amino-2-hydroxypropylcarbamoyl)-2-(naphthalen-2-yl)ethyl]-4-(4-oxo-2,3-dihydro-[1,5]benzothiazepin-5-yl)butyramide;
N-[1(R)-(2-Amino-ethylcarbamoyl)-2-(naphthalen-2-yl)ethyl]-4-(4-oxo-2,3-dihydro-[1,5]benzothiazepin-5-yl)butyramide;
N-(1(R)-[Bis-(3-aminopropyl)carbamoyl]-2-(naphthalen-2-yl)ethyl)-4-(4-oxo-2,3-dihydro-[1,5]benzothiazepin-5-yl)butyramide;
N-[1(R)-(3-Amino-propylcarbamoyl)-2-(naphthalen-2-yl)ethyl]-4-(1,1,4-trioxo-2,3-dihydro-[1,5]benzothiazepin-5-yl)butyramide;
N-[1(R)-(3-Aminopropylcarbamoyl)-2-(naphthalen-2-yl)ethyl]-4-(11-oxo-11H-dibenzo[b,f][1,4]oxazepin-10-yl)butyramide;
N-[1(R)-(3-Aminopropylcarbamoyl)-2-(naphthalen-2-yl)ethyl]-5-(4-oxo-2,3-dihydro-[1,5]benzothiazepin-5-yl)pentanamide;
N-[1(R)-(2-aminoethylcarbamoyl)-2-(naphthalen-2-yl)ethyl]-5-(4-oxo-2,3-dihydro-[1,5]benzothiazepin-5-yl)pentanamide;
N-[1(R)-(3-Aminopropylcarbamoyl)-2-(1H-indol-3-yl)-ethyl]-4-(4-oxo-2,3-dihydro-[1,5]-benzothiazepin-5-yl)butyramide;
N-[1(R)-(3-Aminopropylcarbamoyl)-2-(5,6,7,8-tetrahydro-naphthalen-2-yl)ethyl]-4-(4-oxo-2,3-dihydro-[1,5]-benzothiazepin-5-yl)butyramide;
N-[1(R)-(3-Amino-2-hydroxypropylcarbamoyl)-2-(naphthalen-2-yl)ethyl]-3-(11-oxo-11H-dibenzo[b,f][1,4]oxazepin-10-yl)propionamide;
N-[1(R)-(3-Aminopropylcarbamoyl)-2-(naphthalen-2-yl)ethyl]-4-(1,4-dioxo-2,3-dihydro-[1,5]benzothiazepin-5-yl)butyramide;
N-[1(R)-(3-Aminopropylcarbamoyl)-2-(naphthalen-2-yl)ethyl]-4-(4-oxo-2,3-dihydro-[1,5]-benzoxazepin-5-yl)butyramide;
N-[1(R)-(3-Amino-2-hydroxypropylcarbamoyl)-2-(naphthalen-2-yl)ethyl]-3-(2-methyl-4-oxo-2,3-dihydro[1,5]benzothiazepin-5-yl)propionamide;
N-[1(R)-(3-Aminopropylcarbamoyl)-2-(naphthalen-2-yl)ethyl]-3-(8-fluoro-4-oxo-[1,5]benzothiazepin-5-yl)propionamide;
N-[1(R)-(2-Aminoethylcarbamoyl)-2-(naphthalene-2-yl)ethyl]-3-(8-fluoro-4-oxo-2,3-dihydro-[1,5]benzothiazepin-5-yl)propionamide;
N-(3-Amino-2-hydroxypropyl)-3-(naphthalene-2-yl)-2(R)-[3-(4-oxo-7-trifluoromethyl-2,3-dihydro-[1,5]benzothiazepin-5-1)propionylamino]propionamide;
N-[1(R)-(3-Amino-2-hydroxypropylcarbamoyl)-2-(naphthalen-2-yl)ethyl]-4-(4-oxo-2,3-dihydro-[1,5]-benzoxazepin-5-yl)butyramide;
N-(3-Amino-2-hydroxypropyl)-3-(naphthalen-2-yl)-2(R)-[3-(4-oxo-2,3-dihydro-[1,5]-benzoxazepin-5-yl)propionylamino]propionamide;
N-[1(R)-(3-Amino-2-hydroxypropylcarbamoyl)-2-(naphthalen-2-yl)ethyl]-4-(8-fluoro-4-oxo-2,3-dihydro-[1,5]benzothiazepin-5-yl)butyramide;
N-(3-Amino-2-hydroxypropyl)-2(R)-[3-(8-fluoro-4-oxo-2,3-dihydro-[1,5]benzothiazepin-5-yl)propionylamino]-3-(naphthalen-2-yl)propionamide;
N-[1(R)-(3-Aminopropylcarbamoyl)-2-(naphthalen-2-yl)ethyl]-4-(8-fluoro-4-oxo-[1,5]-benzothiazepin-5-yl)butyramide;
N-[1(R)-(3-Aminopropylcarbamoyl)-2-(naphthalen-2-yl)ethyl]-3-(11-oxo-11H-dibenzo[b,f][1,4]thiazepin-10-yl)propionamide;
N-[1(R)-(3-Amino-2-hydroxypropylcarbamoyl)-2-(naphthalen-2-yl)ethyl]-3-(11-oxo-11H-dibenzo[b,f][1,4]-thiazepin-10-yl)propionamide;
N-[1(R)-(3-Amino-2-hydroxypropylcarbamoyl)-2-(naphthalen-2-yl)ethyl]-5-(5,11-dioxo-5,11-dihydrodibenzo-[b,f][1,4]thiazepin-10-yl)pentanamide;
N-[1(R)-(3-Amino-2-hydroxypropylcarbamoyl)-2-(naphthalen-2-yl)ethyl]-5-(5,5,11-trioxo-5,11-dihydro-dibenzo[b,f][1,4]thiazepin-10-yl)pentanamide;
N-[1(R)-(3-Amino-2-hydroxypropylcarbamoyl)-2-(naphthalen-2-yl)ethyl]-3-(2,2-dimethyl-4-oxo-3,4-dihydro-2H-benzo[1,5]thiazepin-5-yl)propionamide;
N-[1(R)-(3-Aminopropylcarbamoyl)-2-(naphthalen-2-yl)ethyl]-2-methyl-3-(4-oxo-3,4-dihydro-2H-benzo[1,5]-thiazepin-5-yl)propionamide;
N-[1(R)-(3-Amino-2-hydroxypropylcarbamoyl)-2-(naphthalen-2-yl)ethyl]-2-methyl-3-(4-oxo-3,4-dihydro-2H-benzo[1,5]thiazepin-5-yl)propionamide;
N-[1(R)-(3-amino-2(S)-hydroxypropylcarbamoyl)-2-(naphthalen-2-yl)ethyl]-4-(4-oxo-3,4-dihydro-[1,5]-benzothiazepin-5-yl)butyramide;
N-[1(R)-(3-amino-2(R)-hydroxy-propylcarbamoyl)-2-(naphthalen-2-yl)ethyl]-4-(4-oxo-3,4-dihydro-[1,5]-benzothiazepin-5-yl) butanamide;
N-[1(R)-(3-Amino-2-hydroxypropylcarbamoyl)-2-(naphthalen-2-yl)ethyl]-2,2-dimethyl-3-(1,1,4-trioxo-benzo-[-1,5]thiazepin-5-yl)propionamide;
N-[1(R)-(2-Amino-ethylcarbamoyl)-2-(naphthalen-2-yl)ethyl]-2-methyl-3-(4-oxo-3,4-dihydro-[1,5]benzothiazepin-5-yl)propionamide;
N-[1(R)-(3-Amino-2-hydroxypropylcarbamoyl)-2-(naphthalen-2-yl)ethyl]-3-(4-oxo-3,4-dihydro[1,5]benzothiazepin-5-yl)butyramide; and
N-[1(R)-[2-Hydroxy-3-(2(R)-hydroxypropylamino)propylcarbamoyl]-2-naphthalen-2-yl-ethyl]-4-(4-oxo-2,3-dihydro-[1,5]benzothiazepin-5-yl)butyramide.

* * * * *